United States Patent
Walters et al.

(10) Patent No.: US 10,669,235 B2
(45) Date of Patent: Jun. 2, 2020

(54) INDOLE DERIVATIVES AND THEIR USE AS PROTEIN KINASE INHIBITORS

(71) Applicant: RESPIVERT LIMITED, High Wycombe (GB)

(72) Inventors: Iain Walters, Nottingham (GB); Louise Birch, Nottingham (GB); Stephen Paul Collingwood, High Wycombe (GB); Christopher Scott Stevenson, High Wycombe (GB)

(73) Assignee: RESPIVERT LIMITED, High Wycombe (GB)

( * ) Notice: Subject to any disclaimer, the term of this patent is extended or adjusted under 35 U.S.C. 154(b) by 0 days.

(21) Appl. No.: 16/083,886

(22) PCT Filed: Mar. 8, 2017

(86) PCT No.: PCT/GB2017/050619
§ 371 (c)(1),
(2) Date: Sep. 10, 2018

(87) PCT Pub. No.: WO2017/153748
PCT Pub. Date: Sep. 14, 2017

(65) Prior Publication Data
US 2019/0071399 A1 Mar. 7, 2019

(30) Foreign Application Priority Data
Mar. 8, 2016 (EP) .................... 16159231

(51) Int. Cl.
| | | |
|---|---|---|
| C07D 209/34 | (2006.01) |
| A61K 31/635 | (2006.01) |
| A61K 31/4045 | (2006.01) |
| C07D 401/12 | (2006.01) |
| A61K 31/454 | (2006.01) |
| A61K 31/551 | (2006.01) |
| C07D 403/12 | (2006.01) |
| A61K 31/5377 | (2006.01) |
| C07D 471/10 | (2006.01) |
| A61K 31/527 | (2006.01) |
| C07D 405/12 | (2006.01) |
| A61K 31/541 | (2006.01) |
| A61K 31/496 | (2006.01) |
| A61K 31/4412 | (2006.01) |
| A61P 11/00 | (2006.01) |
| C07D 295/145 | (2006.01) |
| C07C 205/57 | (2006.01) |

(52) U.S. Cl.
CPC ........ *C07D 209/34* (2013.01); *A61K 31/4045* (2013.01); *A61K 31/4412* (2013.01); *A61K 31/454* (2013.01); *A61K 31/496* (2013.01); *A61K 31/527* (2013.01); *A61K 31/5377* (2013.01); *A61K 31/541* (2013.01); *A61K 31/551* (2013.01); *A61K 31/635* (2013.01); *A61P 11/00* (2018.01); *C07C 205/57* (2013.01); *C07D 295/145* (2013.01); *C07D 401/12* (2013.01); *C07D 403/12* (2013.01); *C07D 405/12* (2013.01); *C07D 471/10* (2013.01)

(58) Field of Classification Search
CPC .............. C07D 209/34; C07D 295/145; C07D 401/12; C07D 403/12; C07D 405/12; C07D 471/10; A61P 11/00; A61K 31/4045; A61K 31/4412; A61K 31/454; A61K 31/496; A61K 31/527; A61K 31/5377; A61K 31/541; A61K 31/551; A61K 31/635; C07C 205/57
USPC ....................................................... 514/157
See application file for complete search history.

(56) References Cited

FOREIGN PATENT DOCUMENTS

| | | |
|---|---|---|
| WO | WO 02/081445 A1 | 10/2002 |
| WO | WO 2006/067168 A1 | 6/2006 |
| WO | WO 2017/109513 | 6/2017 |

OTHER PUBLICATIONS

Roth, et al., "Design, Synthesis, and Evaluation of Indolinones as Triple Angiokinase Inhibitors and the Discovery of a Highly Specific 6-Methoxycarbonyl-Substituted Indolinone (BIBF 1120)," *J. Med. Chem* 52:4466-4480 (2009).
International Search Report from International Application No. PCT/GB2017/050619, dated Apr. 20, 2017.

*Primary Examiner* — Kristin A Vajda
(74) *Attorney, Agent, or Firm* — Morse, Barnes-Brown & Pendleton, P.C.; Lisa M. Warren, Esq.

(57) ABSTRACT

The present invention relates inter alia to a compound of formula (I) wherein $R_1$, $R_2$ and $R_3$, are as defined in the specification and to compositions comprising the same and to the use of the compounds and to compositions of the compounds in treatment, for example in the treatment of fibrotic diseases or interstitial lung diseases, in particular idiopathic pulmonary fibrosis.

13 Claims, 2 Drawing Sheets

INDOLE DERIVATIVES AND THEIR USE AS PROTEIN KINASE INHIBITORS

This application is a national stage filing under 35 U.S.C. 371 of International Application No. PCT/GB2017/050619, filed Mar. 8, 2017, which claims priority to European Application No. 16159231.6, filed Mar. 8, 2016. The entire teachings of PCT/GB2017/050619 are incorporated herein by reference.

FIELD OF THE INVENTION

The invention relates inter alia to novel compounds which inhibit protein kinases and to their use in therapy, particularly for the treatment of fibrotic diseases or interstitial lung diseases, especially Idiopathic Pulmonary Fibrosis and respiratory diseases. The invention also extends to pharmaceutical compositions comprising the compounds.

BACKGROUND OF THE INVENTION

Interstitial lung diseases (ILDs) are characterized by scarring of the lung that leads to lung dysfunction, which can eventually lead to respiratory failure. There are many ILDs with no known cause, which are termed idiopathic. Idiopathic Pulmonary Fibrosis (IPF) is the most common type of ILD. IPF affects about 170,000 people in Europe and 130,000 people in the United States, with approximately 48,000 new cases diagnosed each year in the US alone and 40,000 people dying in the US annually. IPF mortality rates are very high with median survival of 3-5 years from diagnosis and reported 5-year survival rates of less than 30%, on a par with the most lethal cancers. Until recently few treatment options other than lung transplantation have been shown to be effective and treatment for most patients has been symptom control and palliative care.

IPF is a chronic and fatal disease primarily characterised by a progressive decline in lung function caused by the scarring of lung tissue which results in worsening dyspnea. Vascular endothelial growth factor (VEGF), fibroblast growth factor (FGF) and platelet derived growth factor (PDGF) are known potent mitogens for fibroblast cells, which then replace the normal tissue in lungs when fibrosis occurs. In ILDs, the evidence for a pathogenic role for PDGF, VEGF, and FGF has been demonstrated clinically. The primary site affected is the interstitium, the tissue between the air sacs in the lung, but it does also affect the airspaces, peripheral airways and vessels. The disease process is believed to be initiated by a series of microinjuries to the alveolar epithelium in the lung. After the injury, increased vascular permeability leads to clot formation and resident epithelial cells proliferate in an attempt to replace those cells that died as a result of the injury. This process triggers the release of a variety of growth factors (eg, PDGF, VEGF, FGF, and transforming growth factor β (TGFβ), leading to the aberrant activation of the epithelial cells, abnormal vascular remodelling, and most notably, the proliferation and migration of fibroblasts into the lung. Growth factors also induce resident cells to transform into myofibroblasts, which together with fibroblasts organize into foci (King T E Jr, et al., Lancet, 2011, 3; 378(9807):1949-61; Selman M, et al., Ann Intern Med., 2001, 16; 134(2):136-51). These cellular changes result in the disruption of the basement membrane and excessive accumulation of extracellular matrix proteins in the interstitial space. The result is the eventual destruction of the normal architecture of the alveolar capillary unit and lung scarring. The pathologies that define the usual interstitial pattern (UIP) of fibrosis characteristic of IPF are a heterogeneous pattern of alternating areas of normal lung, interstitial inflammation, dense fibrosis, fibroblastic foci, and honeycombing, especially in the subpleural area of the lung (Du Bois R M., Nat Rev Drug Discov., 2010, 9(2):129-40; Selman M, et al., Ann Intern Med., 2001, 16; 134(2):136-51; King T E Jr, et al., Lancet, 2011, 3; 378(9807):1949-61). The loss of normal architecture and scarring of the interstitial space leads to a significant decline in gas exchange capacity leading to development of the classical symptoms of the disease namely dyspnea, chronic cough, inspiratory crackles on auscultation, and abnormal spirometry (Castriotta R J, et al., Chest, 2010, 138(3):693-703). While the disease course is heterogeneous, the median survival is approximately 3-5 years and the most common cause of death is respiratory failure due to the progressive pathologies that disrupt normal lung functioning and gas-exchange.

To achieve better tolerability and also better efficacy in treatment of lung disorders it can be advantageous to deliver a drug directly to the site of action in the lung. This enables higher concentrations of drug to be achieved at the site of action resulting in a lower overall dose consequently lowering systemic side effects.

Nintedanib, a protein kinase inhibitor, was approved by the FDA for treatment of IPF in 2014 by oral administration. However, it is associated with significant systemic adverse events, including abdominal pain, vomiting and diarrhoea. WO2006/067165 teaches that inhibitors of VEGFR, FGFR and PDGFR, such as nintedanib, may be expected to be useful in treatment of fibrotic diseases, such as IPF. Fehrenbach, H., et al., Virchows Arch., 1999, 435(1):20-31 discloses that VEGFR is linked to the cause of pulmonary fibrosis. Lindroos. P., Am J Physio Lung Cell Mol Physiol., 2001, 280:L354-L362 teaches that the upregulation of PDGF receptor is a mechanism of myofibroblast hyperplasia during pulmonary fibrosis. WO01/27081 shows that compounds that have inhibiting effects on kinases, including VEGFR, PDGFR and FGFR, are suitable for treating fibrotic diseases and discloses a series of 6-position substituted indolinones. Similarly, WO2006/067165 and WO2006/067168 also disclose 6-position substituted indolinones for use as medicaments for the treatment or prevention of fibrotic diseases.

There remains a need in the art to develop further compounds, especially compounds that are better tolerated than nintedanib, for treating fibrotic diseases and interstitial lung diseases, such as IPF. Desirably such compounds would have low dose, long duration of action suitable for once, twice or three times daily dosing and good efficacy and tolerability especially when delivered topically to the lung. The compounds of formula (I) described herein address this issue.

SUMMARY OF THE INVENTION

According to the invention, there is provided a compound of formula (I):

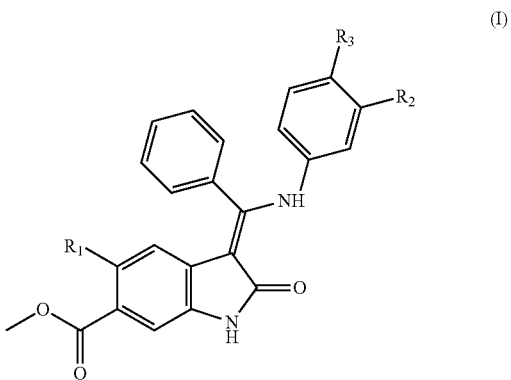

wherein
R$_1$ represents Me, Et, CH=CH$_2$, C≡C—H or C≡C-Me;
one of R$_2$ and R$_3$ represents a group selected from H, —C$_1$-C$_6$alkoxy, —C$_3$-C$_8$cycloalkyl, —CH$_2$—(C$_3$-C$_8$cycloalkyl), halogen and cyano, and the other represents the group —Z—R$_x$;
R$_x$ represents

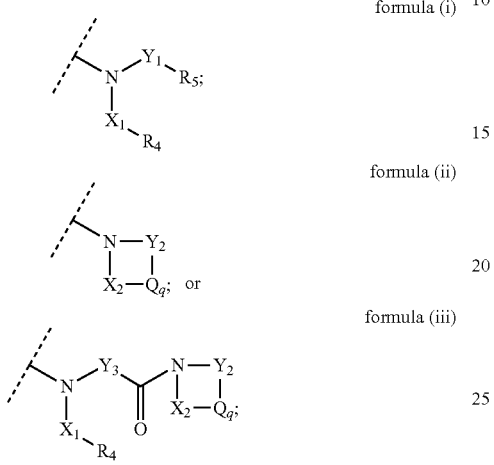

formula (i)

formula (ii)

formula (iii)

Z represents CO or SO$_2$;
Y$_1$ represents (CH$_2$)$_n$ and, except when n represents 0, may optionally be substituted by Me;
X$_1$ represents (CH$_2$)$_m$ and, except when m represents 0, may optionally be substituted by Me;
n and m independently represent 0, 1, 2, 3, 4 or 5;
Y$_2$ represents (CH$_2$)$_s$ and may optionally be substituted on the same or different carbon atoms by one or more groups selected from Me, OH, —C$_0$-C$_4$alkyleneCONR$_6$R$_7$, —C$_0$-C$_4$alkyleneNR$_6$COR$_7$, —C$_1$-C$_4$hydroxyalkyl, —C$_1$-C$_4$alkylNR$_8$R$_9$ and —C$_0$-C$_4$alkyl-Het;
X$_2$ represents (CH$_2$)$_v$ and may optionally be substituted on the same or different carbon atoms by one or more groups selected from Me, OH, —C$_0$-C$_4$alkyleneCONR$_{10}$R$_{11}$, —C$_0$-C$_4$alkyleneNR$_{10}$COR$_{11}$, —C$_1$-C$_4$hydroxyalkyl, —C$_1$-C$_4$alkylNR$_{12}$R$_{13}$ and —C$_0$-C$_4$alkyl-Het;
Q represents spiro-C or a heteroatom selected from N, O and S and if N may optionally be substituted with one or more groups selected from —C$_1$-C$_4$alkyl, —C$_1$-C$_4$hydroxyalkyl, —C$_2$-C$_4$alkylNR$_{12}$R$_{13}$, —C$_0$-C$_4$alkyl-Het, —C$_1$-C$_4$alkyleneCONR$_{14}$R$_{15}$ and —C$_2$-C$_4$alkyleneNR$_{14}$COR$_{15}$;
Het represents a 4-8 membered aliphatic heterocycle containing one or more heteroatoms independently selected from N, O and S, optionally containing a carbonyl group and optionally substituted by one or more Me groups;
q represents 0 or 1;
s and v independently represent 2 or 3 save that s+v+q=3, 4, 5, 6 or 7;
spiro-C is a quaternary carbon atom which joins a 4-8 membered aliphatic heterocycle containing one or more heteroatoms independently selected from N, O and S, optionally containing a carbonyl group and optionally substituted by one or more Me groups, to the heterocycle comprising N, X$_2$ and Y$_2$;

Y$_3$ represents (CH$_2$)$_t$;
t represents 1, 2, 3 or 4;
R$_4$ represents H, OH, NR$_{16}$R$_{17}$, C$_3$-C$_5$cycloalkyl or a 4-8 membered aliphatic heterocycle containing one or more heteroatoms independently selected from N, O and S, save that when R$_4$ is OH or NR$_{16}$R$_{17}$, m is 2, 3, 4 or 5;
R$_5$ represents H, OH, NR$_{18}$R$_{19}$, C$_3$-C$_5$cycloalkyl or a 4-8 membered aliphatic heterocycle containing one or more heteroatoms independently selected from N, O and S, save that when R$_5$ is OH or NR$_{18}$R$_{19}$, n is 2, 3, 4 or 5;
in which the aliphatic heterocycle groups that R$_4$ and R$_5$ may represent may optionally contain a carbonyl or sulphone group and the C$_3$-C$_5$cycloalkyl and the aliphatic heterocycle groups that R$_4$ and R$_5$ may represent may optionally be substituted by one or more groups selected from —C$_1$-C$_4$alkyl, —C$_1$-C$_4$hydroxyalkyl, C$_1$-C$_4$alkoxy(C$_1$-C$_4$)alkyl-, —C$_1$-C$_4$alkyleneCONR$_{20}$R$_{21}$, —C$_1$-C$_4$alkyleneNR$_{20}$COR$_{21}$, —SO$_2$(C$_1$-C$_4$)alkyl, —CO(C$_1$-C$_4$)alkyl, halogen, CN, OH and NR$_{22}$R$_{23}$;
R$_6$, R$_7$, R$_{10}$, R$_{11}$, R$_{14}$ and R$_{15}$ independently represent H, —C$_1$-C$_4$alkyl, —C$_1$-C$_4$hydroxyalkyl, C$_1$-C$_4$alkoxy(C$_1$-C$_4$)alkyl- or —C$_1$-C$_4$alkylN(C$_1$-C$_4$alkyl)$_2$;
R$_{16}$, R$_{17}$, R$_{18}$, R$_{19}$ independently represent H, or —C$_1$-C$_4$alkyl optionally substituted by one or more groups selected from OH, oxo, NR$_{24}$R$_{25}$ and C$_1$-C$_4$alkoxy-; and
R$_8$, R$_9$, R$_{12}$, R$_{13}$, R$_{20}$, R$_{21}$, R$_{22}$, R$_{23}$, R$_{24}$ and R$_{25}$ independently represent H or —C$_1$-C$_4$alkyl; or a pharmaceutically acceptable salt thereof (hereinafter "compounds of the invention" or "a compound of the invention").

DETAILED DESCRIPTION OF THE INVENTION

Figure 1:
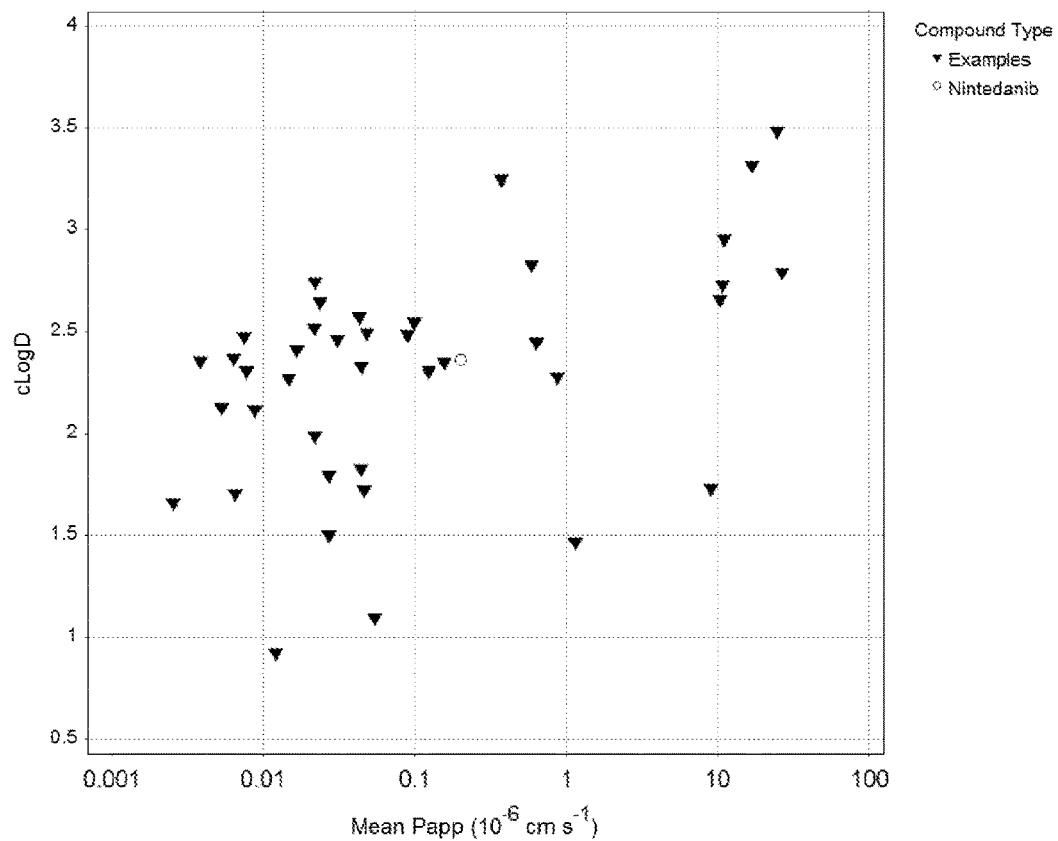
FIG. 1: shows the artificial membrane permeability of representative examples (3-12, 17-22, 25-27, 29-40, 43-49) of the invention and nintedanib (see results of PAMPA permeability assay and Table 7: average values were used for compounds where the experiment was repeated)

Alkyl groups may be branched or straight chain. C$_{1-8}$alkyl groups may for example represent C$_{1-6}$alkyl or C$_{1-4}$alkyl. Exemplary alkyl groups include methyl, ethyl, n-propyl, i-propyl, n-butyl, t-butyl and CH$_2$CHMe$_2$. In one embodiment alkyl refers to straight chain alkyl. Alkylene is to be construed in the same way as alkyl except that it is a divalent group.

Alkoxy as used herein means —Oalkyl and includes straight or branched chain alkoxy, for example methoxy, ethoxy, propoxy, butoxy.

Hydroxyalkyl means alkyl with a hydroxyl substituent in any position. Examples include hydroxymethyl, 2-hydroxyethyl, 3-hydroxy-n-propyl and 4-hydroxy-n-butyl.

Halogens may suitably be Br, Cl or F, especially Cl or F, particularly F.

Examples of 4-8 membered aliphatic heterocyclic rings containing one or more heteroatoms independently selected from N, O and S include azetidine, pyrrolidine, piperidine, piperazine, morpholine, dioxane, tetrahydrofuran, thiomorpholine, tetrahydropyran and diazepane. Suitably the heterocyclic ring includes 1 or 2, especially 1 heteroatom. Such rings may contain a carbonyl and examples include pyrrolidinone, piperazinone, diazepanone and piperidinone. Such rings that $R_4$ and $R_5$ may represent may contain a sulphone group such as 1,1-dioxo-1-thiomorpholin-1-yl.

$C_3$-$C_8$cycloalkyl refers to an aliphatic carbocyclic ring containing typically 3 to 8 ring members with optional branching and containing 3 to 8 carbon atoms in total. Examples include cyclopropyl, cyclobutyl, cyclopentyl, cyclohexyl, methylcyclohexyl, cycloheptyl and cyclooctyl. In one embodiment the rings are not substituted. In another embodiment the ring bears one substituent, for example, dimethylamino. Example of a substituted cycloalkyl ring is 1-(dimethylamino)cyclobutyl.

4-8 membered aliphatic heterocyclic rings may optionally be substituted. In one embodiment the rings are not substituted. In another embodiment the ring bears one substituent. In another embodiment the ring bears two substituents. A substituent may be on a carbon or a nitrogen atom. Such rings that Het may represent or fall within the definition of spiro-C may be substituted by methyl. Examples include morpholinomethyl, pyrrolidin-1-ylmethyl, 4-methyl-1,4-diazepan-2-one and 4-methylpiperazin-2-one.

Such examples of substituted heterocyclic rings that $R_4$ and $R_5$ may represent include 1-methyl-piperazine, 1-methyl-piperidine, 1-methyl-1,4-diazepane, 4-dimethylamino-piperidine, 4-hydroxy-piperidine, 1-(2-hydroxyethyl)piperidine, 4-(hydroxymethyl)piperidine, 1-(2-methoxyethyl)piperidine, 4,4-difluoropiperidine, 4-fluoropiperidine, 1-acetylpiperazine, 4-methyl-1,4-diazepan-2-one, 1-acetyl-1,4-diazepane, 4-(dimethylamino)tetrahydro-2H-pyran, 4-(methylsulfonyl)piperazine and 3-hydroxy-1-methylpyrrolidine.

Spiro-C refers to a quaternary carbon atom connecting two aliphatic heterocyclic rings together per the definition above to form a spiro bicyclic ring. Examples of spiro bicyclic rings include spiro[5.5]undecane and spiro[5.6]dodecane. Examples of substituted spiro bicyclic rings include 1-methyl-5-oxo-1,4,9-triazaspiro[5.5]undecane and 7-methyl-12-oxo-3,7,11-triazaspiro[5.6]dodecane.

In one embodiment there is provided a pharmaceutically acceptable salt of the compound of the invention.

The compounds of the disclosure include those where the atom specified is a naturally occurring or non-naturally occurring isotope. In one embodiment the isotope is a stable isotope.

Thus the compounds of the disclosure include, for example those containing one or more deuterium atoms in place of hydrogen atoms and the like.

The disclosure also extends to all polymorphic forms of the compounds herein defined including salts thereof.

The disclosure also extends to all solvates of the compounds herein defined. Examples of solvates include hydrates.

Suitably $R_1$ represents Me.

In a preferred embodiment $R_2$ represents a group selected from H, —$C_1$-$C_6$alkyl, $C_1$-$C_6$alkoxy-, $C_3$-$C_8$cycloalkyl-, —$CH_2$—($C_3$-$C_8$cycloalkyl), halogen and cyano and $R_3$ represents the group —Z—$R_x$. In an alternative embodiment $R_2$ represents the group —Z—$R_x$ and $R_3$ represents a group selected from H, —$C_1$-$C_6$alkyl, $C_1$-$C_6$alkoxy-, —$C_3$-$C_8$cycloalkyl, —$CH_2$—($C_3$-$C_8$cycloalkyl), halogen and cyano.

Suitably when $R_2$ or $R_3$ do not represent —Z—$R_x$, they represent a group selected from H, $C_1$-$C_6$alkyl, $C_1$-$C_6$alkoxy-, $C_3$-$C_6$cycloalkyl, halogen and cyano, more suitably H, $C_1$-$C_4$alkyl or halogen, yet more suitably H, Me or halogen, most suitably H, Me or F, especially H.

In a preferred embodiment Z represents CO. In an alternative embodiment Z is $SO_2$.

In one preferred embodiment $R_x$ represents formula (i).

Suitably $R_4$ represents $NR_{16}R_{17}$, m is 2, 3, 4 or 5 and $R_5$ represents H or OH save that when $R_5$ is OH, n is 2, 3, 4 or 5.

Alternatively suitably $R_4$ represents an N-linked 4-8 membered aliphatic heterocycle containing an N and optionally containing a further one or more heteroatoms selected from N, O and S, m is 2, 3, 4 or 5 and $R_5$ represents H or OH save that when $R_5$ is OH, n is 2, 3, 4 or 5.

Suitably $R_5$ represents $NR_{18}R_{19}$, n is 2, 3, 4 or 5 and $R_4$ represents H or OH save that when $R_4$ is OH, m is 2, 3, 4 or 5.

Alternatively suitably $R_5$ represents an N-linked 4-8 membered aliphatic heterocycle containing an N and optionally containing a further one or more heteroatoms selected from N, O and S, n is 2, 3, 4 or 5 and $R_4$ represents H or OH save that when $R_4$ is OH, m is 2, 3, 4 or 5.

Suitably $X_1$ represents $(CH_2)_m$.

Suitably $X_1$ represents $(CH_2)_0$, $CH_2$ or $(CH_2)_2$, especially $(CH_2)_0$ or $CH_2$, preferably $(CH_2)_0$.

Suitably $R_4$ represents H or OH, especially H.

Suitably moiety —$X_1$—$R_4$ represents H, Me or 2-hydroxyethyl, especially H or Me, preferably H.

Suitably $Y_1$ represents $(CH_2)_n$.

Suitably $Y_1$ represents $(CH_2)_0$, $CH_2$, $(CH_2)_2$ or $(CH_2)_3$, especially $(CH_2)_2$ or $(CH_2)_0$, preferably $(CH_2)_2$.

Suitably $R_5$ represents 1-methyl-piperazinyl, dimethylamino, 1-methyl-piperidinyl, 1-methyl-1,4-diazepanyl, 4-dimethylamino-piperidinyl, piperazinonyl, 4-hydroxy-piperidinyl, 1-(2-hydroxyethyl)piperidinyl, 1-(2-methoxyethyl)piperidinyl, 4,4-difluoropiperidinyl, 1-acetylpiperazinyl, 4-fluoropiperidinyl, morpholinyl, 1-acetyl-1,4-diazepanyl, (2-methoxyethyl)(methyl)amino, 4-(dimethylamino)tetrahydro-2H-pyran, 1-(dimethylamino)cyclobutyl, 4-(hydroxymethyl)piperidinyl, 4-(methylsulfonyl)piperazinyl, 4-(methylsulfonyl)piperazinyl, 3-hydroxy-1-methylpyrrolidinyl, (2-hydroxyethyl)(methyl)amino, 1,1-dioxidothiomorpholino, 5-oxo-1,4-diazepanyl, methyl(2-(methylamino)-2-oxoethyl)amino, or 3-oxo-1,4-diazepanyl, especially 4-hydroxy-piperidinyl, 1-methyl-piperazinyl, 5-oxo-1,4-diazepanyl, 1-methyl-piperidinyl, 1-methyl-1,4-diazepanyl, 4-dimethylamino-piperdinyl, piperazinonyl or 1-(2-hydroxyethyl)piperidinyl, preferably 1-methyl-piperazinyl, 1-methyl-piperidinyl, 1-methyl-1,4-diazepanyl, 4-dimethylamino-piperdinyl, piperazinonyl or 1-(2-hydroxyethyl)piperidinyl.

Suitably moiety —$Y_1$—$R_5$ represents —$(CH_2)_2$-(4-methyl)-piperazin-1-yl, —$(CH_2)_2$-dimethylamino, —$(CH_2)$-(1-methyl)-piperidin-4-yl, —$(CH_2)_2$-(4-methyl)-piperazin-1-yl, —$(CH_2)_2$-(4-methyl-1,4-diazepan-1-yl), —$(CH_2)_2$-4-dimethylamino-piperidin-1-yl, —$(CH_2)_2$-3-oxopiperazin-1-yl, —$(CH_2)_2$-(4-hydroxy-piperidin-1-yl), -1-(2-hydroxyethyl)piperidin-4-yl, —$(CH_2)$-1-(2-hydroxyethyl)piperidin-4-yl, -1-methylpiperidin-4-yl, -1-(2-methoxyethyl)piperidin-4-yl, —$(CH_2)_3$-4-methyl-piperazin-1-yl, —$(CH_2)_3$-dimethylamino, —$(CH_2)_2$-4,4-difluoropiperidin-1-yl), —$(CH_2)_2$-4-acetylpiperazin-1-yl, -1-methyl-piperidin-3-yl, —(CH$_2$)$_2$-4-fluoro-piperidin-1-yl, —(CH$_2$)$_3$-morpholin-4-yl, —(CH$_2$)$_2$-4-acetyl-1,4-diazepan-1-yl, —(CH$_2$)$_2$-((2-methoxyethyl)(methyl)amino), —CH$_2$-(4-(dimethylamino)tetrahydro-2H-pyran-4-yl), —CH$_2$-(1-(dimethylamino)cyclobutyl), -1-(2-hydroxyethyl)piperidin-4-yl, —(CH$_2$)$_2$-(4-(hydroxymethyl)piperidin-1-yl), —(CH$_2$)$_2$-(4-(methylsulfonyl)piperazin-1-yl), 4-hydroxy-1-methylpyrrolidin-3-yl, —(CH$_2$)$_2$-(2-hydroxyethyl)(methyl)amino, —(CH$_2$)$_2$-1,1-dioxidothiomorpholino, —(CH$_2$)$_2$-(5-oxo-1,4-diazepan-1-yl), —(CH$_2$)$_2$-(methyl(2-(methylamino)-2-oxoethyl)amino), —(CH$_2$)$_2$-(3-oxo-1,4-diazepan-1-yl), especially —(CH$_2$)$_2$-(4-hydroxy-piperidin-1-yl), -1-(2-hydroxyethyl)piperidin-4-yl, —(CH$_2$)-1-(2-hydroxyethyl)piperidin-4-yl, —(CH$_2$)$_2$-(5-oxo-1,4-diazepan-1-yl), —(CH$_2$)$_2$-(4-methyl)-piperazin-1-yl, —(CH$_2$)$_2$-(4-methyl-1,4-diazepan-1-yl), —(CH$_2$)$_2$-(4-dimethylamino-piperdin-1-yl), —(CH$_2$)$_2$-3-oxopiperazin-1-yl, -1-methylpiperidin-4-yl, preferably —(CH$_2$)$_2$-(4-methyl)-piperazin-1-yl, —(CH$_2$)$_2$-(4-methyl-1,4-diazepan-1-yl), —(CH$_2$)$_2$-(4-dimethylamino-piperdin-1-yl), —(CH$_2$)$_2$-3-oxopiperazin-1-yl, -1-methylpiperidin-4-yl.

Suitably formula (i) represents a moiety in which: (a) —X$_1$—R$_4$ represents H and —Y$_1$—R$_5$ represents —(CH$_2$)$_2$-(4-methyl)-piperazin-1-yl, —(CH$_2$)$_2$-dimethylamino, —(CH$_2$)-(1-methyl)-piperidin-4-yl, —(CH$_2$)$_2$-(4-methyl)-piperazin-1-yl, —(CH$_2$)$_2$-(4-methyl-1,4-diazepan-1-yl), —(CH$_2$)$_2$-4-dimethylamino-piperidin-1-yl, —(CH$_2$)$_2$-3-oxopiperazin-1-yl, —(CH$_2$)$_2$-(4-hydroxy-piperidin-1-yl), -1-(2-hydroxyethyl)piperidin-4-yl, —(CH$_2$)-1-(2-hydroxyethyl)piperidin-4-yl, -1-methylpiperidin-4-yl, -1-(2-methoxyethyl)piperidin-4-yl, —(CH$_2$)$_3$-4-methyl-piperazin-1-yl, —(CH$_2$)$_3$-dimethylamino, —(CH$_2$)$_2$-4,4-difluoro-piperidin-1-yl), —(CH$_2$)$_2$-4-acetylpiperazin-1-yl, -1-methyl-piperidin-3-yl, —(CH$_2$)$_2$-4-fluoro-piperidin-1-yl, —(CH$_2$)$_3$-morpholin-4-yl, —(CH$_2$)$_2$-4-acetyl-1,4-diazepan-1-yl, —(CH$_2$)$_2$-((2-methoxyethyl)(methyl)amino), —CH$_2$-(4-(dimethylamino)tetrahydro-2H-pyran-4-yl), —CH$_2$-(1-(dimethylamino)cyclobutyl), —(CH$_2$)$_2$-(4-(hydroxymethyl)piperidin-1-yl), —(CH$_2$)$_2$-(4-(methylsulfonyl)piperazin-1-yl), —(CH$_2$)$_2$-(2-hydroxyethyl)(methyl)amino, —(CH$_2$)$_2$-1,1-dioxidothiomorpholino, —(CH$_2$)$_2$-(5-oxo-1,4-diazepan-1-yl), —(CH$_2$)$_2$-(methyl(2-(methylamino)-2-oxoethyl)amino) or —(CH$_2$)$_2$-(3-oxo-1,4-diazepan-1-yl), especially —X$_1$—R$_4$ represents H and —Y$_1$—R$_5$ represents —(CH$_2$)$_2$-(4-hydroxy-piperidin-1-yl), -1-(2-hydroxyethyl)piperidin-4-yl, —(CH$_2$)-1-(2-hydroxyethyl)piperidin-4-yl, —(CH$_2$)$_2$-(5-oxo-1,4-diazepan-1-yl), —(CH$_2$)$_2$-(4-methyl)-piperazin-1-yl, —(CH$_2$)$_2$-(4-methyl-1,4-diazepan-1-yl), —(CH$_2$)$_2$-(4-dimethylamino-piperdin-1-yl), —(CH$_2$)$_2$-3-oxopiperazin-1-yl, -1-methylpiperidin-4-yl, preferably —X$_1$—R$_4$ represents H and —Y$_1$—R$_5$ represents —(CH$_2$)$_2$-(4-methyl)-piperazin-1-yl, —(CH$_2$)$_2$-(4-methyl-1,4-diazepan-1-yl), —(CH$_2$)$_2$-(4-dimethylamino-piperdin-1-yl), —(CH$_2$)$_2$-3-oxopiperazin-1-yl, -1-methylpiperidin-4-yl; or (b) —X$_1$—R$_4$ represents Me and —Y$_1$—R$_5$ represents —(CH$_2$)$_2$-dimethylamino, -1-(2-hydroxyethyl)piperidin-4-yl or 4-hydroxy-1-methylpyrrolidin-3-yl, especially —X$_1$—R$_4$ represents Me and —Y$_1$—R$_5$ represents —(CH$_2$)$_2$-dimethylamino; or (c) —X$_1$—R$_4$ represents 2-hydroxyethyl and —Y$_1$—R$_5$ represents —(CH$_2$)$_2$-dimethylamino. The moiety of formula (i) is preferably represented by (a).

In one embodiment R$_x$ represents formula (ii).
Suitably Y$_2$ represents (CH$_2$)$_s$.
Suitably s is 2, 3, or 4, more suitably 2 or 3 especially 2.
In an embodiment Y$_2$ is not substituted. In an embodiment Y$_2$ is substituted by one group. In an embodiment Y$_2$ is substituted by two groups, for example on the same carbon atom.
Suitably X$_2$ represents (CH$_2$)$_v$.
Suitably v is 2, 3, or 4, more suitably 2 or 3 especially 2.
In an embodiment X$_2$ is not substituted. In an embodiment X$_2$ is substituted by one group. In an embodiment X$_2$ is substituted by two groups, for example on the same carbon atom.
Suitably Q is N, O or C, especially N.
Suitably q is 0 or 1, especially 1.
Suitably s is 2, v is 2 and q is 1, or s is 3, v is 2 and q is 0, or s is 2, v is 3 and q is 1, especially s is 2, v is 2 and q is 1, or s is 3, v is 2, preferably s is 2, v is 2 and q is 1.

In one embodiment formula (ii) bears zero substituents i.e. none of X$_2$, Y$_2$ and Q are substituted. In one embodiment formula (ii) bears one substituent i.e. either X$_2$, Y$_2$ or Q is substituted once. In another embodiment formula (ii) bears two substituents which may be substituted at the same position on the ring or at different positions on the ring i.e. X$_2$, Y$_2$ and/or Q is/are substituted so there are two substitutions in total. A substituent may be on a carbon or a nitrogen atom.

Suitable substituents are selected from Me, OH, F, acetyl, dimethylamino, 2-hydroxyethyl, hydroxymethyl, 2-(methylamino)-2-oxoethyl, 2-methoxyethyl, 2-(dimethylamino)ethyl)carbamoyl, —CH$_2$-dimethylamino, pyrrolidin-1-ylmethyl, 2-((2-methoxyethyl)amino)-2-oxoethyl, methylsulfonyl, morpholinomethyl, piperidinyl, —CONH$_2$ and 2-((2-hydroxyethyl)amino)-2-oxoethyl, especially selected from Me, dimethylamino and 2-hydroxymethyl, preferably Me.

Suitably Het is substituted by one or two Me groups, such as one Me group. Alternatively, Het is not substituted by Me groups.

Suitably formula (ii) represents 4-(2-(methylamino)-2-oxoethyl)piperazin-1yl, 4-methylpiperazin-1-yl, 4-(2-hydroxyethyl)piperazin-1-yl, 4-(1-methyl-5-oxo-1,4,9-triazaspiro[5.5]undecan-9-yl, 4-((2-(dimethylamino)ethyl)carbamoyl)piperidin-1-yl, 4-((dimethylamino)methyl)-3-hydroxypiperidin-1-yl, 4-hydroxy-4-(pyrrolidin-1-ylmethyl)piperidin-1-yl, 4-((dimethylamino)methyl)-4-(hydroxymethyl)piperidin-1-yl, 4-(2-((2-methoxyethyl)amino)-2-oxoethyl)piperazin-1-yl, 7-methyl-12-oxo-3,7,11-triazaspiro[5.6]dodecan-3-yl, 4-hydroxy-4-(morpholinomethyl)piperidin-1-yl, 4-(2-hydroxyethyl)-1,4-diazepan-1-yl, 4'-carbamoyl-[1,4'-bipiperidin-1'-yl], 4-(2-((2-hydroxyethyl)amino)-2-oxoethyl)piperazin-1-yl, especially 4'-carbamoyl-[1,4'-bipiperidin-1'-yl], 4-methylpiperazin-1-yl or 4-(2-hydroxyethyl)piperazin-1-yl, preferably 4'-carbamoyl-[1,4'-bipiperidin-1'-yl].

In one embodiment R$_x$ represents formula (iii).
Suitably Y$_3$ represents (CH$_2$)$_t$.
Suitably t represents 1, 2, 3 or 4, especially 1 or 2, more suitably 1;
Suitably formula (iii) represents 2-(4-(2-hydroxyethyl)piperazin-1-yl)-2-oxoethyl)amino, 2-(4-methylpiperazin-1-yl)-2-oxoethyl)amino or 3-(4-methylpiperazin-1-yl)-3-oxopropyl)amino, especially 2-(4-(2-hydroxyethyl)piperazin-1-yl)-2-oxoethyl)amino or 3-(4-methylpiperazin-1-yl)-3-oxopropyl)amino, preferably 2-(4-(2-hydroxyethyl)piperazin-1-yl)-2-oxoethyl)amino.

Suitably R$_6$, R$_7$, R$_{10}$ and R$_{11}$ independently represent H, —C$_1$-C$_4$alkyl or —C$_1$-C$_4$alkylN(C$_1$-C$_4$alkyl)$_2$.

Suitably $R_{14}$ and $R_{15}$ independently represent H, —$C_1$-$C_4$alkyl, —$C_1$-$C_4$hydroxyalkyl or $C_1$-$C_4$alkoxy($C_1$-$C_4$)alkyl-.

Suitably $R_6$ represents —$C_1$-$C_4$alkylN($C_1$-$C_4$alkyl)$_2$, for example —(CH$_2$)$_2$NMe$_2$. Alternatively suitably $R_6$ represents H or —$C_1$-$C_4$alkyl, especially H.

Suitably $R_7$, $R_{10}$ and $R_{11}$ independently represent H or $C_1$-$C_4$alkyl, especially H.

Suitably $R_{14}$ represents $C_1$-$C_4$alkoxy($C_1$-$C_4$)alkyl-, for example —(CH$_2$)$_2$OMe, or —$C_1$-$C_4$hydroxyalkyl, e.g. 2-hydroxyethyl.

Suitably $R_{14}$ and $R_{15}$ independently represent H or —$C_1$-$C_4$alkyl, especially H.

Suitably $R_{16}$, $R_{17}$, $R_{18}$ and $R_{19}$ independently represent —$C_1$-$C_4$alkyl optionally substituted by one or two groups, such as one group, selected from OH, oxo, NR$_{24}$R$_{25}$ and $C_1$-$C_4$alkoxy-.

Suitably $R_{16}$ represents Me or 2-methoxyethyl, preferably Me.

Suitably $R_{17}$ represents Me.

Suitably $R_{18}$ represents Me.

Suitably $R_{19}$ represents Me, 2-hydroxyethyl or 2-(methylamino)-2-oxoethyl, especially Me.

In an embodiment, $R_{16}$ represents H.

In an embodiment, $R_{17}$ represents H.

In an embodiment, $R_{18}$ represents H.

In an embodiment, $R_{19}$ represents H.

Suitably $R_8$, $R_9$, $R_{12}$, $R_{13}$, $R_{20}$, $R_{21}$, $R_{22}$, $R_{23}$, $R_{24}$ and $R_{25}$ are independently selected from H and Me. In one embodiment $R_8$, $R_9$, $R_{12}$, $R_{13}$, $R_{20}$, $R_{21}$, $R_{22}$, $R_{23}$, $R_{24}$ and $R_{25}$ represent H. In another embodiment $R_8$, $R_9$, $R_{12}$, $R_{13}$, $R_{20}$, $R_{21}$, $R_{22}$, $R_{23}$, $R_{24}$ and $R_{25}$ represent Me.

In one embodiment of the invention, there is provided a compound of formula (I) which is a compound of formula (A):

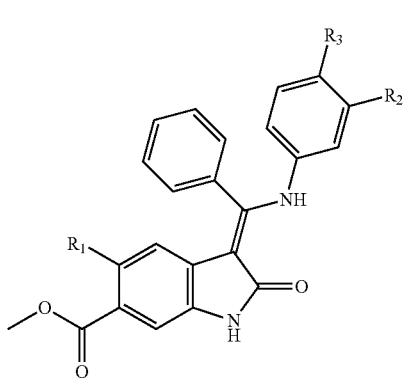

(A)

wherein $R_1$ represents Me, Et, CH=CH$_2$, C≡C—H or C≡C-Me;

one of $R_2$ and $R_3$ represents a group selected from H, —$C_1$-$C_6$alkyl, $C_1$-$C_6$alkoxy, —$C_3$-$C_8$cycloalkyl, —CH$_2$—($C_3$-$C_8$cycloalkyl), halogen and cyano, and the other represents the group —Z—$R_x$;

Z represents CO or SO$_2$;

$R_x$ represents formula (iv):

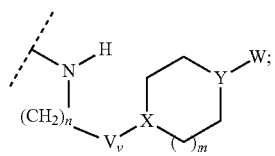

wherein V represents CO;
wherein v represents 0 or 1;
wherein n represents 0, 1 or 2, except that when v represents 1, n represents 1 or 2;
m represents 1 or 2;
X represents CH or N, except that when n represents 0 or 1, X represents CH;
Y represents CH or N;
W represents a group selected from —$C_1$-$C_4$alkyl, —$C_1$-$C_4$hydroxyalkyl, $C_1$-$C_4$alkoxy($C_1$-$C_4$)alkyl-, —$C_1$-$C_4$alkyleneCONR$_{20}$R$_{21}$, —$C_1$-$C_4$alkyleneNR$_{20}$COR$_{21}$, —SO$_2$($C_1$-$C_4$)alkyl, —CO($C_1$-$C_4$)alkyl, halogen, CN, OH and NR$_{22}$R$_{23}$ except that when W represents NR$_{22}$R$_{23}$, —$C_1$alkyleneNR$_{20}$COR$_{21}$ or halogen, Y represents CH;
$R_{20}$, $R_{21}$, $R_{22}$, $R_{23}$, $R_{24}$ and $R_{25}$ independently represent H or —$C_1$-$C_4$alkyl;
or a pharmaceutically acceptable salt thereof.

Suitably $R_1$ represents Me.
Suitably Z represents CO.
Suitably $R_3$ represents —Z—$R_x$.
When v is 0, suitably n represents 0 or 2, especially 0.
When v is 1, suitably n represents 1.
Suitably v represents 0.
Suitably m represents 1.
Suitably X represents CH.
Suitably Y represents N.
Suitably W represents —$C_1$-$C_4$alkyl (especially Me) or NR$_{22}$R$_{23}$ (especially NMe$_2$).

The compounds of formula (I) may conveniently be prepared by a process comprising reacting a compound of formula (II), in which L is a leaving group, such as —OC$_1$-C$_4$ alkyl, e.g. —Oethyl:

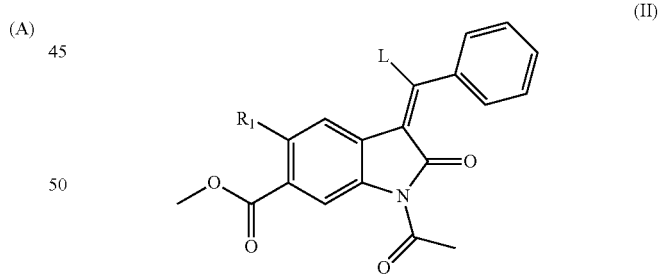

(II)

or a protected derivative thereof with a compound of formula (III):

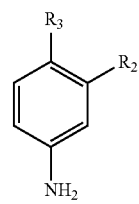

(III)

Typically, compounds of formulae (II) and (III) may be reacted in the presence of a solvent, such as DMF, and heated to about 80° C. for approximately 18 hours. Following this step, a deprotection step is performed to remove the protecting group, acetyl. To achieve this, the reaction mixture may be cooled to room temperature and a nucleophile, such as piperidine, added and stirred for 1 to 24 hours.

Compounds of formula (II) in which L represents —Oethyl may be prepared by reacting a compound of formula (IV):

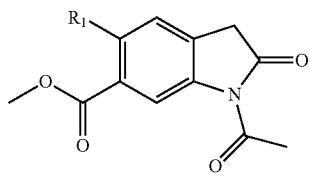
(IV)

or a protected derivative thereof with a compound of formula (V):

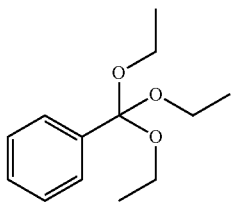
(V)

Typically compounds of formulae (IV) and (V) may be reacted in the presence of acetic anhydride at a temperature of about 110° C. for approximately 4 hours. Other compounds of formula (II) may be prepared in an analogous manner.

Compounds of formula (IV) may be prepared by reacting a compound of formula (VI):

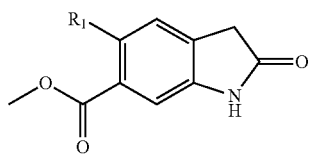
(VI)

with acetic anhydride. Typically the reaction is performed at about 110° C. Alternatively compounds of formula (II) in which L represents —Oethyl may be prepared directly from compounds of formula (VI) by treatment with a compound of formula (V) in the presence of acetic anhydride at a temperature of about 110° C. for approximately 4 hours.

Compounds of formula (VI) may be prepared by reducing the —NO$_2$ group of a compound of formula (VII):

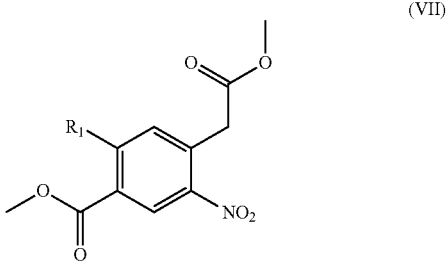
(VII)

to an —NH$_2$ group followed by an amide forming cyclisation, which is a well-known procedure in the field. Reduction and amide cyclisation conditions may typically include use of H$_2$—Pd/C at room temperature, and hydrogenating at 5 bar pressure for about 36 hours in a solvent, such as acetic acid, which is a well-known procedure in the art.

Compounds of formula (VII) may be prepared by reacting a compound of formula (VIII):

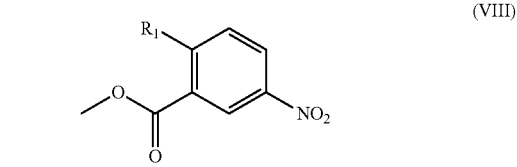
(VIII)

with methylchloroacetate. Typically the reaction occurs in the presence of a polar organic solvent, such a DMF, and a base, such as KO$^t$Bu, under a nitrogen atmosphere between approximately −20 to −10° C.

Alternatively compounds of formula (Ia), which are compounds of formula (I) in which Z is CO, may be prepared by reacting a compound of formula (IXa) or (IXb):

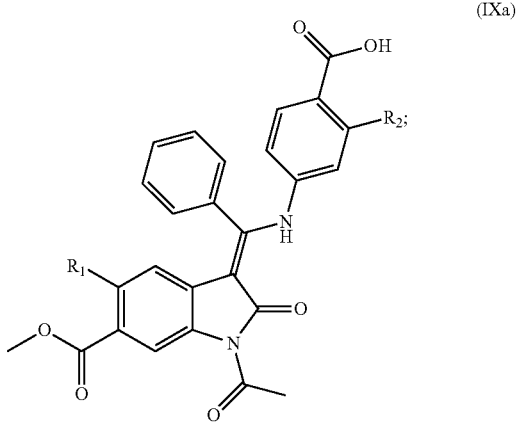
(IXa)

-continued

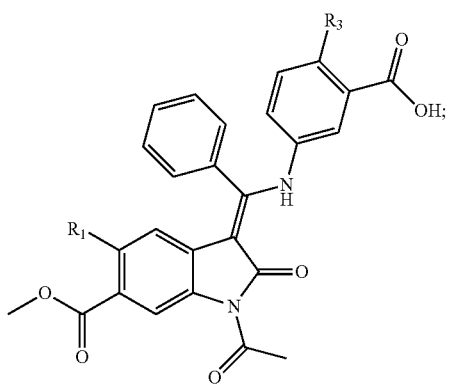
(IXb)

or protected derivatives thereof with a compound of formula H—R$_x$ or a protected derivative thereof via a condensation reaction between the NH-amino group present in H—R$_x$ and the COOH in (IXa) and (IXb). The compounds may typically be reacted for about 2 to 18 hours at room temperature in the presence of a coupling agent, such as HATU and a base, such as Hünig's base (DIPEA), in a polar organic solvent such as DMF, although other polar organic solvents can be used. This process may be followed, where appropriate, by deprotection.

Compounds of formulae (IXa) and (IXb) may be prepared by deprotection of compounds of formulae (Xa) and (Xb) respectively:

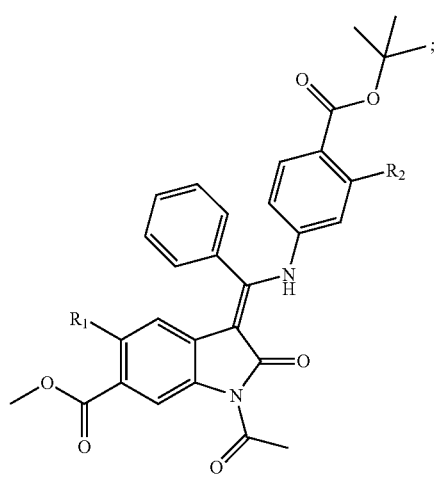
(Xa)

(Xb)

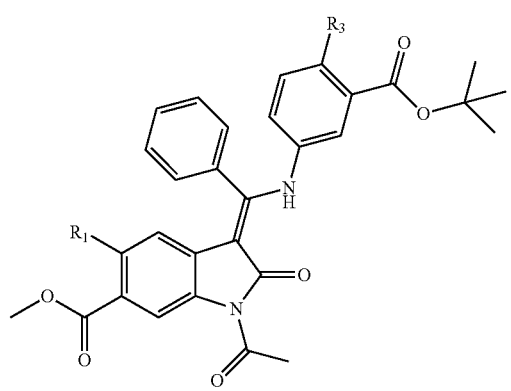

Deprotection may be achieved using standard reagents in the art, such as TFA, and the compounds are typically stirred at room temperature for about 16 hours in a solvent, such as DCM.

Compounds of formulae (Xa) and (Xb) may be prepared by reacting a compound of formula (II) with a compound of formula (XIa) and (XIb) respectively:

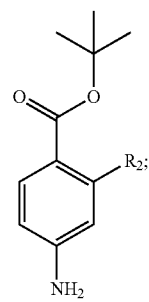
(XIa)

(XIb)
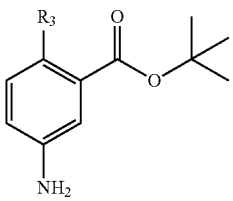

The compounds may be reacted in the presence of DMF for about 18 hours at 100° C.

Synthesis of compounds of formula (III) may be prepared by reacting a compound of formula H—R$_x$ with a compound of formula (XIIa) or (XIIb) respectively:

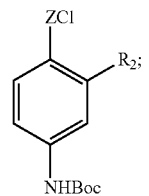
(XIIa)

(XIIb)
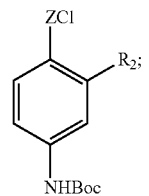

The compounds may typically be reacted in the presence of Hünig's base (DIPEA) and DMF for about 16 hours at room temperature, followed by a deprotection step using standard reagents in the art, such as TFA.

Alternatively compounds of formula (Ib), which are compounds of formula (I) in which Z is CO and R$_x$ is formula (ii):

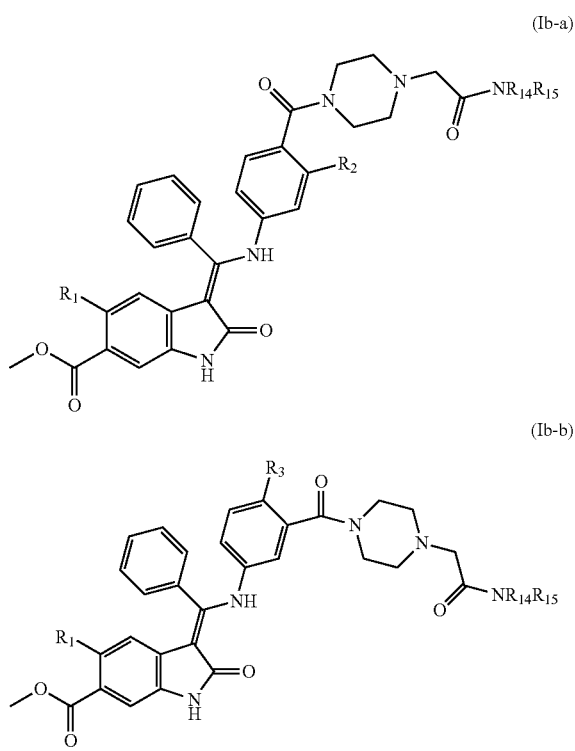

may be prepared by reacting a compound of formula (XIIIa) or (XIIIb):

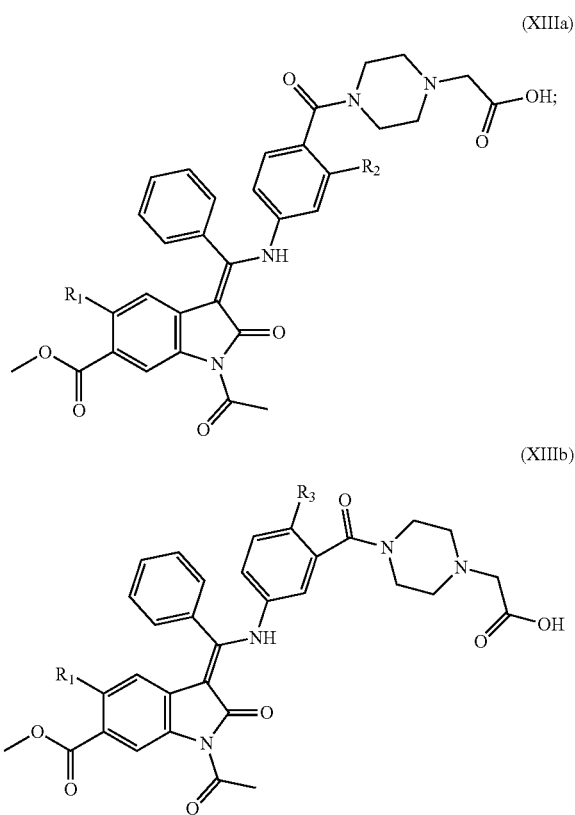

with a compound of $NHR_{14}R_{15}$. Typically, compounds of formulae (XIIIa) or (XIIIb) and $NHR_{14}R_{15}$ may be reacted in the presence of a coupling agent, such as HATU and a base, such as Hünig's base (DI PEA) in a solvent, such as DMF, and stirred at room temperature for approximately 4 hours. Following this step, a deprotection step is performed to remove the protecting group, acetyl. To achieve this, a nucleophile, such as piperidine, is added and stirred for 1 to 24 hours.

Compounds of formula (XIIIa) and (XIIIb) may be prepared by reacting a compound of formula (IXa) and (IXb) respectively with a compound of formula (XIV):

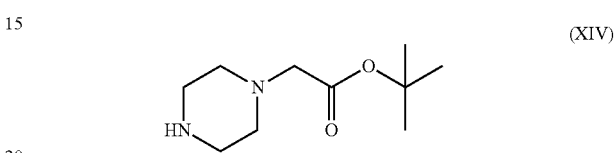

Typically, compounds of formulae (IX) and (XIV) may be reacted in the presence of a coupling agent, such as HATU and a base, such as Hünig's base (DI PEA) in a solvent, such as DMF, and stirred at room temperature for approximately 3 hours. Deprotection of the t-butyl group may be achieved using standard reagents in the art, such as TFA, and the compounds are typically stirred at room temperature for about 16 hours in a solvent, such as DCM.

Novel intermediates including compounds of formula (II), (VII), (IXa), (IXb), (Xa), (Xb), (XIIIa) and (XIIIb) wherein $R_1$ is Me, Et, CH=$CH_2$, C≡C—H or C≡C-Me, and formula (VI) wherein $R_1$ is Et, CH=$CH_2$, C≡C—H or C≡C-Me, and salts thereof are claimed as an aspect of the invention.

Compounds of formulae (V), (VIII), (XIa), (XIb), (XIIa), (XIIb), (XIV), $NHR_{14}R_{15}$, and H—$R_x$ may be prepared by known methods, or methods analogous to those described herein.

Compounds of formula (I) may be prepared or employed in the form of a pharmaceutically acceptable salt, including the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, ethanesulfonic, maleic, malonic, L-tartaric, fumaric, citric, succinic, acetic, triphenyl acetic, hydrochloric, sulfuric, phosphoric, 1-hydroxy-2-naphthoic, hydrobromic, methanesulfonic, tartaric, palmitic, isethionic, pamoic, formic, cinnamic benzoic, ascorbic, galactaric, lactic, malic, oxalic, para-toluenesulfonic, benzenesulphonic, propionic, furoic, phosphonic and glutaric. Conversely said salt forms can be converted by treatment with an appropriate base into the free base form.

The invention provides a compound of the invention for use as a pharmaceutical.

Further, the present invention provides a pharmaceutical composition comprising a compound according to the invention optionally in combination with one or more pharmaceutically acceptable diluents or carriers.

Diluents and carriers may include those suitable for parenteral, oral, topical including by inhalation via the mouth into the lungs or inhalation via the nose, mucosal and rectal administration, and may be different depending on the route of administration.

In one embodiment compositions may be prepared e.g. for parenteral administration e.g., subcutaneous, intramuscular, intravenous, intra-dermal, intra-articular or peri-articular administration, particularly in the form of liquid solutions or suspensions; for oral administration, particularly in the form of tablets, capsules, powder, granules, solid dispersions or in the form of liquid solutions or suspensions including nano-suspensions; for inhalation to the lungs or nose e.g. pulmonary or intranasal administration, particularly in the form of dry powders, solutions, suspensions including nanosuspensions for nebulisation, nasal sprays or drops comprising solutions or suspensions or suspension or solution pressurised or non-pressurised aerosols; for topical or transdermal administration e.g. as creams, sprays, foams, gels, ointments, liquids, patches; for mucosal administration e.g. to buccal, sublingual or vaginal mucosa, and for rectal administration e.g. in the form of a foam or suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Formulations for parenteral administration may contain as excipients sterile water or saline, buffers, tonicity-adjusting agents, preservatives, anti-oxidants, viscosity adjusting agents, alkylene glycols such as propylene glycol, polyalkylene glycols such as polyethylene glycol, oils of vegetable origin, hydrogenated naphthalenes and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, celluloses or polyvinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents and surfactants such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxypropyl methylcellulose (HPMC).

A dry shell formulation typically comprises of about 40%-60% concentration of gelatin, about a 20%-30% concentration of plasticizer (such as glycerin, sorbitol or propylene glycol) and about a 30%-40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Formulations for nasal administration may be powders and may contain excipients, for example, lactose or dextran, or may be aqueous or oily solutions for use in the form of nasal drops or metered spray. Formulations for nasal administration may also be in the form of aqueous suspensions or pressurised non-aqueous solutions or suspensions. For buccal administration typical excipients include sugars, calcium stearate, magnesium stearate, pregelatinated starch, and the like.

Suitably the compound of formula (I) is administered topically to the lung. Hence in one embodiment there is provided a pharmaceutical composition comprising a compound of the disclosure optionally in combination with one or more topically acceptable diluents or carriers.

Topical administration to the lung may be achieved by use of a non-pressurised formulation such as an aqueous solution or suspension. These formulations may be administered by means of a nebuliser e.g. one that can be hand-held and portable or for home or hospital use (ie non-portable). The formulation may comprise excipients such as water, buffers, tonicity adjusting agents, pH adjusting agents, surfactants, preservatives, suspending agents, bulking agents and co-solvents. Suspension liquid and aerosol formulations (whether pressurised or unpressurised) will typically contain the compound of the invention in finely divided form suitable for deposition into the lung, for example with a $D_{50}$ of 0.5-10 μm e.g. around 1-5 μm. Powders in finely divided form may be prepared by a micronization or milling process, by spray drying, by spray freezing, or by wet milling followed by spray drying. Micronization may be performed using a jet mill such as those manufactured by Hosokawa Alpine. The resultant particle size distribution may be measured using laser diffraction (e.g. with a Malvern Mastersizer 2000S or a Mastersizer 3000 instrument). Particle size distributions may be represented using $D_{10}$, $D_{50}$ and $D_{90}$ values. The $D_{50}$ median value of particle size distributions is defined as the particle size that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively. In another embodiment, composite particles of the compound of the disclosure and excipients for use in nebulisation of a suspension formulation may be formed by co-milling and/or co-spray drying the compound and excipients together, wherein the composite particles comprising both active and excipients have a $D_{50}$ of 1-10 μm. Aqueous suspension formulations for delivery to the lung could also comprise nanosuspensions or suspensions of composite particles containing nanoparticles.

Topical administration to the lung may also be achieved by use of a pressurised aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants or stabilisers (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Aptar or 3M or alternatively by Coster or Vari). Pressurised suspensions formulations for delivery to the lung could also comprise nanosuspensions or suspensions of composite particles containing nanoparticles.

Topical administration to the lung may also be achieved by use of a dry-powder formulation. A dry powder formulation will contain the compound of the disclosure in finely divided form, typically with a $D_{50}$ of 0.5-10 µm e.g. around 1-5 µm. Powders in finely divided form may be prepared by a micronization or milling process, by spray drying, by spray freezing, or by wet milling followed by spray drying. Micronization may be performed using a jet mill such as those manufactured by Hosokawa Alpine. The resultant particle size distribution may be measured using laser diffraction (e.g. with a Malvern Mastersizer 2000S or a Mastersizer 3000 instrument). The formulation will typically contain one or more topically acceptable diluents such as lactose, glucose, trehalose or mannitol (preferably lactose), usually of comparatively large particle size e.g. a $D_{50}$ of 15-250 µm. In another embodiment, composite particles of the compound of the disclosure and excipients may also be formed by co-milling and/or co-spray drying the compound and excipients together, wherein the composite particles comprising both active and excipients have a $D_{50}$ of 1-10 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (DFE Pharma), InhaLac® (Meggle), Pharmatose® (DFE Pharma) and Respitose® (DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as leucine, sodium stearate, calcium stearate or magnesium stearate. Dry powder particles could be composite particles and could be comprised of nanoparticles in a composite matrix.

A dry powder formulation is typically delivered using a dry powder inhaler (DPI) device. This can either be a unit dose device where the formulation is presented in individual units, either as capsules or blisters, or in a multi-dose device where more than one dose of formulation is contained in a device, either in a bulk reservoir or as multiple containers within a device (eg multiple blisters or pockets). Example dry powder inhalers include SPINHALER, DISKHALER, TURBOHALER, DISKUS, ELLIPTA, CLICKHALER, ECLIPSE, ROTAHALER, HANDIHALER, AEROLISER, CYCLOHALER, MONODOSE, BREEZHALER/NEOHALER, FLOWCAPS, TWINCAPS, X-CAPS, TWISTER, TURBOSPIN, ELPENHALER, TURBUHALER, MIATHALER, NEXTHaler, TWISTHALER, NOVOLIZER, GENUAIR, SKYEHALER, ORIEL dry powder inhaler, MICRODOSE, ACCUHALER, PULVI NAL, EASYHALER, ULTRAHALER, TAIFUN, PULMOJET, OMNIHALER, GYROHALER, TAPER, CONIX, XCELOVAIR and PROHALER.

The compounds of the invention are expected to be useful in the treatment of fibrotic diseases such as lung fibrosis and pulmonary diseases with a fibrotic component e.g. selected from IPF, giant cell interstitial pneumonia, sarcoidosis, cystic fibrosis, respiratory distress syndrome, drug-induced lung fibrosis, granulomatosis, silicosis, asbestosis, systemic scleroderma, the virally induced hepatic cirrhosis selected from hepatitis C induced hepatic cirrhosis, or diseases of the skin with a fibrotic component e.g. selected from scleroderma, sarcoidosis and systemic lupus erythematosus, and especially IPF. More generally, the compounds of the invention are expected to be useful in the treatment of interstitial lung diseases. In addition, the compounds of the invention are expected to be useful in the treatment of diseases characterized by hyperproliferation of cells, for example, cancer and wherein the compounds are delivered by inhalation, particularly lung cancer. Furthermore, the compounds of the invention may also be useful in the treatment of respiratory disorders including COPD (including chronic bronchitis and emphysema), asthma, paediatric asthma, allergic rhinitis, rhinitis, sinusitis, especially asthma, chronic bronchitis and COPD.

The compounds of the invention are also expected to be useful in the treatment of other fibrotic diseases such as lung fibrosis associated with rheumatoid arthritis, respiratory distress syndrome including acute respiratory distress syndrome, acute lung injury, radiation induced lung fibrosis or pneumonitis, chronic hypersensitivity pneumonitis, systemic sclerosis, Sjogren's syndrome, interstitial lung diseases, pulmonary arterial hypertension (PAH), including the vascular component of PAH, or diseases of the skin with a fibrotic component e.g. selected from hypertrophic scarring and keloids, or eye diseases where fibrosis is a component including glaucoma, age related macular degeneration, diabetic macular edema, dry eye disease and diabetic retinopathy, or fibrosis in the gut e.g. associated with inflammatory bowel disease.

In addition, the compounds of the invention are expected to be useful in the prevention of diseases characterized by hyperproliferation of cells, for example, cancer e.g. wherein the compounds are delivered by inhalation, particularly lung cancer.

The invention provides a compound of the invention for use in the treatment of one or more of the above mentioned diseases. The invention also provides use of a compound of the invention in the manufacture of a medicament for the treatment of one or more of the above mentioned diseases.

The invention also provides a method of treatment of one of the above mentioned diseases which comprises administering to a subject (especially a human subject) in need thereof a therapeutically effective amount of a compound of the invention.

The word "treatment" is intended to embrace prophylaxis as well as therapeutic treatment.

Compounds of the invention may be administered once, twice or thrice per day, especially once or twice per day. A suitable dosage amount may be determined by reference to the severity of the disease and the size of the subject. Typical dosage amounts are in the range 0.01 mg to 100 mg, e.g. 0.1 mg to 10 mg e.g. 0.25 mg to 5 mg per human dose to be delivered once, twice or thrice per day, especially once or twice per day.

The compound of the disclosure may also be administered in combination with one or more other active ingredients e.g. active ingredients suitable for treating the above mentioned conditions. For example possible active ingredients include nintedanib or pirfenidone (these being known for treatment of IPF). Other active ingredients to be used in combination include substances with a secretolytic, broncholytic and/or anti-inflammatory activity, such as anticholinergic agents, beta-2 mimetics, steroids, PDE-IV inhibitors, p38 MAP kinase inhibitors, MK2 inhibitors, galectin inhibitors, $NK_1$ antagonists, $LTD_4$ antagonists, EGFR inhibitors, VEGF inhibitors, PDGF inhibitors, FGF inhibitors, TGFbeta inhibitors, LPA1 antagonists, LOXL2 inhibitors, CTGF inhibitors, pentoxyfylline, N-acetylcysteine, anti-IL13 agents, anti IL4 agents, Alphavβ6 integrin inhibitors, IGF inhibitors, PI3K inhibitors, mTOR inhibitors, JNK inhibitors, pentraxin2 and endothelin-antagonists.

Other active ingredients to be used in combination include substances with an antifibrotic activity, such as PDE-III inhibitors, combined anti-IL4/13 agents, combined PI3k/mTOR inhibitors, autotaxin inhibitors, $P2X_3$ antagonists, CTGF antagonists, 5-LO antagonists, leukotriene antagonists and ROCK inhibitors.

In one embodiment the combination of active ingredients are co-formulated.

In one embodiment the combination of active ingredients is co-administered sequentially or simultaneously.

In one embodiment the compounds of the invention are delivered by inhalation and the other possible active ingredients are delivered orally or parenterally.

In one embodiment there is provided a combination product comprising:
(A) a compound of the invention; and
(B) a further active ingredient (as mentioned above)
wherein each of components (A) and (B) is formulated in admixture with pharmaceutically-acceptable diluent(s) or carrier(s). The combination may optionally comprise additional relevant excipients.

In one embodiment there is provided a compound of the invention for use as a medicament to be administered in combination with one or more further active ingredients (as mentioned above).

Compounds of the invention are expected to have one or more of the following advantageous properties:
  Good inhibitory activity of kinases selected from VEGFR (e.g. VEGFR1 and VEGFR2), FGFR and PDGFR;
  Good anti-fibrosis activity e.g. as determined in in vivo models (e.g. bleomycin fibrosis model) when delivered topically to the lung;
  Suitable physical and chemical properties and low dose for a medicinal product, particularly one intended to be delivered topically to the lung;
  Good residency time in the lung or duration of action when administered topically to the lung;
  Low permeability in the PAMPA permeability assay;
  Good duration of action e.g. as measured by inhibition of PDGF-BB induced phosphorylation of BDGFRβ in human fetal lung fibroblast cells;
  Good safety and tolerability when administered topically to the lung;
  Low oral bioavailability.

EXPERIMENTAL SECTION

Abbreviations used herein are defined below (Table 1). Any abbreviations not defined are intended to convey their generally accepted meaning.

TABLE 1

| Abbreviations | |
|---|---|
| AcOH | glacial acetic acid |
| aq | aqueous |
| br | broad |
| BEH | ethylene bridged hybrid |
| Boc | tert-butoxycarbonyl |
| CSH | charged surface hybrid |
| conc | concentrated |
| d | doublet |
| δ | chemical shift |
| DCM | dichloromethane |
| DIAD | diisopropyl azodicarboxylate |
| DMF | N,N-dimethylformamide |
| DMSO | dimethyl sulfoxide |
| (ES$^+$) | electrospray ionization, positive mode |
| (ES$^-$) | electrospray ionization, negative mode |
| Et | ethyl |
| EtOAc | ethyl acetate |
| EtOH | ethanol |
| h | hour(s) |
| HATU | 1-[bis(dimethylamino)methylene]-1H-1,2,3-triazolo[4,5-b]pyridinium 3-oxid hexafluorophosphate |
| Hünig's base | N,N-diisopropylethylamine |
| M | molar |
| m | multiplet |
| (M + H)$^+$ | protonated molecular ion |
| (M − H)$^-$ | deprotonated molecular ion |
| Me | methyl |
| MeCN | acetonitrile |
| MeOH | methanol |
| MHz | megahertz |
| min | minute(s) |
| m/z | mass-to-charge ratio |
| NMR | nuclear magnetic resonance (spectroscopy) |
| p | pentuplet |
| Ph | phenyl |
| Py | pyridine |
| q | quartet |
| rt | room temperature |
| HPLC | high performance liquid chromatography |
| s | singlet |
| sat | saturated |
| SAX | solid supported anion exchange (resin) |
| SCX | solid supported cation exchange (resin) |
| t | triplet |
| $^t$Bu | tert-butyl |
| THF | tetrahydrofuran |
| TFA | trifluoroacetic acid |
| UV | ultra-violet |

Chemistry Examples

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under pressure in a gas autoclave (bomb).

Column chromatography was performed on pre-packed silica (230-400 mesh, 40-63 μm) cartridges using the amount indicated. SCX was purchased from Supelco and treated with 1 M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Preparative Reverse Phase High Performance Liquid Chromatography

Performed using UV detection at 215 and 254 nm with either a Waters X-Select Prep-C18, 5 μm, 19×50 mm column eluting with a $H_2O$-MeCN gradient containing 0.1% v/v formic acid over 10 min (Method A), or a Waters X-Bridge Prep-C18, 5 μm, 19×50 mm column eluting with a H$_2$O-MeCN gradient containing 0.1% ammonium bicarbonate over 10 min (Method B).

Analytical Methods

Reverse Phase High Performance Liquid Chromatography

Method 1:

Waters XSelect CSH C18 2.5 μm (4.6×30 mm) at 40° C.; flow rate 2.5-4.5 mL min$^{-1}$ eluted with a H$_2$O-MeCN gradient containing 0.1% v/v formic acid over 4 min employing UV detection at 254 and 215 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01-3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

Method 2:

Waters XBridge BEH C18, 2.5 μm (4.6×30 mm) at 40° C.; flow rate 2.5-4.5 mL min$^{-1}$ eluted with a H$_2$O-MeCN gradient containing 10 mM ammonium bicarbonate over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL min$^{-1}$; 3.01-3.50 min, held at 5% H$_2$O-95% MeCN; 3.50-3.60 min, returned to 95% H$_2$O-5% MeCN, flow rate reduced to 3.50 mL min$^{-1}$; 3.60-3.90 min, held at 95% H$_2$O-5% MeCN; 3.90-4.00 min, held at 95% H$_2$O-5% MeCN, flow rate reduced to 2.5 mL min$^{-1}$.

$^1$H NMR Spectroscopy $^1$H NMR spectra were acquired on a Bruker Avance III spectrometer at 400 MHz using residual undeuterated solvent as reference and unless specified otherwise were run in DMSO-d$_6$.

All chemical names have been generated using CambridgeSoft ENotebook 12.0.

Route 1A

Example 1: (Z)-Methyl 5-methyl-3-(((4-(N-(2-(4-methylpiperazin-1-yl)ethyl)sulfamoyl)phenyl)amino)(phenyl)methylene)-2-oxoindoline-6-carboxylate, 0.8 formate Intermediate A: Methyl 4-(2-methoxy-2-oxoethyl)-2-methyl-5-nitrobenzoate

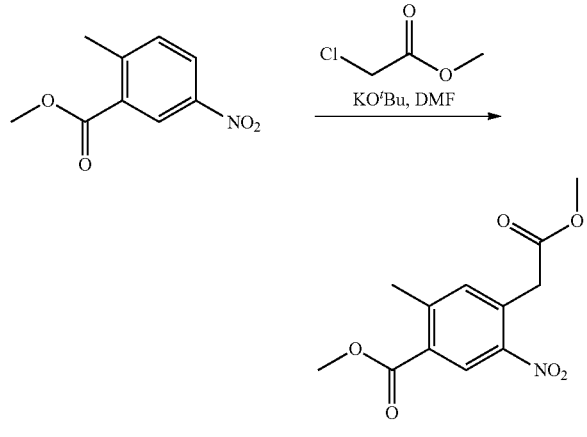

To a stirred solution of potassium tert-butoxide (35.9 g, 320 mmol) in DMF (350 mL), under a nitrogen atmosphere at −20° C., was added a solution of methyl 2-methyl-5-nitrobenzoate (25.0 g, 128 mmol) and methyl 2-chloroacetate (16.9 mL, 192 mmol) in DMF (300 mL) dropwise over 40 minutes. The reaction mixture was warmed to −10° C. over 2 h and then poured onto an ice-HCl slurry (900 g ice, 500 mL 35 wt % aq HCl). The mixture was extracted with DCM (2×600 mL) and the combined organic layers washed with brine (2×400 mL) and then evaporated under reduced pressure. The crude product so obtained was purified by flash column chromatography (SiO$_2$, 330 g, 0-10% EtOAc in DCM, gradient elution) to afford the subtitle compound methyl 4-(2-methoxy-2-oxoethyl)-2-methyl-5-nitrobenzoate as an orange syrup (31.0 g, 89%); R$^t$ 2.06 min (Method 1); m/z 266 (M−H)$^-$ (ES$^-$); $^1$H NMR δ: 2.61 (3H, s), 3.62 (3H, s), 3.88 (3H, s), 4.12 (2H, s), 7.59 (1H, s), 8.51 (1H, s).

Intermediate B: Methyl 5-methyl-2-oxoindoline-6-carboxylate

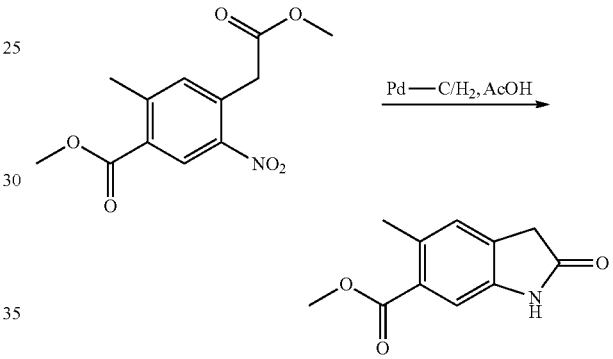

To a solution of methyl 4-(2-methoxy-2-oxoethyl)-2-methyl-5-nitrobenzoate (Intermediate A) (23.0 g, 86.0 mmol) in acetic acid (301 mL, 5.25 mol) was added palladium on carbon [5 wt %, 58% water, type 87L] (3.30 g, 1.55 mmol). The mixture was hydrogenated at rt under an atmosphere of H$_2$ (5 bar) for 36 h and then filtered through a pad of celite. The filter cake was washed with EtOAc (500 mL) and the filtrate concentrated under reduced pressure. The crude residue was dissolved in hot refluxing MeOH (200 mL) and the mixture cooled to rt. The resultant solid was filtered, rinsing with MeOH (200 mL) and dried in vacuo to afford the subtitle compound methyl 5-methyl-2-oxoindoline-6-carboxylate as a brown powder (7.00 g, 39%); R$^t$ 1.48 min (Method 1); m/z 206 (M+H)$^+$ (ES$^+$); $^1$H NMR δ: 2.45 (3H, s), 3.32 (2H, s), 3.81 (3H, s), 7.17 (1H, s), 7.22 (1H, s), 10.43 (1H, s).

Intermediate C: (E)-Methyl 1-acetyl-3-(ethoxy(phenyl)methylene)-5-methyl-2-oxoindoline-6-carboxylate

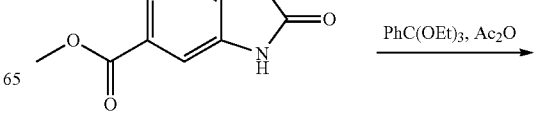

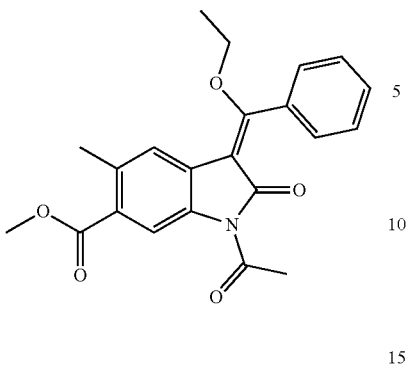

To a stirred solution of methyl 5-methyl-2-oxoindoline-6-carboxylate (Intermediate B) (5.00 g, 24.4 mmol) in acetic anhydride (50.6 mL, 536 mmol) was added (triethoxymethyl)benzene (22.1 mL, 97.0 mmol) and the mixture was stirred at 110° C. for 3 h. Thereafter, stirring was continued at rt for 18 h. The reaction mixture was concentrated under reduced pressure and the residue was triturated with MeOH (50 mL). The resultant solid was filtered, rinsing with MeOH (50 mL) and dried in vacuo to afford the subtitle compound (E)-methyl 1-acetyl-3-(ethoxy(phenyl)methylene)-5-methyl-2-oxoindoline-6-carboxylate as a yellow powder (4.50 g, 48%); $R^t$ 2.70 min (Method 1); m/z 380 (M+H)$^+$ (ES$^+$); $^1$H NMR δ: 1.35 (3H, t), 2.42 (3H, s), 2.58 (3H, s), 3.84 (3H, s), 4.01 (2H, q), 7.45-7.62 (5H, overlapping m), 7.90 (1H, s), 8.64 (1H, s).

(Z)-Methyl 5-methyl-3-(((4-(N-(2-(4-methylpiperazin-1-yl)ethyl)sulfamoyl)phenyl)amino)(phenyl)methylene)-2-oxoindoline-6-carboxylate, 0.8 formate

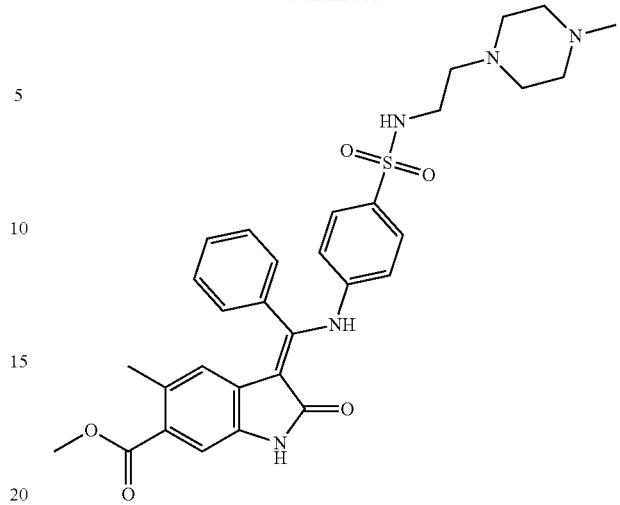

A mixture of (E)-methyl 1-acetyl-3-(ethoxy(phenyl)methylene)-5-methyl-2-oxoindoline-6-carboxylate (Intermediate C) (100 mg, 0.264 mmol) and 4-amino-N-(2-(4-methylpiperazin-1-yl)ethyl)benzenesulfonamide, di-trifluoroacetate salt (387 mg, 0.316 mmol) in DMF (3 mL) was heated at 80° C. for 16 h. Piperidine (261 µl, 2.64 mmol) was added and the mixture was stirred at rt for 2 h. The solvent was removed under reduced pressure and the residue was dissolved in 10% MeOH in DCM solution (20 mL) and washed with water (20 mL). The layers were separated using a phase separator cartridge and the organic layer was concentrated under reduced pressure. The crude product was purified by preparative HPLC (Method A, 20-50% MeCN in water) to afford the title compound (Z)-methyl 5-methyl-3-(((4-(N-(2-(4-methylpiperazin-1-yl)ethyl)sulfamoyl)phenyl)amino)(phenyl)methylene)-2-oxoindoline-6-carboxylate, 0.8 formate as a light yellow solid (25 mg, 14%); $R^t$ 1.58 min (Method 1); m/z 590 (M+H)$^+$ (ES$^+$); $^1$H NMR δ: 2.14 (6H, s), 2.17-2.35 (8H, overlapping m), 2.74-2.82 (2H, m), 3.76 (3H, s), 5.64 (1H, s), 6.96 (2H, m), 7.37 (1H, s), 7.41 (1H, m), 7.50-7.59 (4H, overlapping m), 7.60-7.73 (3H, overlapping m), 8.19 (0.8H, s), 10.92 (1H, s), 12.24 (1H, s). (Missing 2H-presumed obscured by solvent).

Route 1B

Example 2: (Z)-Methyl 3-(((4-((2-(dimethylamino)ethyl)carbamoyl)phenyl)amino)(phenyl)methylene)-5-methyl-2-oxoindoline-6-carboxylate, formate Intermediate D: (Z)-Methyl 1-acetyl-3-(((4-(tert-butoxycarbonyl)phenyl)amino)(phenyl)methylene)-5-methyl-2-oxoindoline-6-carboxylate

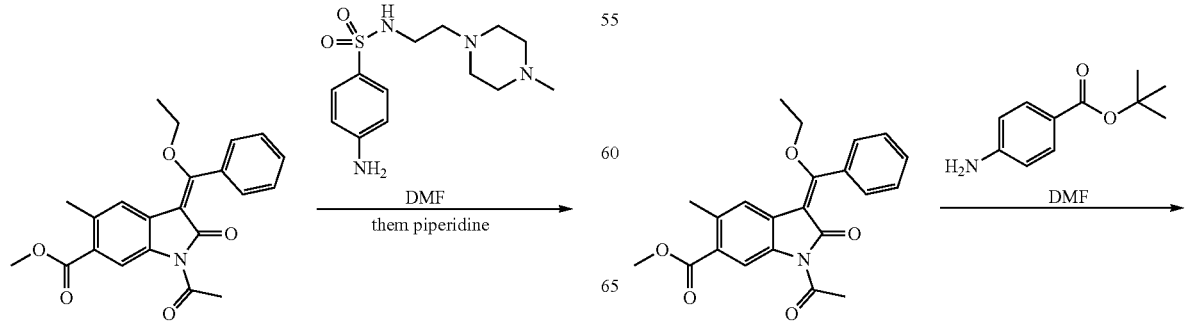

27

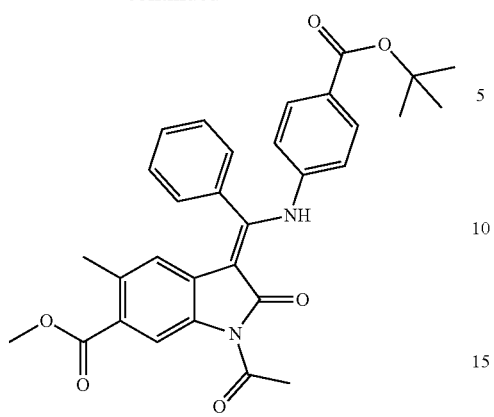

A mixture of (E)-methyl 1-acetyl-3-(ethoxy(phenyl)methylene)-5-methyl-2-oxoindoline-6-carboxylate (Intermediate C) (1.00 g, 2.64 mmol) and tert-butyl 4-aminobenzoate (509 mg, 2.64 mmol) in DMF (9 mL) was heated at 100° C. for 18 h. After cooling to rt, the precipitate was collected by filtration, washed with Et$_2$O (10 mL) and dried in vacuo to afford the subtitle compound (Z)-methyl 1-acetyl-3-(((4-(tert-butoxycarbonyl)phenyl)amino)(phenyl)methylene)-5-methyl-2-oxoindoline-6-carboxylate as a yellow solid (1.20 g, 86%); R$^t$ 3.23 min (Method 1); m/z 527 (M+H)$^+$ (ES$^+$); $^1$H NMR δ: 1.50 (9H, s), 2.13 (3H, s), 2.73 (3H, s), 3.78 (3H, s), 5.54 (1H, s), 7.04 (2H, m), 7.51 (2H, m), 7.58-7.72 (5H, overlapping m), 8.68 (1H, s), 11.89 (1H, s).

Intermediate E: (Z)-4-(((1-Acetyl-6-(methoxycarbonyl)-5-methyl-2-oxoindolin-3-ylidene)(phenyl)methyl)amino)benzoic acid, trifluoroacetate adduct

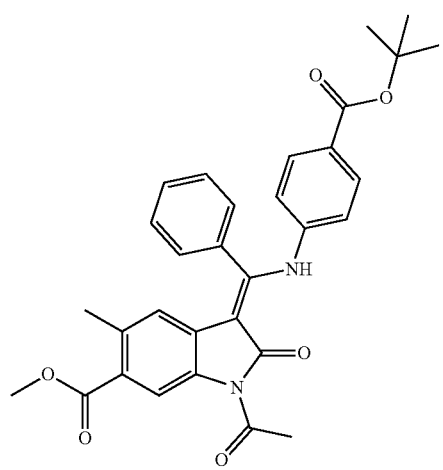

28

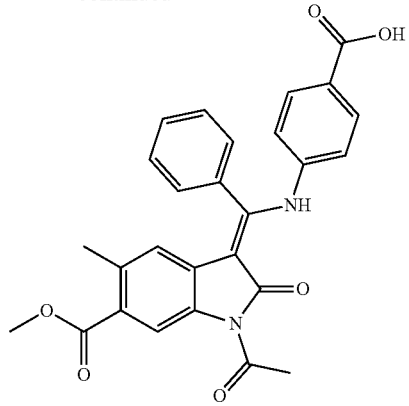

To a solution of (Z)-methyl 1-acetyl-3-(((4-(tert-butoxycarbonyl)phenyl)amino)(phenyl)methylene)-5-methyl-2-oxoindoline-6-carboxylate (Intermediate D) (1.20 g, 2.28 mmol) in DCM (14 mL) was added TFA (1.76 mL, 22.8 mmol) and the mixture was stirred at rt for 72 h. The solvent was removed under reduced pressure to afford the subtitle compound (Z)-4-(((1-acetyl-6-(methoxycarbonyl)-5-methyl-2-oxoindolin-3-ylidene)(phenyl)methyl)amino)benzoic acid, trifluoroacetate adduct as a yellow solid (1.00 g, 72%); R$^t$ 2.72 min (Method 1); m/z 471 (M+H)$^+$ (ES$^+$); $^1$H NMR δ: 2.13 (3H, s), 2.73 (3H, s), 3.78 (3H, s), 5.54 (1H, s), 7.04 (2H, m), 7.50 (2H, m), 7.57-7.76 (5H, overlapping m), 8.68 (1H, s), 11.89 (1H, s), 12.89 (1H, s).

(Z)-Methyl 3-(((4-((2-(dimethylamino)ethyl)carbamoyl)phenyl)amino)(phenyl)methylene)-5-methyl-2-oxoindoline-6-carboxylate, formate

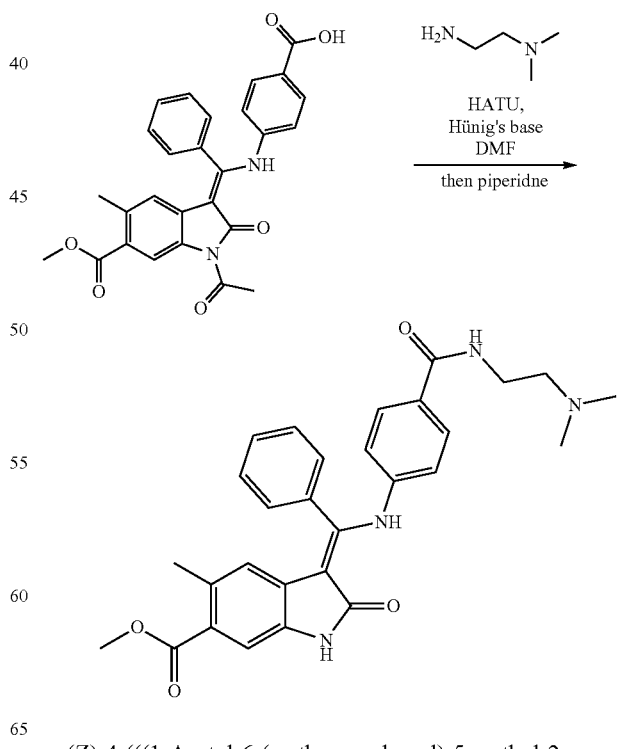

(Z)-4-(((1-Acetyl-6-(methoxycarbonyl)-5-methyl-2-oxoindolin-3-ylidene)(phenyl)methyl)amino)benzoic acid, trifluoroacetate adduct (Intermediate E) (75 mg, 0.128 mmol) and HATU (73.2 mg, 0.192 mmol) in DMF (2 mL) were stirred at rt for 10 min. Then Hünig's base (179 µl, 1.027 mmol) and N¹,N¹-dimethylethane-1,2-diamine (37.8 µl, 0.346 mmol) were added. The mixture was stirred at rt for 16 h. Piperidine (127 µl, 1.28 mmol) was added. The mixture was stirred at rt for 4 h and the reaction mixture was partitioned between DCM (25 mL) and saturated aqueous NaHCO₃ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl-3-(((4-((2-(dimethylamino)ethyl)carbamoyl)phenyl)amino)(phenyl)methylene)-5-methyl-2-oxoindoline-6-carboxylate, formate as a light yellow solid (3.7 mg, 5%); R$^t$ 1.53 min (Method 1); m/z 499 (M+H)⁺ (ES⁺); ¹H NMR δ: 2.14 (3H, s), 2.80 (6H, s), 3.17-3.23 (2H, overlapping m), 3.50-3.56 (2H, overlapping m), 3.75 (3H, s), 5.63 (1H, s), 6.90 (2H, m), 7.37 (1H, s), 7.52 (2H, m), 7.56-7.72 (5H, overlapping m), 8.56 (1H, m), 10.89 (1H, s), 12.22 (1H, s).

Example 3: (Z)-Methyl 5-methyl-3-(((4-(((1-methylpiperidin-4-yl)methyl)carbamoyl)phenyl)amino) (phenyl)methylene)-2-oxoindoline-6-carboxylate, formate

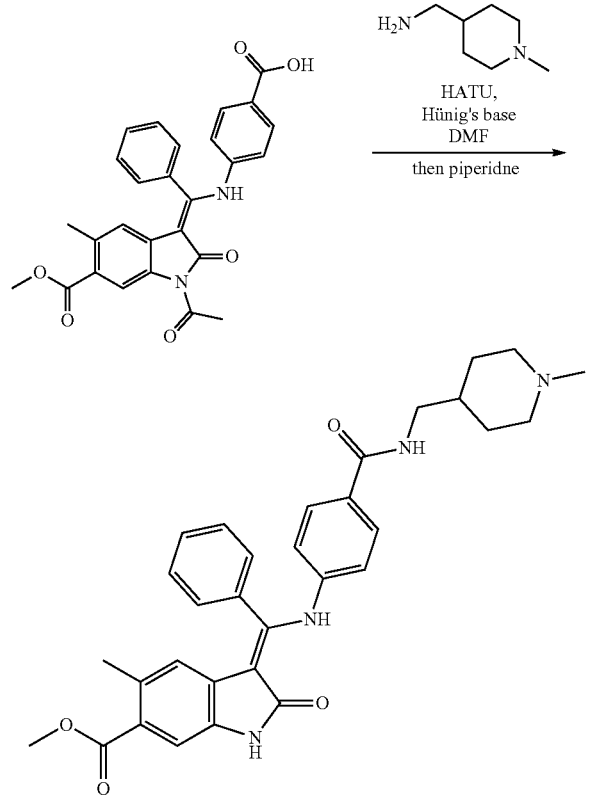

(Z)-4-(((1-Acetyl-6-(methoxycarbonyl)-5-methyl-2-oxoindolin-3-ylidene)(phenyl)methyl)amino)benzoic acid, trifluoroacetate adduct (Intermediate E) (75 mg, 0.128 mmol) and HATU (73.2 mg, 0.192 mmol) in DMF (2 mL) were stirred at rt for 10 min. Then Hünig's base (179 µl, 1.02 mmol) and (1-methylpiperidin-4-yl)methanamine (32.9 mg, 0.257 mmol) in DMF (0.2 mL) were added. The mixture was stirred at rt for 16 h. Piperidine (127 µl, 1.28 mmol) was added. The mixture was stirred at RT for 4 h and the reaction mixture was partitioned between DCM (25 mL) and saturated aqueous NaHCO₃ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 5-methyl-3-(((4-(((1-methylpiperidin-4-yl)methyl)carbamoyl)phenyl) amino) (phenyl)methylene)-2-oxoindoline-6-carboxylate, formate as a light yellow solid (19 mg, 25%); R$^t$ 1.55 min (Method 1); m/z 539 (M+H)⁺ (ES⁺); ¹H NMR δ: 1.11-1.28 (2H, overlapping m), 1.53 (1H, m), 1.60-1.73 (2H, overlapping m), 2.13 (3H, s), 2.15-2.24 (2H, overlapping m), 2.34 (3H, s), 2.89-3.00 (2H, overlapping m), 3.09 (2H, t), 3.75 (3H, s), 5.61 (1H, s), 6.87 (2H, m), 7.36 (1H, s), 7.52 (2H, m), 7.58-7.69 (5H, overlapping m), 8.17 (1H, s), 8.36 (1H, t), 10.88 (1H, s), 12.23 (1H, s).

Example 4: (Z)-Methyl 5-methyl-3-(((4-((2-(4-methylpiperazin-1-yl)ethyl)carbamoyl)phenyl) amino)(phenyl)methylene)-2-oxoindoline-6-carboxylate

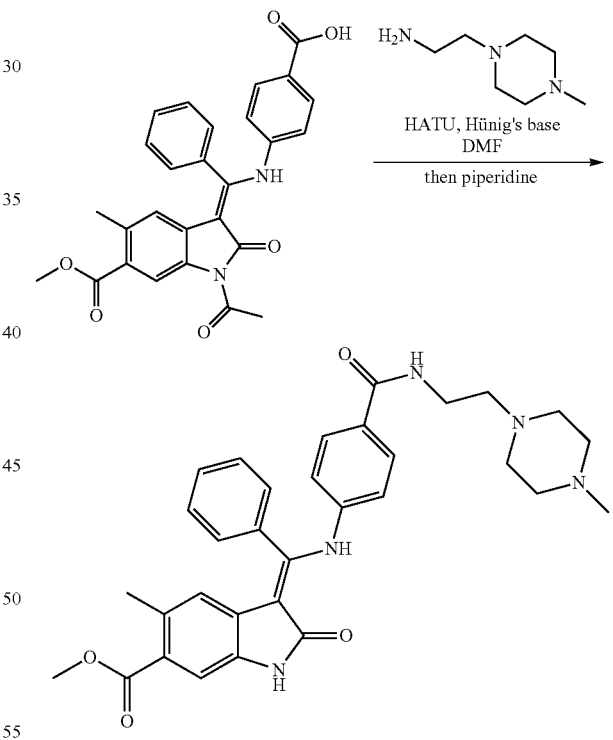

(Z)-4-(((1-Acetyl-6-(methoxycarbonyl)-5-methyl-2-oxoindolin-3-ylidene)(phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 2-(4-methylpiperazin-1-yl)ethanamine (50 mg, 0.346 mmol) in DMF (0.5 mL) were added. The mixture was stirred at rt for 3 h and piperidine (127 µl, 1.28 mmol) was added. The mixture was stirred at rt for 18 h. The reaction mixture was partitioned between DCM (25 mL) and saturated aqueous NaHCO₃ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 5-methyl-3-(((4-((2-(4-methylpiperazin-1-yl)ethyl)carbamoyl)phenyl)amino) (phenyl)methylene)-2-oxoindoline-6-carboxylate as a light yellow solid (19 mg, 25%); $R^t$ 1.46 min (Method 1); m/z 554 (M+H)$^+$ (ES$^+$); $^1$H NMR δ: 2.13 (3H, s), 2.21 (3H, s), 2.32-2.46 (8H, overlapping m), 3.27-3.34 (4H, overlapping m), 3.75 (3H, s), 5.62 (1H, s), 6.87 (2H, m), 7.36 (1H, s), 7.52 (2H, m), 7.56-7.69 (5H, overlapping m), 8.26 (1H, t), 10.87 (1H, s), 12.22 (1H, s).

Example 5: (Z)-Methyl 5-methyl-3-(((4-((2-(4-methyl-1,4-diazepan-1-yl)ethyl)carbamoyl)phenyl)amino) (phenyl)methylene)-2-oxoindoline-6-carboxylate, formate

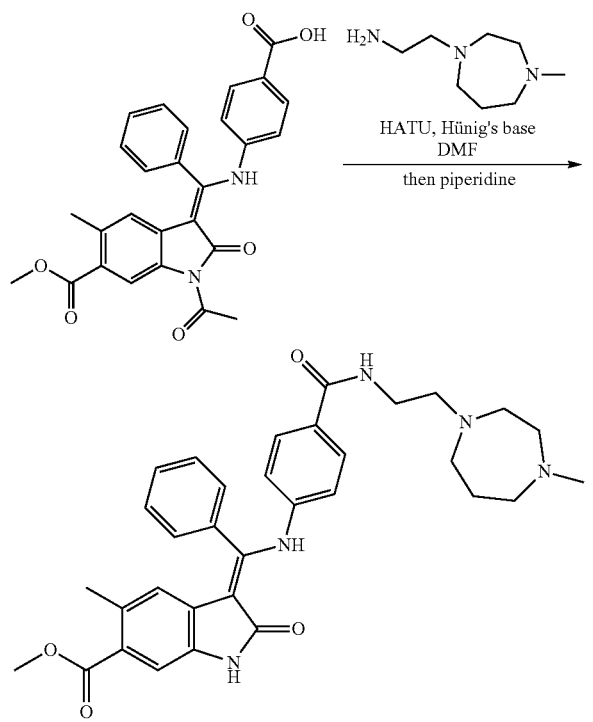

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 μl, 1.03 mmol) and 2-(4-methyl-1,4-diazepan-1-yl)ethanamine (54.5 mg, 0.346 mmol) in DMF (0.5 mL) were added. The mixture was stirred at rt for 3 h and piperidine (127 μl, 1.28 mmol) was added. The mixture was stirred at rt for 18 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was purified by preparative HPLC (Method A, 10-40% MeCN in water) to afford the title compound (Z)-methyl 5-methyl-3-(((4-((2-(4-methyl-1,4-diazepan-1-yl)ethyl)carbamoyl)phenyl)amino) (phenyl)methylene)-2-oxoindoline-6-carboxylate, formate as a light yellow solid (27 mg, 34%); $R^t$ 1.29 min (Method 1); m/z 568 (M+H)$^+$ (ES$^+$); $^1$H NMR δ: 1.68-1.77 (2H, overlapping m), 2.13 (3H, s), 2.34 (3H, s), 2.58 (2H, t), 2.61-2.74 (8H, overlapping m), 3.23-3.32 (2H, overlapping m), 3.75 (3H, s), 5.62 (1H, s), 6.87 (2H, m), 7.36 (1H, s), 7.52 (2H, m), 7.56-7.71 (5H, overlapping m), 8.20 (1H, s), 8.24 (1H, t), 10.88 (1H, s), 12.22 (1H, s).

Example 6: (Z)-Methyl 3-(((4-((2-(4-(dimethylamino)piperidin-1-yl)ethyl)carbamoyl)phenyl)amino) (phenyl)methylene)-5-methyl-2-oxoindoline-6-carboxylate, formate

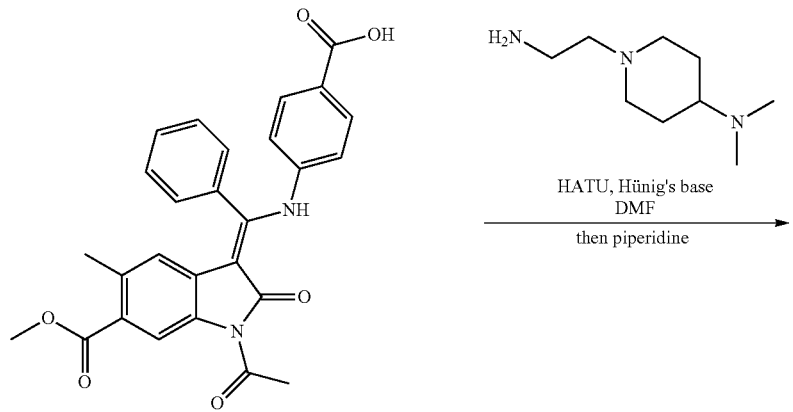

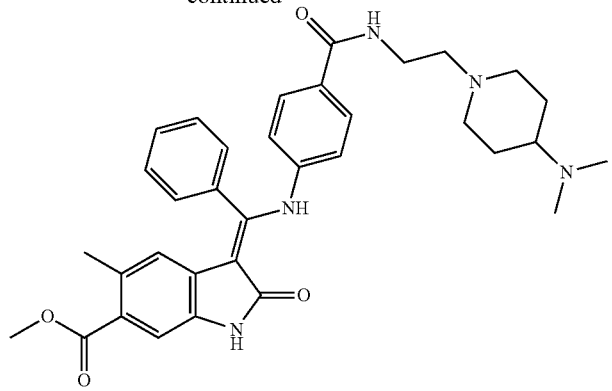

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 1-(2-aminoethyl)-N,N-dimethylpiperidin-4-amine (59.3 mg, 0.346 mmol) in DMF (0.2 mL) were added. The mixture was stirred at rt for 3 h and piperidine (127 µl, 1.28 mmol) was added. The mixture was stirred at rt for 1 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was purified by preparative HPLC (Method A, 10-40% MeCN in water) to afford the title compound (Z)-methyl 3-(((4-((2-(4-(dimethylamino)piperidin-1-yl)ethyl)carbamoyl)phenyl)amino)(phenyl)methylene)-5-methyl-2-oxoindoline-6-carboxylate, formate as a light yellow solid (20 mg, 24%); R$^t$ 1.26 min (Method 1); m/z 582 (M+H)$^+$ (ES$^+$); $^1$H NMR δ: 1.29-1.44 (2H, overlapping m), 1.65-1.77 (2H, overlapping m), 1.86-1.98 (2H, overlapping m), 2.14 (3H, s), 2.24 (6H, s), 2.40 (2H, t), 2.85-2.95 (2H, overlapping m), 3.76 (3H, s), 5.62 (1H, s), 6.88 (2H, m), 7.37 (1H, s), 7.53 (2H, m), 7.57-7.70 (5H, overlapping m), 8.22 (1H, s), 8.28 (1H, t), 10.89 (1H, s), 12.23 (1H, s). (Missing 3H-presumed obscured by solvent).

Example 7: (Z)-Methyl 3-(((4-((2-(4-(2-hydroxyethyl)piperazin-1-yl)-2-oxoethyl)carbamoyl)phenyl)amino) (phenyl)methylene)-5-methyl-2-oxoindoline-6-carboxylate, formate

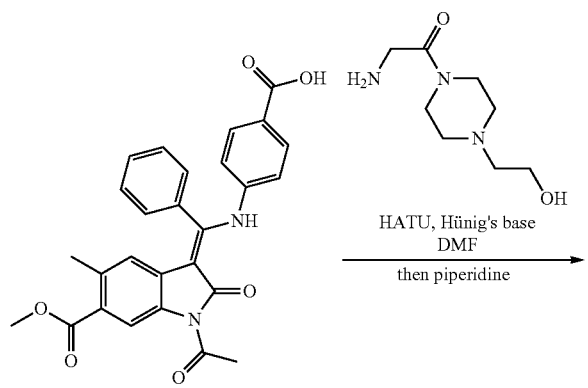

HATU, Hünig's base
DMF
————————→
then piperidine

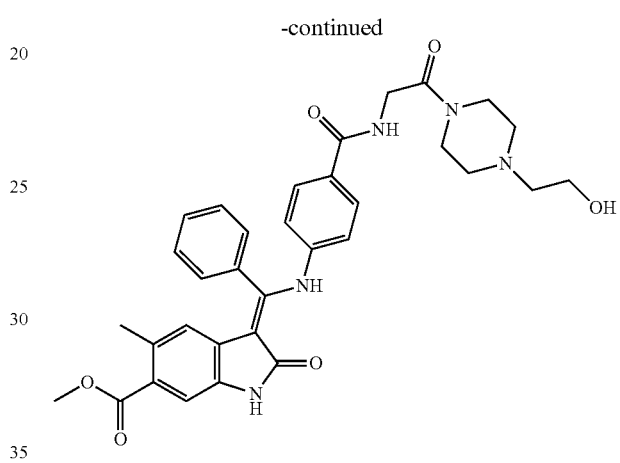

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 2-amino-1-(4-(2-hydroxyethyl)piperazin-1-yl)ethanone, 2HCl (90 mg, 0.346 mmol) were added. The mixture was stirred at rt for 3 h and piperidine (127 µl, 1.28 mmol) was added. The mixture was stirred at rt for 18 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 3-(((4-((2-(4-(2-hydroxyethyl)piperazin-1-yl)-2-oxoethyl)carbamoyl)phenyl)amino) (phenyl)methylene)-5-methyl-2-oxoindoline-6-carboxylate, formate as a light yellow solid (24 mg, 27%); R$^t$ 1.51 min (Method 1); m/z 598 (M+H)$^+$ (ES$^+$); $^1$H NMR δ: 2.14 (3H, s), 2.90-3.58 (8H, overlapping m), 3.68-3.79 (5H, overlapping m), 4.00-4.45 (4H, overlapping m), 5.40 (1H, br s), 5.63 (1H, s), 6.90 (2H, m), 7.37 (1H, s), 7.53 (2H, m), 7.57-7.70 (5H, overlapping m), 8.52 (1H, s), 9.63 (1H, br s), 10.89 (1H, s), 12.23 (1H, s).

Example 8: (Z)-Methyl 5-methyl-3-(((4-((2-(4-methylpiperazin-1-yl)-2-oxoethyl)carbamoyl)phenyl)amino) (phenyl)methylene)-2-oxoindoline-6-carboxylate, 0.5 formate Example 9: (Z)-Methyl 5-methyl-2-oxo-3-(((4-((2-(3-oxopiperazin-1-yl)ethyl)carbamoyl)phenyl)amino) (phenyl)methylene)indoline-6-carboxylate

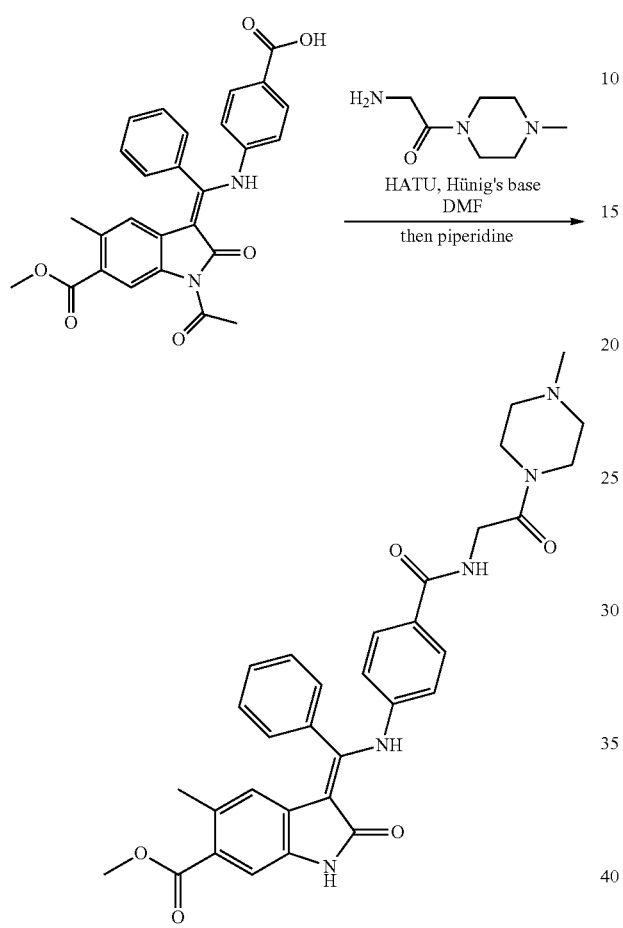

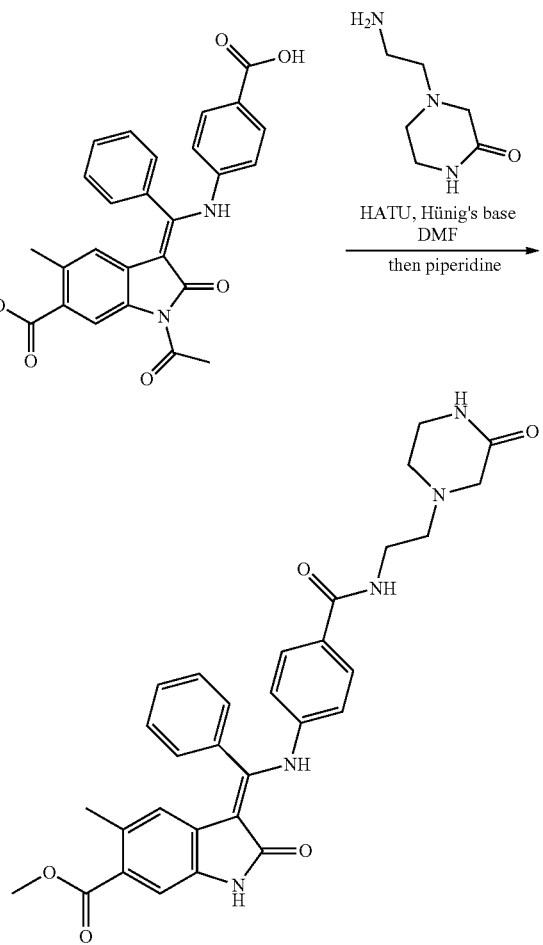

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 2-amino-1-(4-methylpiperazin-1-yl)ethanone, 2HCl (80 mg, 0.346 mmol) were added. The mixture was stirred at rt for 3 h and piperidine (127 µl, 1.28 mmol) was added. The mixture was stirred at rt for 18 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 5-methyl-3-(((4-((2-(4-methylpiperazin-1-yl)-2-oxoethyl)carbamoyl)phenyl)amino) (phenyl)methylene)-2-oxoindoline-6-carboxylate, 0.5 formate as a light yellow solid (28 mg, 36%); R$^t$ 1.52 min (Method 1); m/z 568 (M+H)$^+$ (ES$^+$); $^1$H NMR δ: 2.14 (3H, s), 2.26 (3H, s), 2.31-2.46 (4H, overlapping m), 3.41-3.54 (4H, overlapping m), 3.76 (3H, s), 4.06 (2H, d), 5.64 (1H, s), 6.89 (2H, m), 7.37 (1H, s), 7.53 (2H, m), 7.57-7.70 (5H, overlapping m), 8.13 (0.5H, s), 8.46 (1H, t), 10.89 (1H, s), 12.23 (1H, s).

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 4-(2-aminoethyl)piperazin-2-one (49.6 mg, 0.346 mmol) were added. The mixture was stirred at rt for 3 h and piperidine (127 µl, 1.28 mmol) was added. The mixture was stirred at rt for 18 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 5-methyl-2-oxo-3-(((4-((2-(3-oxopiperazin-1-yl)ethyl)carbamoyl)phenyl)amino) (phenyl)methylene)indoline-6-carboxylate as a light yellow solid (43 mg, 58%); R$^t$ 1.59 min (Method 1); m/z 554 (M+H)$^+$ (ES$^+$); $^1$H NMR δ: 2.14 (3H, s), 2.40-2.63 (2H, overlapping m), 2.96 (1H, m), 3.13 (1H, m), 3.20-3.48 (4H, overlapping m), 3.58 (1H, m), 3.75 (3H, s), 3.99 (1H, m), 5.62 (1H, s), 6.89 (2H, m), 7.36 (1H, s), 7.53 (2H, m), 7.57-7.69 (5H, overlapping m), 8.27-8.63 (2H, overlapping m), 10.89 (1H, s), 12.23 (1H, s).

Example 10: (Z)-Methyl 5-methyl-3-(((4-((3-(4-methylpiperazin-1-yl)-3-oxopropyl)carbamoyl)phenyl)amino) (phenyl)methylene)-2-oxoindoline-6-carboxylate

Example 11: (Z)-Methyl 5-methyl-3-(((4-(4-(2-(methylamino)-2-oxoethyl)piperazine-1-carbonyl) phenyl)amino) (phenyl)methylene)-2-oxoindoline-6-carboxylate

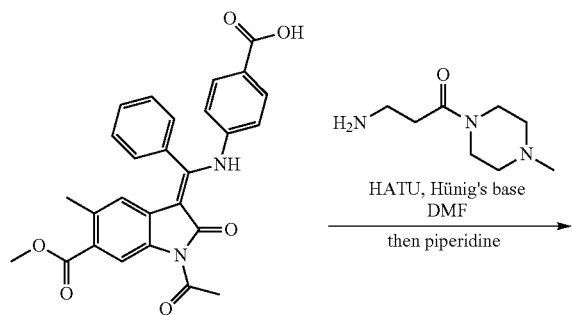

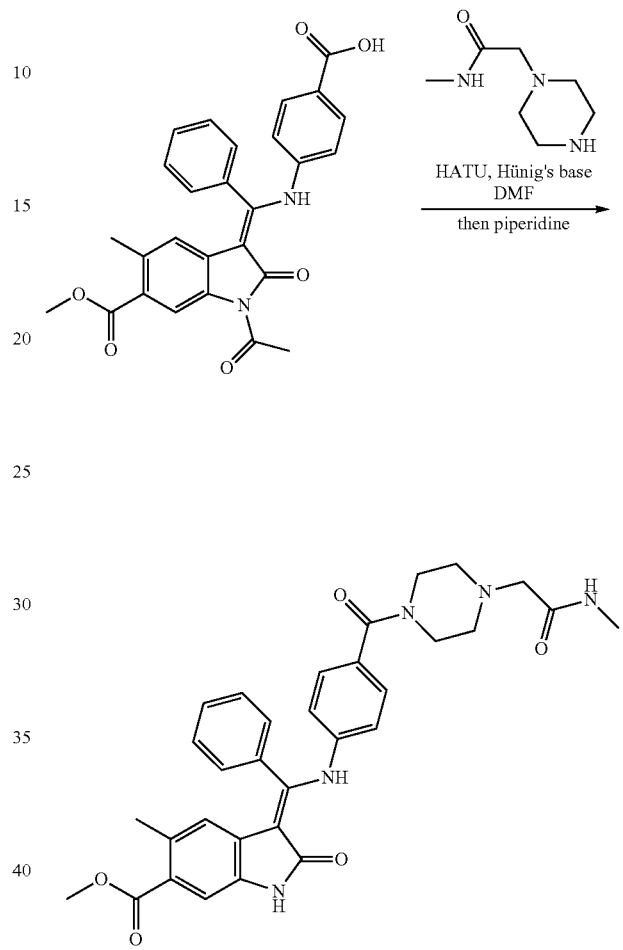

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (800 mg, 1.37 mmol), and HATU (781 mg, 2.05 mmol) in DMF (6 mL) were stirred at rt for 10 min then Hünig's base (1.43 ml, 8.21 mmol) and 3-amino-1-(4-methylpiperazin-1-yl)propan-1-one (223 mg, 1.30 mmol) was added. The mixture was stirred at rt for 3 h and piperidine (1.35 ml, 13.7 mmol) was added. The mixture was stirred at rt for 18 h. The reaction mixture was partitioned between 10% MeOH in DCM (25 mL) and saturated aqueous $NaHCO_3$ solution (10 mL). The organic layer was washed with brine (10 mL) and the solvent was evaporated under reduced pressure. The material was loaded onto an SCX cartridge in MeOH (10 mL). The column was washed with MeOH (30 mL) and the filtrate was discarded. The product was eluted with 1% ammonia in MeOH. The solvent was evaporated and the residue was purified by flash column chromatography ($SiO_2$, 80 g, 0-30% 1% ammonia in MeOH in DCM, gradient elution) to afford (Z)-methyl 5-methyl-3-(((4-((3-(4-methylpiperazin-1-yl)-3-oxopropyl)carbamoyl)phenyl)amino) (phenyl)methylene)-2-oxoindoline-6-carboxylate as a light yellow solid (386 mg, 48%); $R^t$ 1.60 min (Method 1); m/z 582 $(M+H)^+$ $(ES^+)$; $^1H$ NMR δ: 2.13 (3H, s), 2.15 (3H, s), 2.21 (2H, t), 2.24 (2H, t), 2.53 (2H, t), 3.35-3.45 (6H, overlapping m), 3.75 (3H, s), 5.62 (1H, s), 6.87 (2H, m), 7.36 (1H, s), 7.51 (2H, m), 7.57-7.68 (5H, overlapping m), 8.37 (1H, t), 10.88 (1H, s), 12.21 (1H, s).

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 μl, 1.03 mmol) and N-methyl-2-(piperazin-1-yl)acetamide (54.5 mg, 0.346 mmol) were added. The mixture was stirred at rt for 3 h and piperidine (127 μl, 1.28 mmol) was added. The mixture was stirred at rt for 18 h. The reaction mixture was partitioned between DCM (25 mL) and saturated aqueous $NaHCO_3$ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 5-methyl-3-(((4-(4-(2-(methylamino)-2-oxoethyl)piperazine-1-carbonyl)phenyl)amino) (phenyl)methylene)-2-oxoindoline-6-carboxylate as a light yellow solid (8.8 mg, 12%); $R^t$ 1.59 min (Method 1); m/z 568 $(M+H)^+$ $(ES^+)$; $^1H$ NMR δ: 2.13 (3H, s), 2.61-2.70 (4H, overlapping m), 3.75 (3H, s), 5.60 (1H, s), 6.88 (2H, m), 7.24 (2H, m), 7.37 (1H, s), 7.53 (2H, m), 7.57-7.71 (3H, overlapping m), 8.26 (1H, br s), 10.87 (1H, s), 12.23 (1H, s). (Missing 9H-presumed obscured by solvent).

Example 12: (Z)-Methyl 3-(((4-((2-(4-hydroxypiperidin-1-yl)ethyl)carbamoyl)phenyl)amino)(phenyl)methylene)-5-methyl-2-oxoindoline-6-carboxylate, 0.8 formate

Example 13: (Z)-Methyl 3-(((4-((1-(2-hydroxyethyl)piperidin-4-yl)carbamoyl)phenyl)amino) (phenyl)methylene)-5-methyl-2-oxoindoline-6-carboxylate

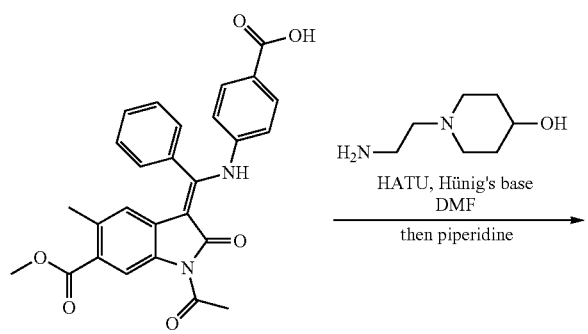

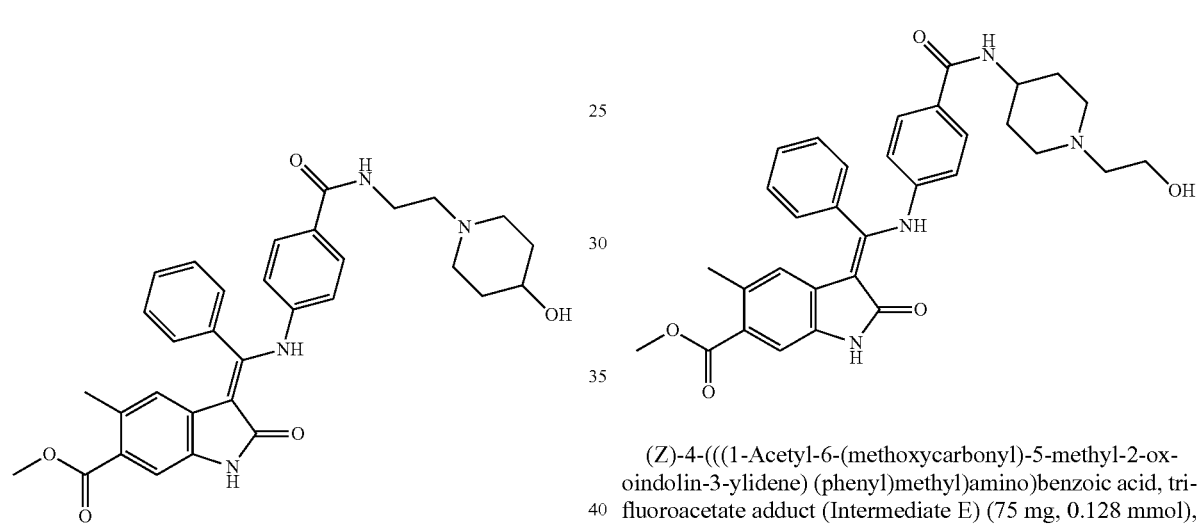

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 1-(2-aminoethyl)piperidin-4-ol (50 mg, 0.346 mmol) were added. The mixture was stirred at rt for 3 h and piperidine (127 µl, 1.28 mmol) was added. The mixture was stirred at rt for 18 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was purified by preparative HPLC (Method A, 20-50% MeCN in water) to afford the title compound (Z)-methyl 3-(((4-((2-(4-hydroxypiperidin-1-yl)ethyl)carbamoyl)phenyl)amino) (phenyl)methylene)-5-methyl-2-oxoindoline-6-carboxylate, 0.8 formate as a light yellow solid (9 mg, 11%); R$^t$ 1.54 min (Method 1); m/z 555 (M+H)$^+$ (ES$^+$); $^1$H NMR δ: 1.28-1.42 (2H, overlapping m), 1.64-1.72 (2H, overlapping m), 2.02-2.11 (2H, overlapping m), 2.13 (3H, s), 2.42 (2H, t), 2.69-2.78 (2H, overlapping m), 3.75 (3H, s), 4.56 (1H, br s), 5.62 (1H, s), 6.87 (2H, m), 7.36 (1H, s), 7.52 (2H, m), 7.57-7.69 (5H, overlapping m), 8.16 (0.8H, s), 8.28 (1H, t), 10.88 (1H, s), 12.22 (1H, s). (Missing 3H-presumed obscured by solvent).

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 2-(4-aminopiperidin-1-yl)ethanol, 2HCl (100 mg, 0.462 mmol) in DMF (1 mL) were added. The mixture was stirred at rt for 2 h and piperidine (127 µl, 1.28 mmol) was added. The mixture was stirred at rt for 18 h. The reaction mixture was partitioned between DCM (25 mL) and saturated aqueous NaHCO$_3$ solution (10 mL). The organic layer was washed with brine (10 mL) and the solvent was evaporated under reduced pressure. The crude product was loaded onto a column of SCX (2 g) in 5% AcOH in MeOH (10 mL). The column was washed with MeOH (10 mL) and the filtrate was discarded. The product was eluted with 1% ammonia in MeOH (25 mL). The solvent was evaporated under reduced pressure and the product was purified by flash column chromatography (SiO$_2$, 12 g, 0-30% MeOH in DCM, gradient elution) to afford (Z)-methyl 3-(((4-((1-(2-hydroxyethyl)piperidin-4-yl)carbamoyl)phenyl)amino)(phenyl)methylene)-5-methyl-2-oxoindoline-6-carboxylate as a light yellow solid (33 mg, 34%); R$^t$ 1.56 min (Method 1); m/z 555 (M+H)$^+$ (ES$^+$); $^1$H NMR δ: 1.43-1.56 (2H, overlapping m), 1.65-1.74 (2H, overlapping m), 2.00 (2H, t), 2.13 (3H, s), 2.36 (2H, m), 2.85 (2H, m), 3.47 (2H, m), 3.66 (1H, m), 3.75 (3H, s), 4.37 (1H, m), 5.61 (1H, s), 6.86 (2H, m), 7.36 (1H, s), 7.52 (2H, m), 7.56-7.76 (5H, overlapping m), 8.09 (1H, d), 10.88 (1H, s), 12.23 (1H, s).

Example 14: (Z)-Methyl 3-(((4-(((1-(2-hydroxyethyl)piperidin-4-yl)methyl)carbamoyl)phenyl)amino) (phenyl)methylene)-5-methyl-2-oxoindoline-6-carboxylate

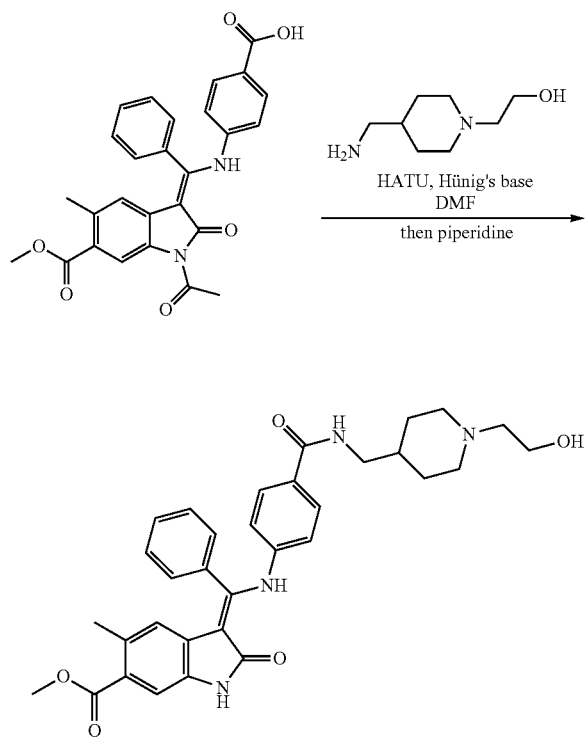

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (75 mg, 0.128 mmol), and HATU (73 mg, 0.192 mmol) in DMF (2 mL) were stirred at rt for 10 min then Hünig's base (179 µl, 1.03 mmol) and 2-(4-(aminomethyl)piperidin-1-yl)ethanol (73.1 mg, 0.462 mmol) were added. The mixture was stirred at rt for 3 h and piperidine (127 µl, 1.28 mmol) was added. The mixture was stirred at rt for 18 h. The reaction mixture was partitioned between DCM (25 mL) and saturated aqueous NaHCO₃ solution (10 mL). The organic layer was washed with brine (10 mL) and the solvent was evaporated under reduced pressure. The crude product was loaded onto a column of SCX (2 g) in 5% AcOH in MeOH (10 mL). The column was washed with MeOH (10 mL) and the filtrate was discarded. Then the product was eluted with 1% ammonia in MeOH (25 mL). The solvent was evaporated under reduced pressure and the product was purified by flash column chromatography (SiO₂, 12 g, 0-30% MeOH in DCM, gradient elution) to afford (Z)-methyl 3-(((4-(((1-(2-hydroxyethyl)piperidin-4-yl)methyl)carbamoyl)phenyl)amino) (phenyl)methylene)-5-methyl-2-oxoindoline-6-carboxylate as a light yellow solid (63 mg, 63%); R$^t$ 1.56 min (Method 1); m/z 569 (M+H)⁺ (ES⁺); ¹H NMR δ: 1.05-1.19 (2H, overlapping m), 1.47 (1H, m), 1.58 (2H, m), 1.81-1.94 (2H, overlapping m), 2.13 (3H, s), 2.28-2.40 (2H, overlapping m), 2.82 (2H, m), 3.07 (2H, t), 3.46 (2H, m), 3.75 (3H, s), 4.34 (1H, s), 5.61 (1H, s), 6.86 (2H, m), 7.36 (1H, s), 7.52 (2H, m), 7.57-7.70 (5H, m), 8.32 (1H, t), 10.88 (1H, s), 12.23 (1H, s).

Route 1C

Example 15: (Z)-Methyl 3-(((4-(4-(2-((2-hydroxyethyl)amino)-2-oxoethyl)piperazine-1-carbonyl)phenyl)amino) (phenyl)methylene)-5-methyl-2-oxoindoline-6-carboxylate Intermediate F: (Z)-Methyl 1-acetyl-3-(((4-(4-(2-(tert-butoxy)-2-oxoethyl)piperazine-1-carbonyl)phenyl)amino) (phenyl)methylene)-5-methyl-2-oxoindoline-6-carboxylate

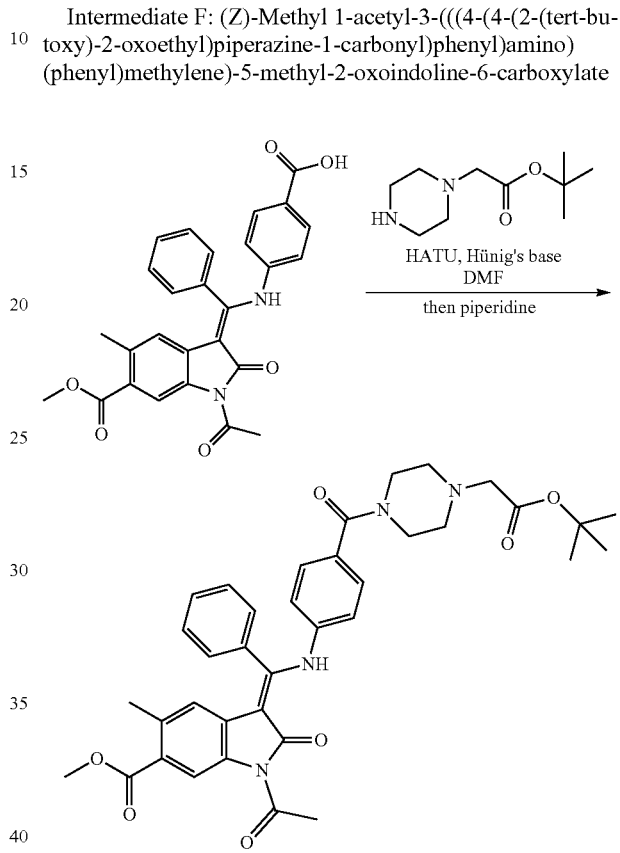

(Z)-4-(((1-Acetyl-6-(methoxycarbonyl)-5-methyl-2-oxoindolin-3-ylidene) (phenyl)methyl)amino)benzoic acid, trifluoroacetate adduct (Intermediate E) (500 mg, 0.855 mmol), and HATU (488 mg, 1.28 mmol) in DMF (5 mL) were stirred at rt for 10 min then Hünig's base (448 µl, 2.57 mmol) and tert-butyl 2-(piperazin-1-yl)acetate (171 mg, 0.855 mmol) in DMF (1 mL) were added. The mixture was stirred at rt for 3 h. The reaction mixture was partitioned between DCM (100 mL) and saturated aqueous NaHCO₃ solution (40 mL). The organic layer was washed with brine (40 mL) and the solvent was evaporated under reduced pressure. The crude product was purified by flash column chromatography (SiO₂, 12 g, 0-30% 1% ammonia in MeOH in DCM, gradient elution) to afford the subtitle compound (Z)-methyl 1-acetyl-3-(((4-(4-(2-(tert-butoxy)-2-oxoethyl) piperazine-1-carbonyl)phenyl)amino) (phenyl)methylene)-5-methyl-2-oxoindoline-6-carboxylate as a light yellow solid (483 mg, 83%); R$^t$ 2.31 min (Method 1); m/z 653 (M+H)⁺ (ES⁺); ¹H NMR δ: 1.40 (9H, s), 2.13 (3H, s), 2.73 (3H, s), 3.13 (2H, s), 3.17-3.30 (2H, overlapping m), 3.43-3.62 (2H, overlapping m), 3.77 (3H, s), 5.49 (1H, s), 7.03 (2H, m), 7.21 (2H, m), 7.50 (2H, m), 7.57-7.68 (3H, overlapping m), 8.68 (1H, s), 11.88 (1H, s). (Missing 4H-presumed obscured by solvent).

Intermediate G: (Z)-2-(4-(4-(((1-acetyl-6-(methoxycarbonyl)-5-methyl-2-oxoindolin-3-ylidene)(phenyl)methyl)amino)benzoyl)piperazin-1-yl)acetic acid

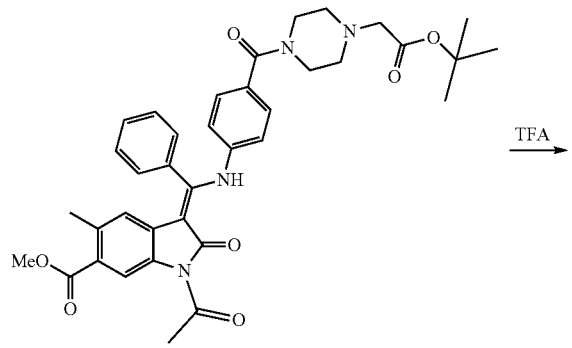

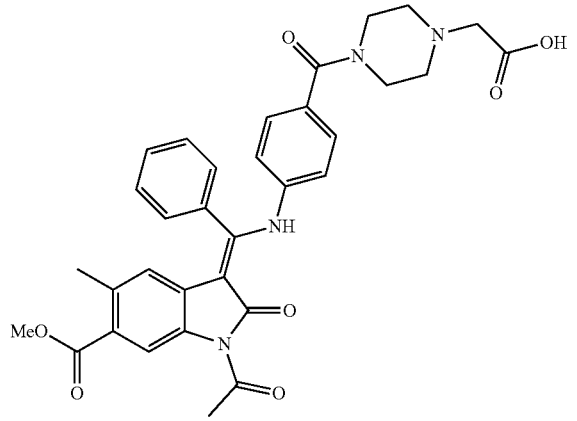

To a solution of (Z)-methyl 1-acetyl-3-(((4-(4-(2-(tert-butoxy)-2-oxoethyl)piperazine-1-carbonyl)phenyl)amino)(phenyl)methylene)-5-methyl-2-oxoindoline-6-carboxylate (Intermediate F) (481 mg, 0.737 mmol) in DCM (4.8 mL) was added TFA (568 µl, 7.37 mmol) and the mixture was stirred at rt for 16 h. Another portion of TFA (1 mL, 13.0 mmol) was added and the reaction was stirred at rt for another 3 h after which another portion of TFA (0.5 mL, 7.50 mmol) was added and the reaction was stirred at rt for another hour. The reaction mixture was added dropwise to a saturated aqueous $NaHCO_3$ solution (50 mL). The layers were separated and the organics were concentrated under reduced pressure. The solid formed in the aqueous was collected by filtration and dried under reduced pressure. Both solids were combined to afford (Z)-2-(4-(4-(((1-acetyl-6-(methoxycarbonyl)-5-methyl-2-oxoindolin-3-ylidene)(phenyl)methyl)amino)benzoyl)piperazin-1-yl)acetic acid (410 mg, 89%) as a light yellow solid; $R^t$ 1.94 min (Method 1); m/z 597 (M+H)$^+$ (ES$^+$); $^1$H NMR δ: 2.13 (3H, s), 2.73 (3H, s), 3.17 (2H, s), 3.47-3.65 (2H, overlapping m), 3.77 (3H, s), 5.50 (1H, s), 7.03 (2H, m), 7.22 (2H, m), 7.50 (2H, m), 7.55-7.68 (4H, overlapping m), 8.68 (1H, s), 11.89 (1H, s). (Missing 6H-presumed obscured by solvent).

(Z)-Methyl 3-(((4-(4-(2-((2-hydroxyethyl)amino)-2-oxoethyl)piperazine-1-carbonyl)phenyl)amino)(phenyl)methylene)-5-methyl-2-oxoindoline-6-carboxylate

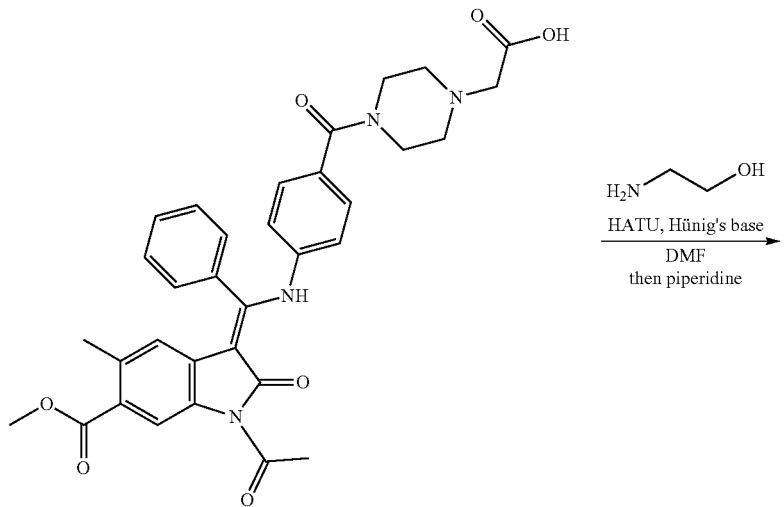

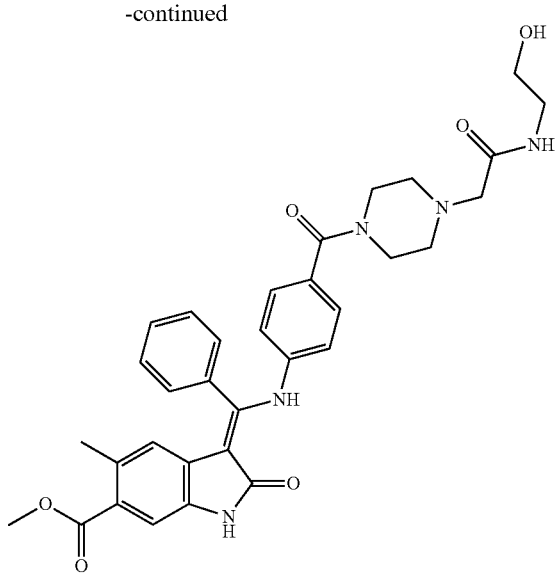

(Z)-2-(4-(4-(((1-acetyl-6-(methoxycarbonyl)-5-methyl-2-oxoindolin-3-ylidene) (phenyl)methyl)amino)benzoyl)piperazin-1-yl)acetic acid (Intermediate G) (200 mg, 0.335 mmol), and HATU (191 mg, 0.503 mmol) in DMF (2 mL) were stirred at rt for 10 min then Hünig's base (176 μl, 1.00 mmol) and 2-aminoethanol (22.52 mg, 0.369 mmol) in DMF (1 mL) were added. The mixture was stirred at rt for 4 h and piperidine (332 μl, 3.35 mmol) was added. The mixture was stirred at rt for 18 h. The reaction mixture was partitioned between DCM (25 mL) and saturated aqueous NaHCO₃ solution (10 mL). The organic layer was washed with brine (10 mL) and the solvent was evaporated under reduced pressure. The crude product was loaded onto an SCX cartridge in 5% AcOH in MeOH:MeOH:DCM (2:1:1, 20 mL). The column was washed with MeOH (30 mL) and the filtrate was discarded. The product was eluted with 1% ammonia in MeOH (25 mL). The solvent was evaporated under reduced pressure and the product was purified by flash column chromatography (SiO₂, 12 g, 0-30% 1% ammonia in MeOH in DCM, gradient elution) to afford the subtitle compound (Z)-methyl 3-(((4-(4-(2-((2-hydroxyethyl)amino)-2-oxoethyl)piperazine-1-carbonyl)phenyl)amino) (phenyl)methylene)-5-methyl-2-oxoindoline-6-carboxylate (81 mg, 39%) was obtained as a light yellow solid; R$^t$ 1.57 min (Method 1); m/z 598 (M+H)$^+$ (ES$^+$); $^1$H NMR δ: 2.13 (3H, s), 2.33-2.47 (4H, overlapping m), 2.93 (2H, s), 3.16 (2H, q), 3.39 (2H, q), 3.75 (3H, s), 4.68 (1H, t), 5.60 (1H, s), 6.87 (2H, m), 7.19 (2H, m), 7.36 (1H, s), 7.52 (2H, m), 7.57-7.68 (3H, overlapping m), 7.72 (1H, s), 10.85 (1H, s), 12.21 (1H, s). (Missing 4H-presumed obscured by solvent).

The following compound examples (Table 2) may be prepared by similar synthetic methods to the aforementioned examples or by methods described elsewhere herein:

TABLE 2

Additional Compound Examples of the Invention

Example No., Structure, Name, Route code, LC-MS Analysis and $^1$H NMR Spectral Data Example 16:

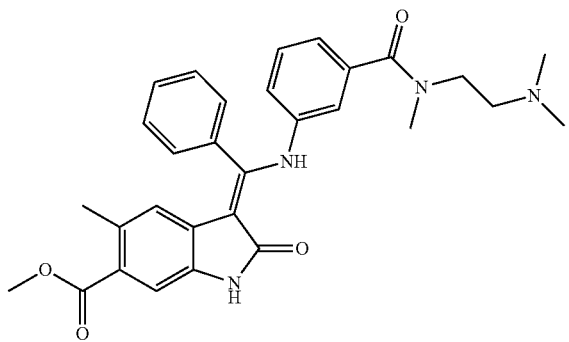

(Z)-Methyl 3-(((3-((2-(dimethylamino)ethyl)(methyl)carbamoyl)phenyl)amino)(phenyl)methylene)-5-methyl-2-oxoindoline-6-carboxylate
Route code*: 1B R$^t$ 1.59 min (Method 1); m/z 513 (M + H)$^+$ (ES$^+$); $^1$H NMR (mixture of rotamers) δ: 1.89 (3H, s), 2.13 (3H, s), 2.15-2.26 (4H, overlapping m), 2.34-2.44 (1H, m), 2.57 (1.5H, s), 2.87 (1.5H, s), 2.88-2.96 (1H, m), 3.39-3.49 (1H, m), 3.75 (3H, s), 5.57 (1H, s), 6.77 (0.5H, s), 6.85 (0.5H, s), 7.02 (2H, d), 7.26 (1H, t), 7.36 (1H, s), 7.49-7.51 (2H, overlapping m), 7.54-7.66 (3H, overlapping m), 10.83 (1H, s), 12.13 (1H, s).

TABLE 2-continued

Additional Compound Examples of the Invention

Example No., Structure, Name, Route code, LC-MS Analysis and $^1$H NMR Spectral Data Example 17:

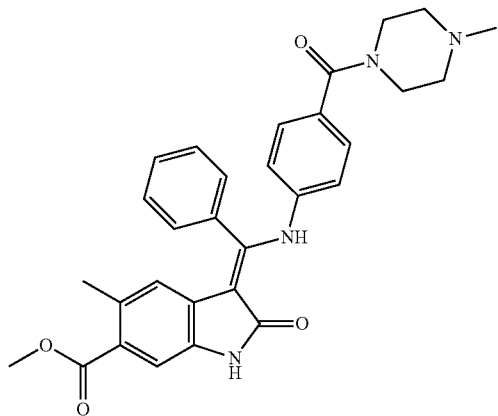

(Z)-Methyl 5-methyl-3-(((4-(4-methylpiperazine-1-carbonyl)phenyl)amino)(phenyl)methylene)-2-oxoindoline-6-carboxylate
Route code*: 1B R$^t$ 1.56 min (Method 1); m/z 511 (M + H)$^+$ (ES$^+$); $^1$H NMR δ: 2.13 (3H, s), 2.16 (3H, s), 2.19-2.31 (4H, overlapping m), 3.75 (3H, s), 5.60 (1H, s), 6.87 (2H, m), 7.18 (2H, m), 7.36 (1H, s), 7.52 (2H, m), 7.56-7.68 (3H, overlapping m), 10.85 (1H, s), 12.21 (1H, s). (Missing 4H-presumed obscured by solvent).

Example 18:

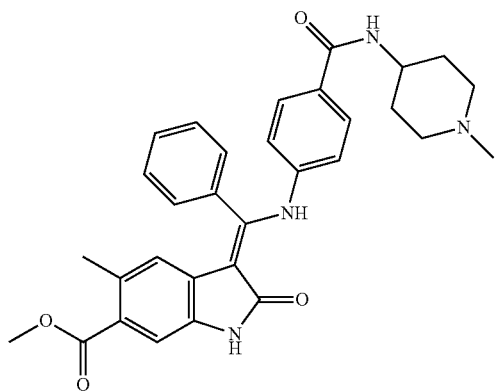

(Z)-Methyl-5-methyl-3-(((4-((1-methylpiperidin-4-yl)carbamoyl)phenyl)amino)(phenyl)methylene)-2-oxoindoline-6-carboxylate, formate
Route code*: 1B R$^t$ 1.54 min (Method 1); m/z 525 (M + H)$^+$ (ES$^+$); $^1$H NMR δ: 1.60-1.75 (2H, overlapping m), 1.91-2.02 (2H, overlapping m), 2.13 (3H, s), 2.71-2.79 (3H, overlapping m), 2.98-3.13 (2H, overlapping m), 3.40-3.47 (2H, overlapping m), 3.75 (3H, s), 3.94 (1H, m), 5.62 (1H, s), 6.86 (2H, m), 7.36 (1H, s), 7.54 (2H, m), 7.57-7.71 (5H, overlapping m), 8.30 (1H, d), 9.16 (1H, s), 10.89 (1H, s), 12.24 (1H, s).

Example 19:

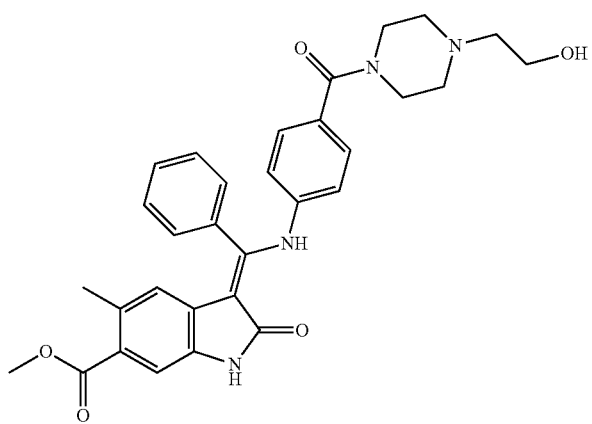 [SMILES: COC(=O)c1cc2c(cc1C)/C(=C(/Nc1ccc(C(=O)N3CCN(CCO)CC3)cc1)c1ccccc1)C(=O)N2]

R$^t$ 1.49 min (Method 1); m/z 541 (M + H)$^+$ (ES$^+$); $^1$H NMR δ: 2.14 (3H, s), 2.28-2.45 (6H, overlapping m), 3.49 (3H, t), 3.76 (3H, s), 4.43 (1H, s), 5.60 (1H, s), 6.80-6.91 (2H, overlapping m), 7.13-7.23 (2H, overlapping m), 7.37 (1H, s), 7.53 (2H, overlapping m), 7.57-7.70 (3H, overlapping m), 8.16 (0.5H, s), 10.86 (1H, s), 12.22 (1H, s). (Missing 3H-presumed obscured by solvent)

| | |
|---|---|
| (Z)-Methyl 3-(((4-(4-(2-hydroxyethyl)piperazine-1-carbonyl)phenyl)amino)(phenyl)methylene)-5-methyl-2-oxoindoline-6-carboxylate, 0.5 formate<br>Route code*: 1B<br>Example 20:<br>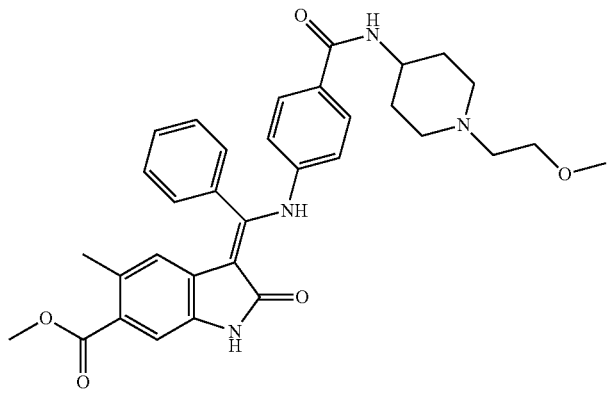 | $R^t$ 1.58 min (Method 1); m/z 569 (M + H)$^+$ (ES$^+$); $^1$H NMR δ: 1.66-1.83 (2H, overlapping m), 1.89-2.03 (2H, overlapping m), 2.13 (3H, s), 2.99-3.14 (2H, overlapping m), 3.45-3.55 (2H, overlapping m), 3.65 (2H, t), 3.75 (3H, s), 3.94 (1H, m), 5.61 (1H, s), 6.87 (2H, m), 7.36 (1H, s), 7.53 (2H, m), 7.57-7.72 (5H, overlapping m), 8.33 (1H, d), 10.89 (1H, s), 12.23 (1H, s). (Missing 5H-presumed obscured by solvent). |
| (Z)-Methyl 3-(((4-((1-(2-methoxyethyl)piperidin-4-yl)carbamoyl)phenyl)amino)(phenyl)methylene)-5-methyl-2-oxoindoline-6-carboxylate<br>Route code*: 1B<br>Example 21:<br>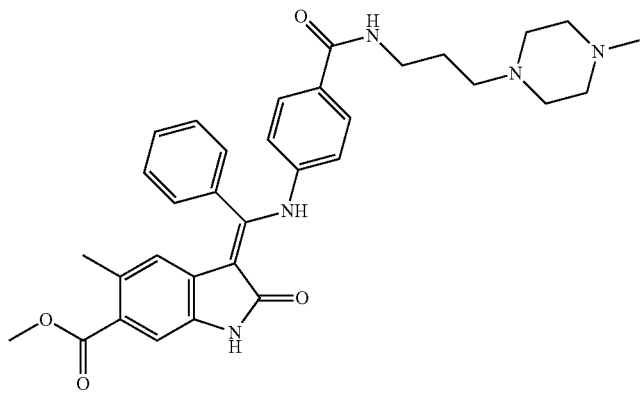 | $R^t$ 1.40 min (Method 1); m/z 568 (M + H)$^+$ (ES$^+$); $^1$H NMR δ: 1.54-1.68 (2H, overlapping m), 2.13 (3H, s), 2.14 (3H, s), 2.20-2.41 (8H, overlapping m), 3.16-3.25 (2H, overlapping m), 3.75 (3H, s), 5.61 (1H, s), 6.85 (2H, m), 7.36 (1H, s), 7.53 (2H, m), 7.56-7.70 (5H, overlapping m), 8.19 (1H, s), 8.35 (1H, t), 10.88(1H, s), 12.23(1H s). (Missing 2H-presumed obscured by solvent). |
| (Z)-Methyl-5-methyl-3-(((4-((3-(4-methylpiperazin-1-yl)propyl)carbamoyl)phenyl)amino)(phenyl)methylene)-2-oxoindoline-6-carboxylate, formate<br>Route code*: 1B<br>Example 22:<br>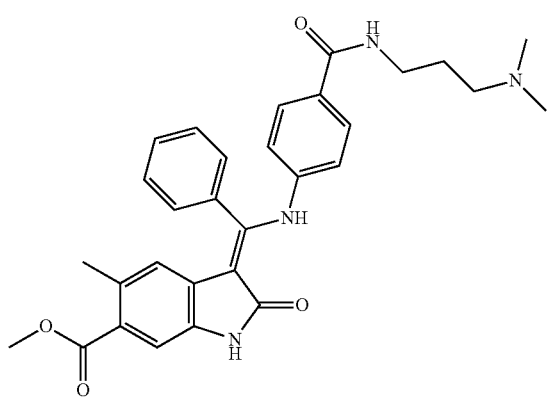 | $R^t$ 1.53 min (Method 1); m/z 513 (M + H)$^+$ (ES$^+$); $^1$H NMR δ: 1.65 (2H, m), 2.13 (3H, s), 2.30 (6H, s), 2.46 (2H, t), 3.22 (2H, m), 3.75 (3H, s), 5.61 (1H, s), 6.87 (2H, m), 7.36 (1H, s), 7.53 (2H, m), 7.58-7.70 (5H, overlapping m), 8.16 (0.5H, s), 8.39 (1H, t), 10.88 (1H, s), 12.23 (1H, s). |

TABLE 2-continued

Additional Compound Examples of the Invention

Example No., Structure, Name, Route code, LC-MS Analysis and $^1$H NMR Spectral Data (Z)-Methyl 3-(((4-((3-(dimethylamino)propyl)carbamoyl)phenyl)amino)(phenyl)methylene)-5-methyl-2-oxoindoline-6-carboxylate, 0.5 formate Route code*: 1B Example 23:

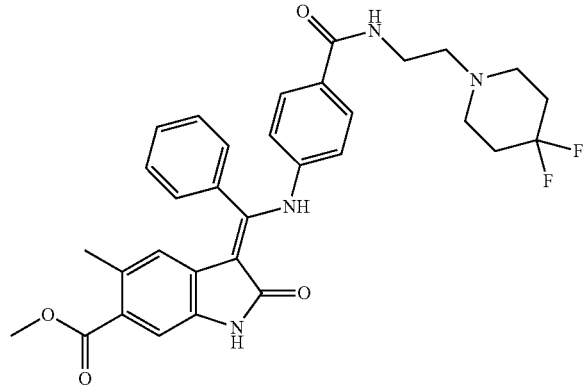 [SMILES: COC(=O)c1cc2c(cc1C)/C(=C(/Nc1ccc(C(=O)NCCN3CCC(F)(F)CC3)cc1)c1ccccc1)C(=O)N2]

R$^t$ 1.65 min (Method 1); m/z 575 (M + H)$^+$ (ES$^+$); $^1$H NMR δ: 1.93-2.32 (7H, overlapping m), 3.40-3.57 (2H, m), 3.75 (3H, s), 5.62 (1H, s), 6.89 (2H, m), 7.36 (1H, s), 7.53 (2H, m), 7.57-7.71 (5H, overlapping m), 8.47 (1H, m), 10.88 (1H, s), 12.23 (1H, s). (Missing 6H-presumed obscured by solvent).

(Z)-Methyl 3-(((4-((2-(4,4-difluoropiperidin-1-yl)ethyl)carbamoyl)phenyl)amino)(phenyl)methylene)-5-methyl-2-oxoindoline-6-carboxylate Route code*: 1B Example 24:

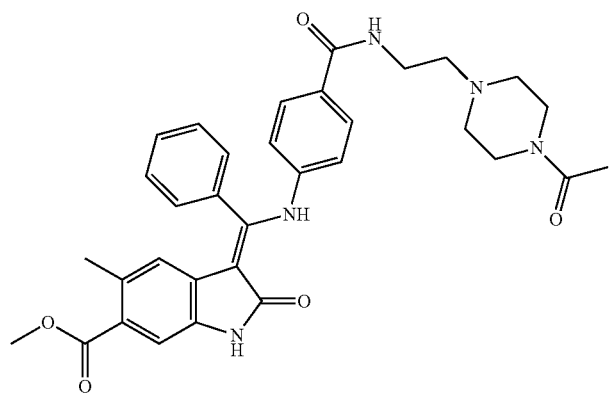 [SMILES: COC(=O)c1cc2c(cc1C)/C(=C(/Nc1ccc(C(=O)NCCN3CCN(C(C)=O)CC3)cc1)c1ccccc1)C(=O)N2]

R$^t$ 1.51 min (Method 1); m/z 582 (M + H)$^+$ (ES$^+$); $^1$H NMR δ: 2.05 (3H, s), 2.14 (3H, s), 3.76 (3H, s), 3.87-4.52 (4H, overlapping m), 5.63 (1H, s), 6.92 (2H, m), 7.37 (1H, s), 7.54 (2H, overlapping m), 7.58-7.72 (5H, overlapping m), 8.59 (1H, t), 10.90 (1H, s), 12.24 (1H, s). (Missing 8H-presumed obscured by solvent).

(Z)-Methyl 3-(((4-((2-(4-acetylpiperazin-1-yl)ethyl)carbamoyl)phenyl)amino)(phenyl)methylene)-5-methyl-2-oxoindoline-6-carboxylate Route code*: 1B Example 25:

TABLE 2-continued

Additional Compound Examples of the Invention

Example No., Structure, Name, Route code, LC-MS Analysis and $^1$H NMR Spectral Data

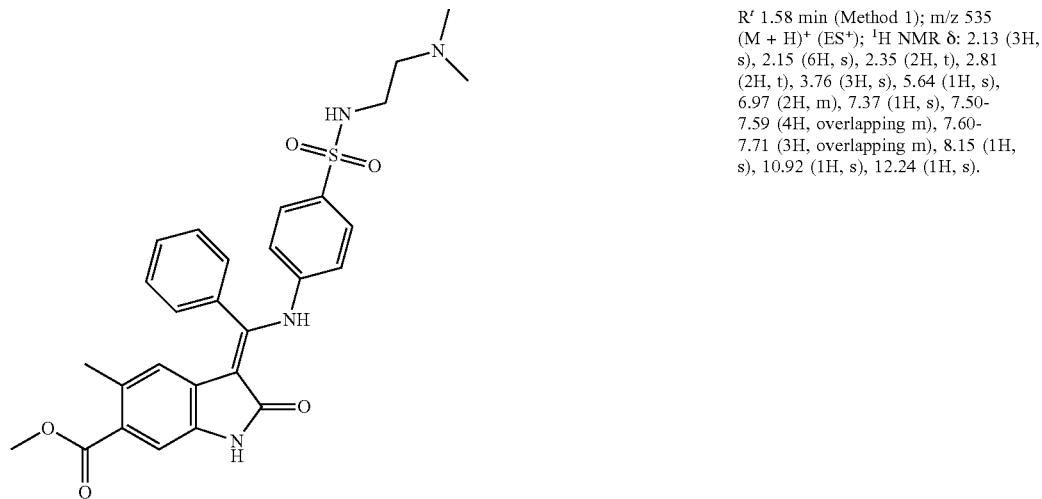

$R^t$ 1.58 min (Method 1); m/z 535 (M + H)$^+$ (ES$^+$); $^1$H NMR δ: 2.13 (3H, s), 2.15 (6H, s), 2.35 (2H, t), 2.81 (2H, t), 3.76 (3H, s), 5.64 (1H, s), 6.97 (2H, m), 7.37 (1H, s), 7.50-7.59 (4H, overlapping m), 7.60-7.71 (3H, overlapping m), 8.15 (1H, s), 10.92 (1H, s), 12.24 (1H, s).

(Z)-Methyl 3-(((4-(N-(2-(dimethylamino)ethyl)sulfamoyl)phenyl)amino)(phenyl)methylene)-5-methyl-2-oxoindoline-6-carboxylate, formate Route code*: 1A Example 26:

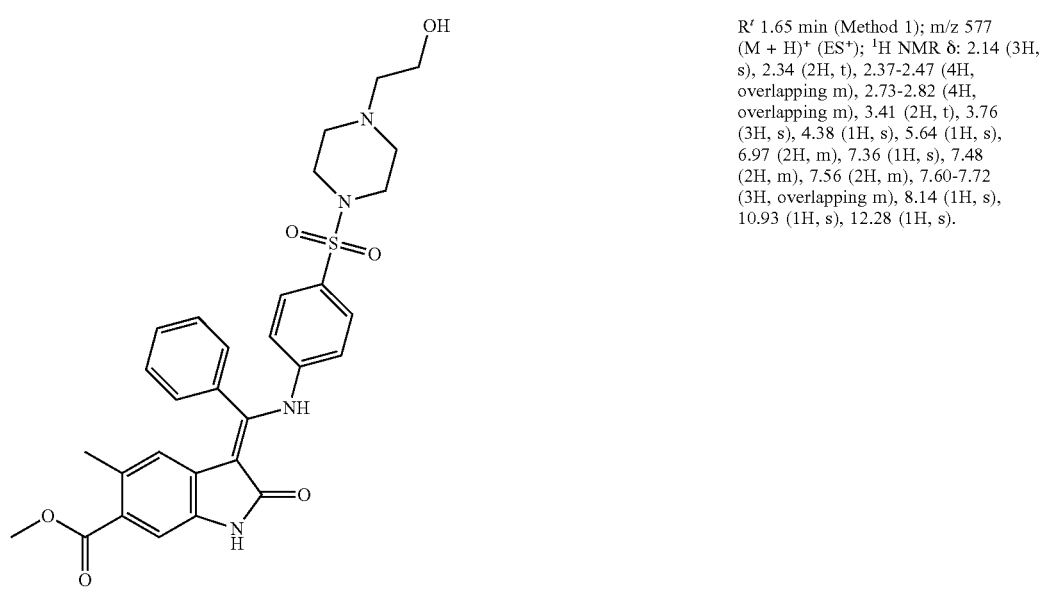

$R^t$ 1.65 min (Method 1); m/z 577 (M + H)$^+$ (ES$^+$); $^1$H NMR δ: 2.14 (3H, s), 2.34 (2H, t), 2.37-2.47 (4H, overlapping m), 2.73-2.82 (4H, overlapping m), 3.41 (2H, t), 3.76 (3H, s), 4.38 (1H, s), 5.64 (1H, s), 6.97 (2H, m), 7.36 (1H, s), 7.48 (2H, m), 7.56 (2H, m), 7.60-7.72 (3H, overlapping m), 8.14 (1H, s), 10.93 (1H, s), 12.28 (1H, s).

(Z)-Methyl 3-(((4-((4-(2-hydroxyethyl)piperazin-1-yl)sulfonyl)phenyl)amino)(phenyl)methylene)-5-methyl-2-oxoindoline-6-carboxylate, formate Route code*: 1A Example 27:

TABLE 2-continued

Additional Compound Examples of the Invention

Example No., Structure, Name, Route code, LC-MS Analysis and $^1$H NMR Spectral Data

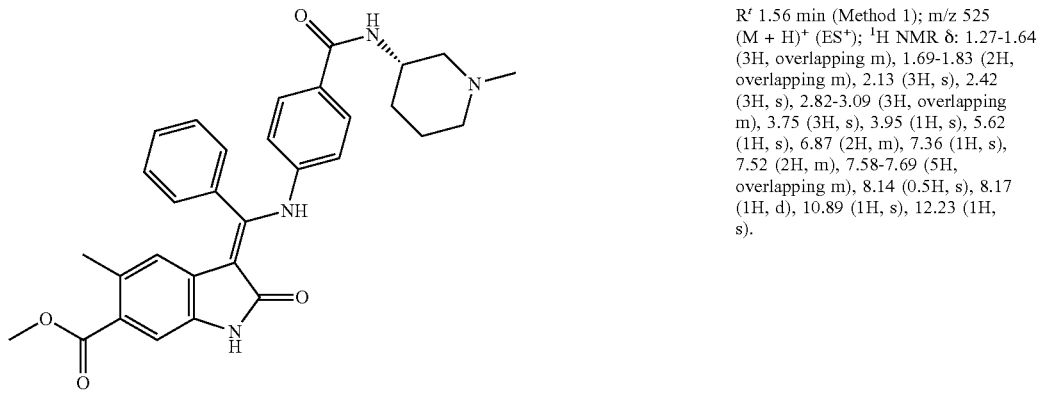

(S,Z)-Methyl 5-methyl-3-(((4-((1-methylpiperidin-3-yl)carbamoyl)phenyl)amino)(phenyl)methylene)-2-oxoindoline-6-carboxylate, 0.5 formate
Route code*: 1B $R^t$ 1.56 min (Method 1); m/z 525 (M + H)$^+$ (ES$^+$); $^1$H NMR δ: 1.27-1.64 (3H, overlapping m), 1.69-1.83 (2H, overlapping m), 2.13 (3H, s), 2.42 (3H, s), 2.82-3.09 (3H, overlapping m), 3.75 (3H, s), 3.95 (1H, s), 5.62 (1H, s), 6.87 (2H, m), 7.36 (1H, s), 7.52 (2H, m), 7.58-7.69 (5H, overlapping m), 8.14 (0.5H, s), 8.17 (1H, d), 10.89 (1H, s), 12.23 (1H, s).

Example 28:

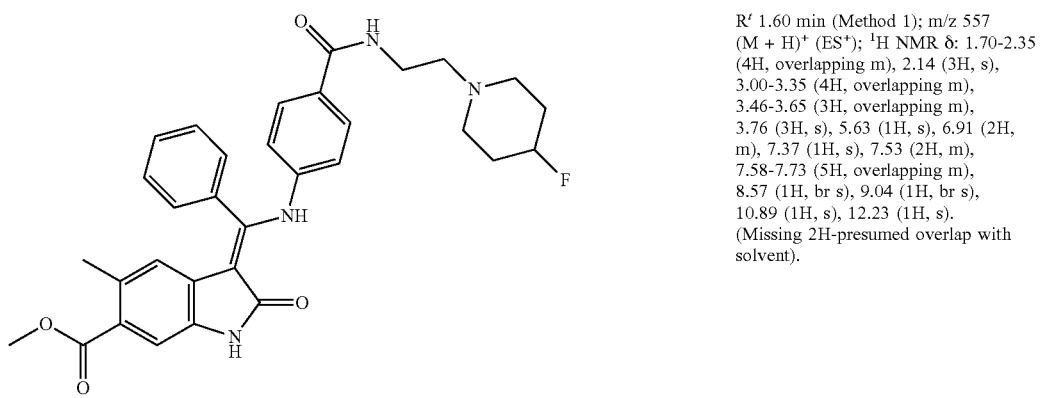

(Z)-Methyl 3-(((4-((2-(4-fluoropiperidin-1-yl)ethyl)carbamoyl)phenyl)amino)(phenyl)methylene)-5-methyl-2-oxoindoline-6-carboxylate, formate
Route code*: 1B $R^t$ 1.60 min (Method 1); m/z 557 (M + H)$^+$ (ES$^+$); $^1$H NMR δ: 1.70-2.35 (4H, overlapping m), 2.14 (3H, s), 3.00-3.35 (4H, overlapping m), 3.46-3.65 (3H, overlapping m), 3.76 (3H, s), 5.63 (1H, s), 6.91 (2H, m), 7.37 (1H, s), 7.53 (2H, m), 7.58-7.73 (5H, overlapping m), 8.57 (1H, br s), 9.04 (1H, br s), 10.89 (1H, s), 12.23 (1H, s). (Missing 2H-presumed overlap with solvent).

Example 29:

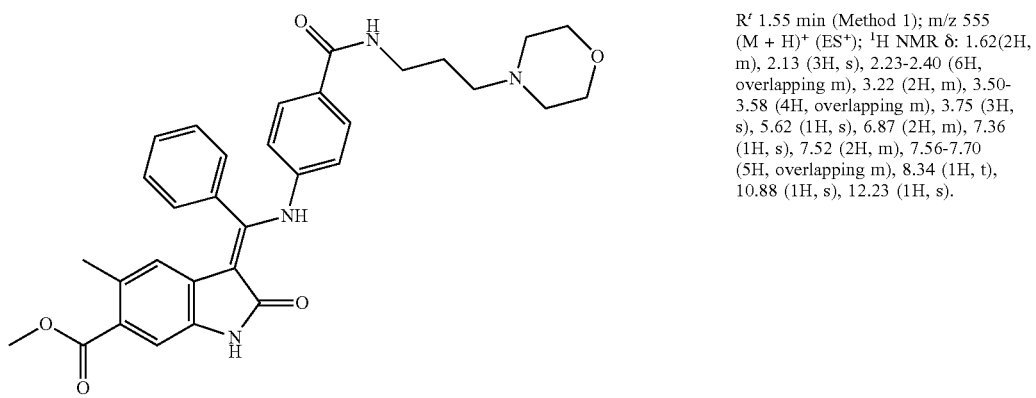

(Z)-Methyl 5-methyl-3-(((4-((3-morpholinopropyl)carbamoyl)phenyl)amino)(phenyl)methylene)-2-oxoindoline-6-carboxylate
Route code*: 1B $R^t$ 1.55 min (Method 1); m/z 555 (M + H)$^+$ (ES$^+$); $^1$H NMR δ: 1.62(2H, m), 2.13 (3H, s), 2.23-2.40 (6H, overlapping m), 3.22 (2H, m), 3.50-3.58 (4H, overlapping m), 3.75 (3H, s), 5.62 (1H, s), 6.87 (2H, m), 7.36 (1H, s), 7.52 (2H, m), 7.56-7.70 (5H, overlapping m), 8.34 (1H, t), 10.88 (1H, s), 12.23 (1H, s).

Example 30:

TABLE 2-continued

Additional Compound Examples of the Invention

Example No., Structure, Name, Route code, LC-MS Analysis and ¹H NMR Spectral Data

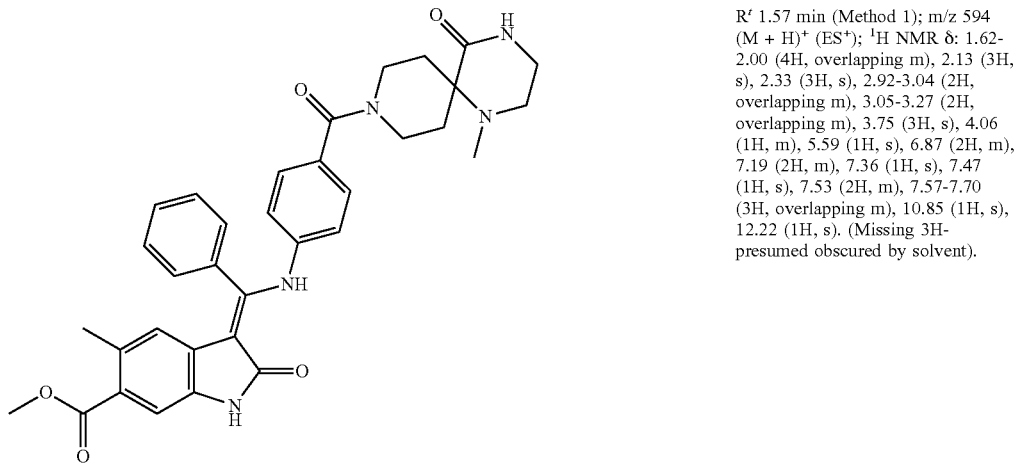

R$^t$ 1.57 min (Method 1); m/z 594 (M + H)$^+$ (ES$^+$); ¹H NMR δ: 1.62-2.00 (4H, overlapping m), 2.13 (3H, s), 2.33 (3H, s), 2.92-3.04 (2H, overlapping m), 3.05-3.27 (2H, overlapping m), 3.75 (3H, s), 4.06 (1H, m), 5.59 (1H, s), 6.87 (2H, m), 7.19 (2H, m), 7.36 (1H, s), 7.47 (1H, s), 7.53 (2H, m), 7.57-7.70 (3H, overlapping m), 10.85 (1H, s), 12.22 (1H, s). (Missing 3H-presumed obscured by solvent).

(Z)-Methyl 5-methyl-3-(((4-(1-methyl-5-oxo-1,4,9-triazaspiro[5.5]undecane-9-carbonyl)phenyl)amino)(phenyl)methylene)-2-oxoindoline-6-carboxylate Route code*: 1B Example 31:

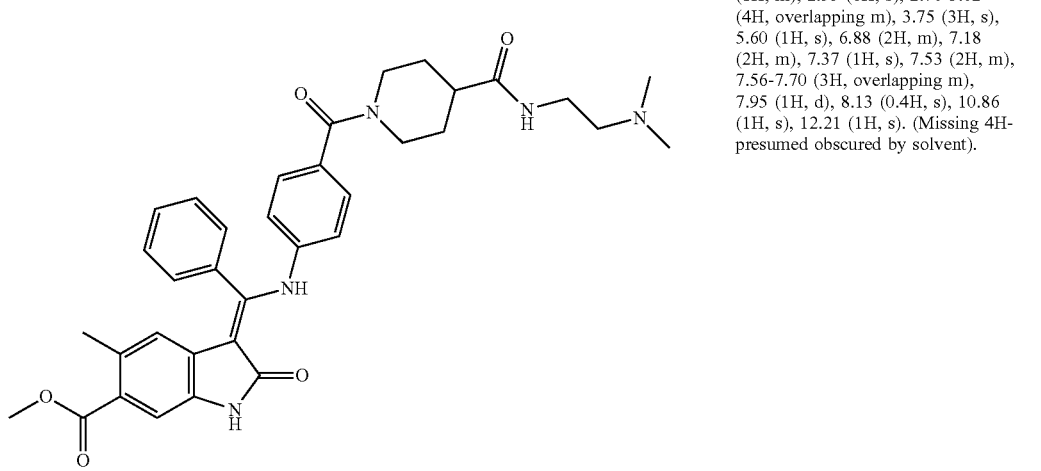

R$^t$ 1.53 min (Method 1); m/z 610 (M + H)$^+$ (ES$^+$); ¹H NMR δ: 1.36-1.52 (2H, overlapping m), 1.59-1.78 (2H, overlapping m), 2.13 (3H, s), 2.34 (1H, m), 2.55 (6H, s), 2.70-3.02 (4H, overlapping m), 3.75 (3H, s), 5.60 (1H, s), 6.88 (2H, m), 7.18 (2H, m), 7.37 (1H, s), 7.53 (2H, m), 7.56-7.70 (3H, overlapping m), 7.95 (1H, d), 8.13 (0.4H, s), 10.86 (1H, s), 12.21 (1H, s). (Missing 4H-presumed obscured by solvent).

(Z)-Methyl 3-(((4-(4-((2-(dimethylamino)ethyl)carbamoyl)piperidine-1-carbonyl)phenyl)amino)(phenyl)methylene)-5-methyl-2-oxoindoline-6-carboxylate, 0.4 formate Route code*: 1B Example 32:

TABLE 2-continued

Additional Compound Examples of the Invention

Example No., Structure, Name, Route code, LC-MS Analysis and $^1$H NMR Spectral Data

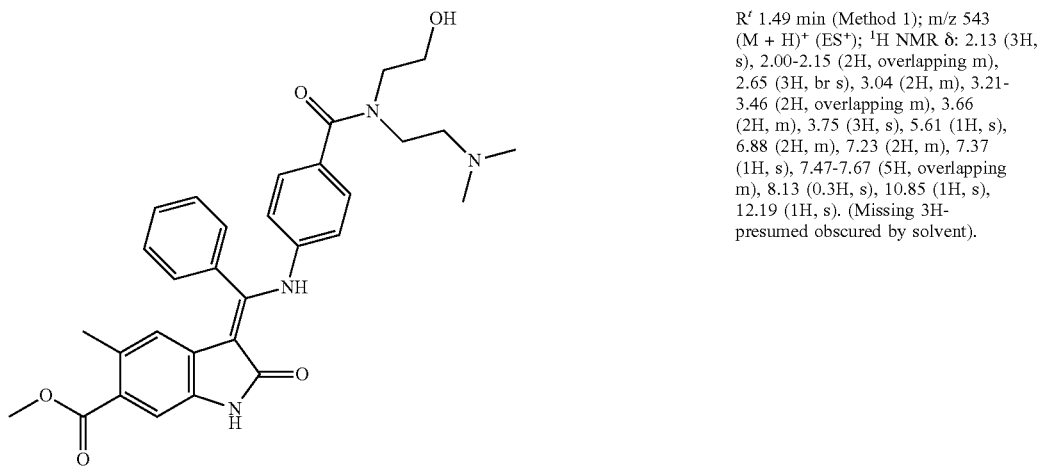

$R^t$ 1.49 min (Method 1); m/z 543 (M + H)$^+$ (ES$^+$); $^1$H NMR δ: 2.13 (3H, s), 2.00-2.15 (2H, overlapping m), 2.65 (3H, br s), 3.04 (2H, m), 3.21-3.46 (2H, overlapping m), 3.66 (2H, m), 3.75 (3H, s), 5.61 (1H, s), 6.88 (2H, m), 7.23 (2H, m), 7.37 (1H, s), 7.47-7.67 (5H, overlapping m), 8.13 (0.3H, s), 10.85 (1H, s), 12.19 (1H, s). (Missing 3H-presumed obscured by solvent).

(Z)-Methyl 3-(((4-((2-(dimethylamino)ethyl)(2-hydroxyethyl)carbamoyl)phenyl)amino)(phenyl)methylene)-5-methyl-2-oxoindoline-6-carboxylate, 0.3 formate Route code*: 1B Example 33:

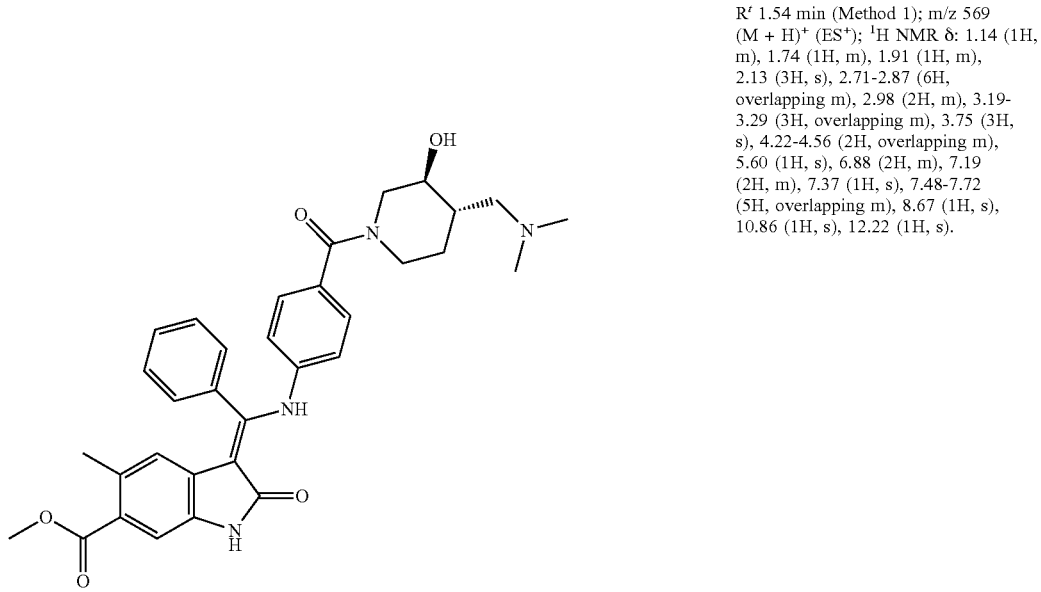

$R^t$ 1.54 min (Method 1); m/z 569 (M + H)$^+$ (ES$^+$); $^1$H NMR δ: 1.14 (1H, m), 1.74 (1H, m), 1.91 (1H, m), 2.13 (3H, s), 2.71-2.87 (6H, overlapping m), 2.98 (2H, m), 3.19-3.29 (3H, overlapping m), 3.75 (3H, s), 4.22-4.56 (2H, overlapping m), 5.60 (1H, s), 6.88 (2H, m), 7.19 (2H, m), 7.37 (1H, s), 7.48-7.72 (5H, overlapping m), 8.67 (1H, s), 10.86 (1H, s), 12.22 (1H, s).

(Z)-Methyl 3-(((4-((3S,4S)-4-((dimethylamino)methyl)-3-hydroxypiperidine-1-carbonyl)phenyl)amino)(phenyl)methylene)-5-methyl-2-oxoindoline-6-carboxylate Route code*: 1B Example 34:

TABLE 2-continued

Additional Compound Examples of the Invention

Example No., Structure, Name, Route code, LC-MS Analysis and $^1$H NMR Spectral Data

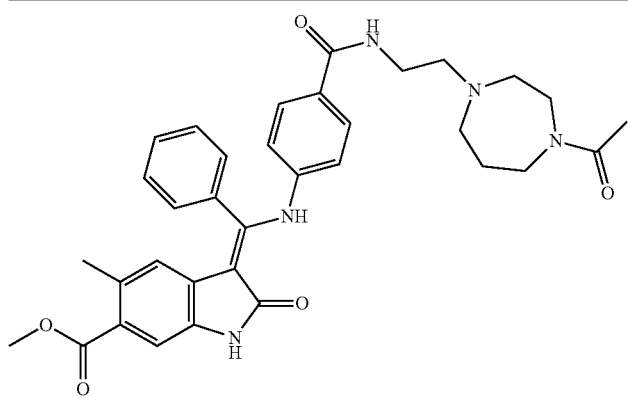 [SMILES: COC(=O)c1cc2c(cc1C)/C(=C(/Nc1ccc(C(=O)NCCN3CCCN(C(C)=O)CC3)cc1)c1ccccc1)C(=O)N2]

$R^t$ 1.55 min (Method 1); m/z 596 (M + H)$^+$ (ES$^+$); $^1$H NMR δ: 1.92-2.09 (5H, overlapping m), 2.14 (3H, s), 3.52 (6H, s), 3.76 (3H, s), 5.63 (1H, s), 6.90 (2H, m), 7.37 (1H, s), 7.53 (2H, m), 7.58-7.69 (5H, overlapping m), 8.56 (1H, s), 10.88 (1H, s), 12.23 (1H, s). (Missing 6H-presumed obscured by solvent).

(Z)-Methyl 3-(((4-((2-(4-acetyl-1,4-diazepan-1-yl)ethyl)carbamoyl)phenyl)amino)(phenyl)methylene)-5-methyl-2-oxoindoline-6-carboxylate
Route code*: 1B
Example 35:

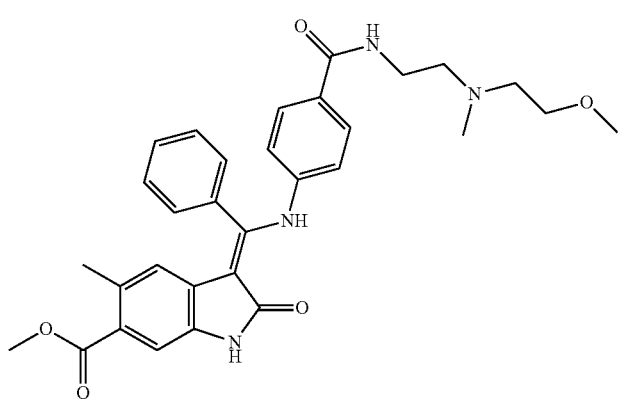

$R^t$ 1.60 min (Method 1); m/z 543 (M + H)$^+$ (ES$^+$); $^1$H NMR δ: 2.13 (3H, s), 2.38 (3H, s), 2.61-2.83 (4H, overlapping m), 3.21 (3H, s), 3.45 (2H, t), 3.75 (3H, s), 5.62 (1H, s), 6.87 (2H, m), 7.36 (1H, s), 7.52 (2H, m), 7.57-7.69 (5H, overlapping m), 8.13 (0.5 H, s), 8.30 (1H, s), 10.88 (1H, s), 12.22 (1H, s). (Missing 2H-presumed obscured by solvent.)

(Z)-Methyl 3-(((4-((2-((2-methoxyethyl)(methyl)amino)ethyl)carbamoyl)phenyl)amino)(phenyl)methylene)-5-methyl-2-oxoindoline-6-carboxylate, 0.5 formate
Route code*: 1B
Example 36:

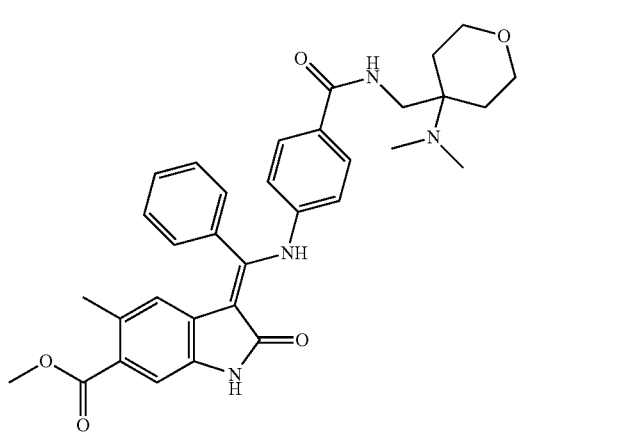 [SMILES: COC(=O)c1cc2c(cc1C)/C(=C(/Nc1ccc(C(=O)NCC3(N(C)C)CCOCC3)cc1)c1ccccc1)C(=O)N2]

$R^t$ 1.59 min (Method 1); m/z 569 (M + H)$^+$ (ES$^+$); $^1$H NMR δ: 1.64-1.90 (4H, overlapping m), 2.13 (3H, s), 2.62-2.86 (6H, overlapping m), 3.53-3.67 (2H, overlapping m), 3.76-3.89 (5H, overlapping m), 5.60 (1H, s), 6.91 (2H, m), 7.36 (1H, s), 7.54 (2H, m), 7.59-7.71 (5H, overlapping m), 8.43 (1H, m), 10.90 (1H, m), 12.25 (1H, s). (Missing 2H-presumed obscured by solvent).

TABLE 2-continued

Additional Compound Examples of the Invention

Example No., Structure, Name, Route code, LC-MS Analysis and $^1$H NMR Spectral Data (Z)-Methyl 3-(((4-(((4-(dimethylamino)tetrahydro-2H-pyran-4-yl)methyl)carbamoyl)phenyl)amino)(phenyl)methylene)-5-methyl-2-oxoindoline-6-carboxylate
Route code*: 1B
Example 37:

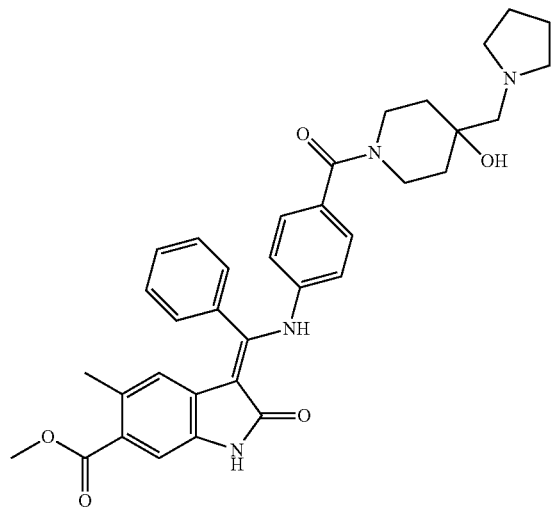 [SMILES: COC(=O)c1cc2c(cc1C)/C(=C(/Nc1ccc(C(=O)N3CCC(O)(CN4CCCC4)CC3)cc1)c1ccccc1)C(=O)N2]

$R^t$ 1.54 min (Method 1); m/z 595 (M + H)$^+$ (ES$^+$); $^1$H NMR δ: 1.14-1.69 (4H, overlapping m), 1.75-1.91 (4H, overlapping m), 2.13 (3H, s), 2.84-3.20 (8H, overlapping m), 3.75 (3H, s), 4.11 (1H, br s), 5.60 (1H, s), 6.89 (2H, m), 7.18 (2H, m), 7.37 (1H, s), 7.53 (2H, m), 7.56-7.68 (3H, overlapping m), 8.13 (1H, s), 10.86 (1H, s), 12.21 (1H, s).
(Missing 2H-assumed obscured by solvent).

(Z)-Methyl-3-(((4-(4-hydroxy-4-(pyrrolidin-1-ylmethyl)piperidine-1-carbonyl)phenyl)amino)(phenyl)methylene)-5-methyl-2-oxoindoline-6-carboxylate, formate
Route code*: 1B
Example 38:

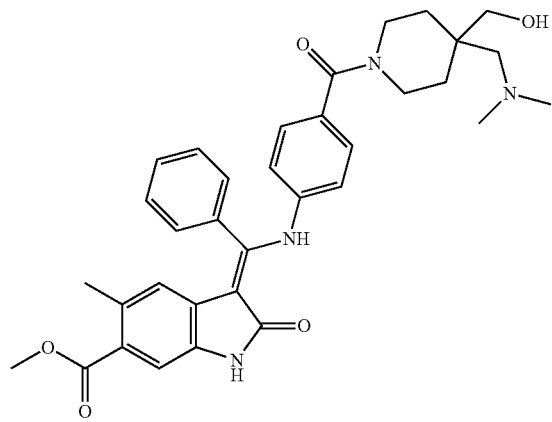

$R^t$ 1.52 min (Method 1); m/z 583 (M + H)$^+$ (ES$^+$); $^1$H NMR δ: 1.36-1.60 (4H overlapping m), 2.13 (3H, s), 2.82 (6H, s), 3.12 (2H, s), 3.19-3.38 (4H, overlapping m), 3.56 (2H, s), 3.75 (3H, s), 5.44 (1H, br s), 5.60 (1H, s), 6.89 (2H, m), 7.19 (2H, m), 7.37 (1H, s), 7.53 (2H, m), 7.57-7.73 (3H, overlapping m), 10.85 (1H, s), 12.21 (1H, s).

(Z)-Methyl-3-(((4-(4-((dimethylamino)methyl)-4-(hydroxymethyl)piperidine-1-carbonyl)phenyl)amino)(phenyl)methylene)-5-methyl-2-oxoindoline-6-carboxylate
Route code*: 1B
Example 39:

TABLE 2-continued

Additional Compound Examples of the Invention

Example No., Structure, Name, Route code, LC-MS Analysis and ¹H NMR Spectral Data

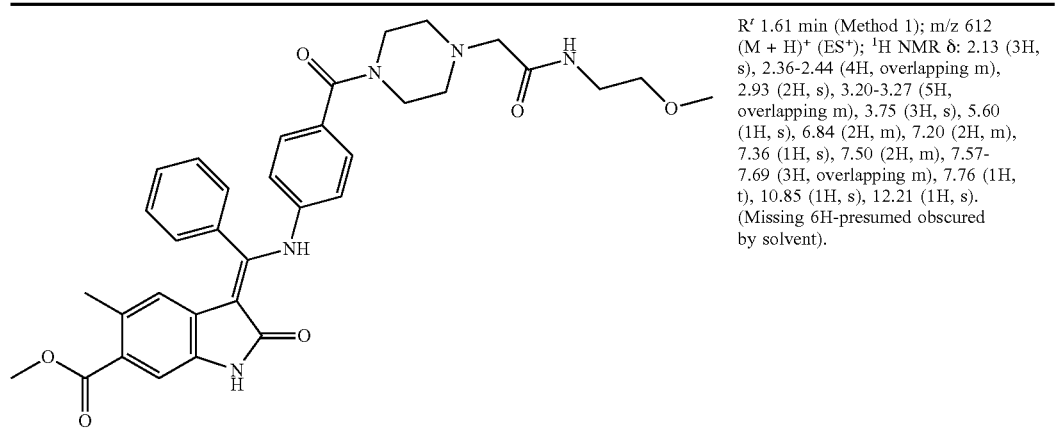

(Z)-Methyl-3-(((4-(4-(2-((2-methoxyethyl)amino)-2-oxoethyl)piperazine-1-carbonyl)phenyl)amino)(phenyl)methylene)-5-methyl-2-oxoindoline-6-carboxylate
Route code*: 1B
Example 40:

$R^t$ 1.61 min (Method 1); m/z 612 (M + H)⁺ (ES⁺); ¹H NMR δ: 2.13 (3H, s), 2.36-2.44 (4H, overlapping m), 2.93 (2H, s), 3.20-3.27 (5H, overlapping m), 3.75 (3H, s), 5.60 (1H, s), 6.84 (2H, m), 7.20 (2H, m), 7.36 (1H, s), 7.50 (2H, m), 7.57-7.69 (3H, overlapping m), 7.76 (1H, t), 10.85 (1H, s), 12.21 (1H, s). (Missing 6H-presumed obscured by solvent).

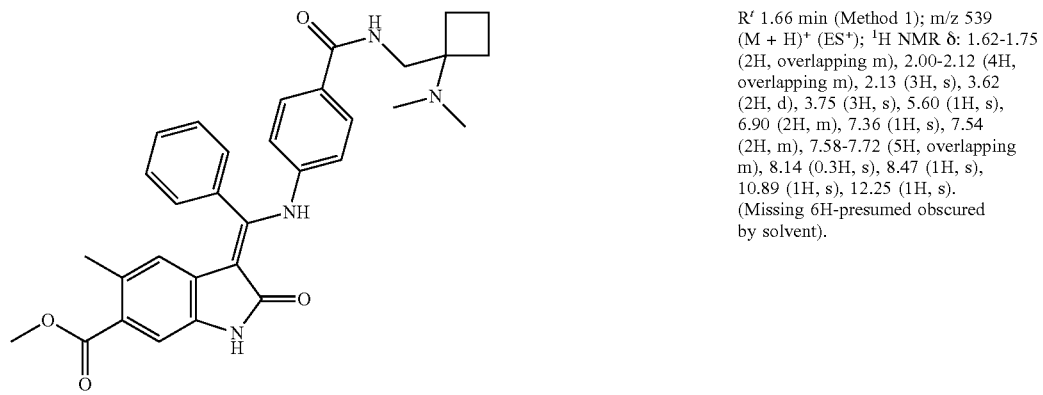

(Z)-Methyl 3-(((4-(((1-(dimethylamino)cyclobutyl)methyl)carbamoyl)phenyl)amino)(phenyl)methylene)-5-methyl-2-oxoindoline-6-carboxylate, 0.3 formate
Route code*: 1B
Example 41:

$R^t$ 1.66 min (Method 1); m/z 539 (M + H)⁺ (ES⁺); ¹H NMR δ: 1.62-1.75 (2H, overlapping m), 2.00-2.12 (4H, overlapping m), 2.13 (3H, s), 3.62 (2H, d), 3.75 (3H, s), 5.60 (1H, s), 6.90 (2H, m), 7.36 (1H, s), 7.54 (2H, m), 7.58-7.72 (5H, overlapping m), 8.14 (0.3H, s), 8.47 (1H, s), 10.89 (1H, s), 12.25 (1H, s). (Missing 6H-presumed obscured by solvent).

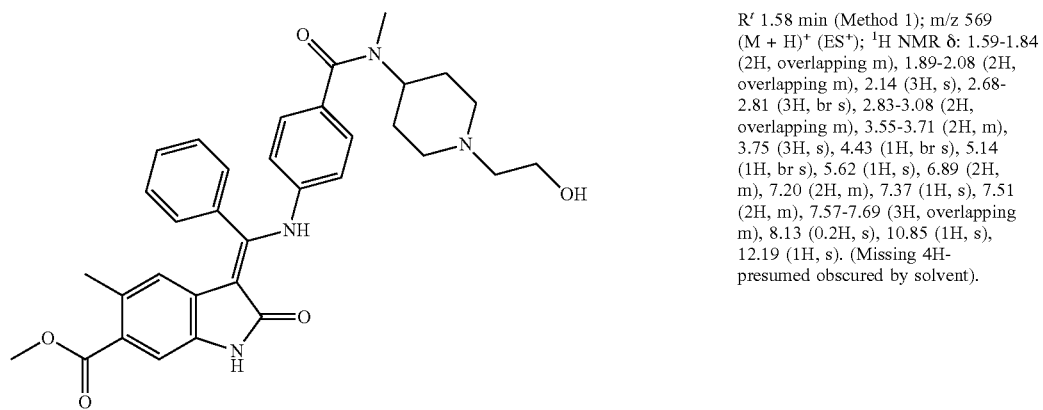

$R^t$ 1.58 min (Method 1); m/z 569 (M + H)⁺ (ES⁺); ¹H NMR δ: 1.59-1.84 (2H, overlapping m), 1.89-2.08 (2H, overlapping m), 2.14 (3H, s), 2.68-2.81 (3H, br s), 2.83-3.08 (2H, overlapping m), 3.55-3.71 (2H, m), 3.75 (3H, s), 4.43 (1H, br s), 5.14 (1H, br s), 5.62 (1H, s), 6.89 (2H, m), 7.20 (2H, m), 7.37 (1H, s), 7.51 (2H, m), 7.57-7.69 (3H, overlapping m), 8.13 (0.2H, s), 10.85 (1H, s), 12.19 (1H, s). (Missing 4H-presumed obscured by solvent).

(Z)-Methyl 3-(((4-((1-(2-hydroxyethyl)piperidin-4-yl)(methyl)carbamoyl)phenyl)amino)(phenyl)methylene)-5-methyl-2-oxoindoline-6-carboxylate, 0.2 formate Route code*: 1B Example 42:

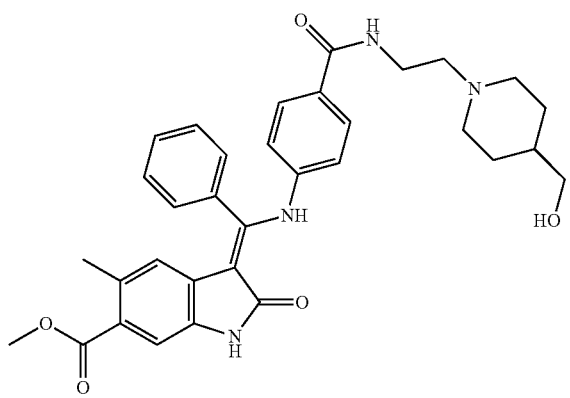 [SMILES: COC(=O)c1cc2c(cc1C)/C(=C(/Nc1ccc(C(=O)NCCN3CCC(CO)CC3)cc1)c1ccccc1)C(=O)N2]

$R^t$ 1.59 min (Method 1); m/z 569 (M + H)$^+$ (ES$^+$); $^1$H NMR δ: 1.22-1.38 (2H, overlapping m), 1.53 (1H, m), 1.74-1.78 (2H, overlapping m), 2.14 (3H, s), 2.57-2.82 (2H, overlapping m), 2.88-3.06 (2H, overlapping m), 3.26 (2H, t), 3.49 (2H, m), 3.75 (3H, s), 4.58 (1H, t), 5.62 (1H s), 6.90 (2H, m), 7.36 (1H, s), 7.52 (2H m), 7.57-7.69 (5H, overlapping m), 8.13 (0.2H, s), 8.47 (1H, t), 10.89 (1H, s), 12.23 (1H, s). (Missing 2H-presumed obscured by solvent).

(Z)-Methyl 3-(((4-((2-(4-(hydroxymethyl)piperidin-1-yl)ethyl)carbamoyl)phenyl)amino)(phenyl)methylene)-5-methyl-2-oxoindoline-6-carboxylate, 0.2 formate Route code*: 1B Example 43:

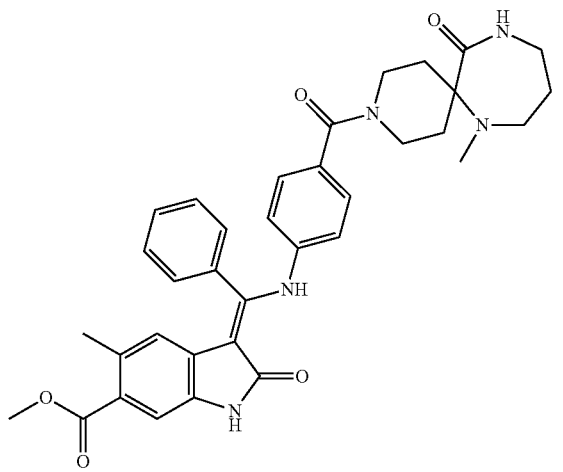 [SMILES: COC(=O)c1cc2c(cc1C)/C(=C(/Nc1ccc(C(=O)N3CCC4(CC3)C(=O)NCCCN4C)cc1)c1ccccc1)C(=O)N2]

$R^t$ 1.58 min (Method 1); m/z 608 (M + H)$^+$ (ES$^+$); $^1$H NMR δ: 1.46-1.66 (2H, overlapping m), 1.67-1.81 (2H, overlapping m), 2.13 (3H, s), 2.24 (3H, s), 2.96-3.18 (4H, overlapping m), 3.19-3.29 (3H, overlapping m), 3.75 (3H, s), 3.86 (1H, br s), 5.59 (1H, s), 6.87 (2H, m), 7.19 (2H, m), 7.36 (1H, s), 7.47-7.57 (3H, overlapping m), 7.57-7.72 (3H, overlapping m), 10.86 (1H, s), 12.22 (1H, s). (Missing 2H-presumed obscured by solvent).

(Z)-Methyl-5-methyl-3-(((4-(7-methyl-12-oxo-3,7,11-triazaspiro[5.6]dodecane-3-carbonyl)phenyl)amino)(phenyl)methylene)-2-oxoindoline-6-carboxylate Route code*: 1B Example 44:

TABLE 2-continued

Additional Compound Examples of the Invention

Example No., Structure, Name, Route code, LC-MS Analysis and ¹H NMR Spectral Data

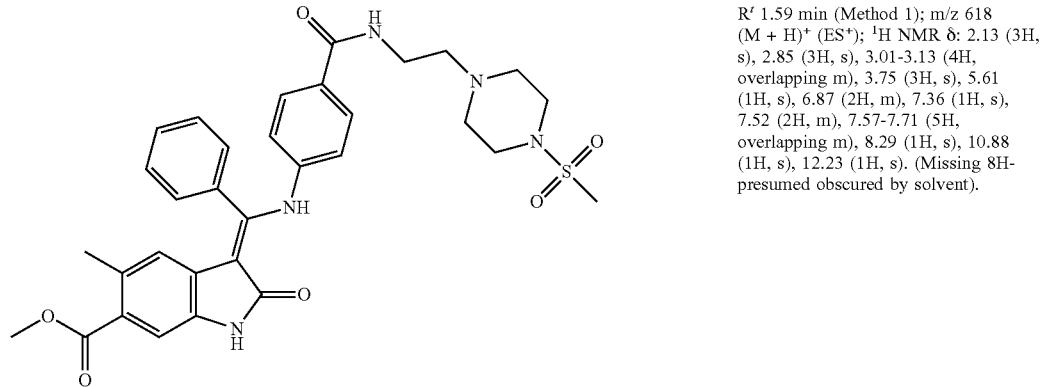

$R^t$ 1.59 min (Method 1); m/z 618 (M + H)⁺ (ES⁺); ¹H NMR δ: 2.13 (3H, s), 2.85 (3H, s), 3.01-3.13 (4H, overlapping m), 3.75 (3H, s), 5.61 (1H, s), 6.87 (2H, m), 7.36 (1H, s), 7.52 (2H, m), 7.57-7.71 (5H, overlapping m), 8.29 (1H, s), 10.88 (1H, s), 12.23 (1H, s). (Missing 8H-presumed obscured by solvent).

(Z)-Methyl-5-methyl-3-(((4-((2-(4-(methylsulfonyl)piperazin-1-yl)ethyl)carbamoyl)phenyl)amino)(phenyl)methylene)-2-oxoindoline-6-carboxylate Route code*: 1B Example 45:

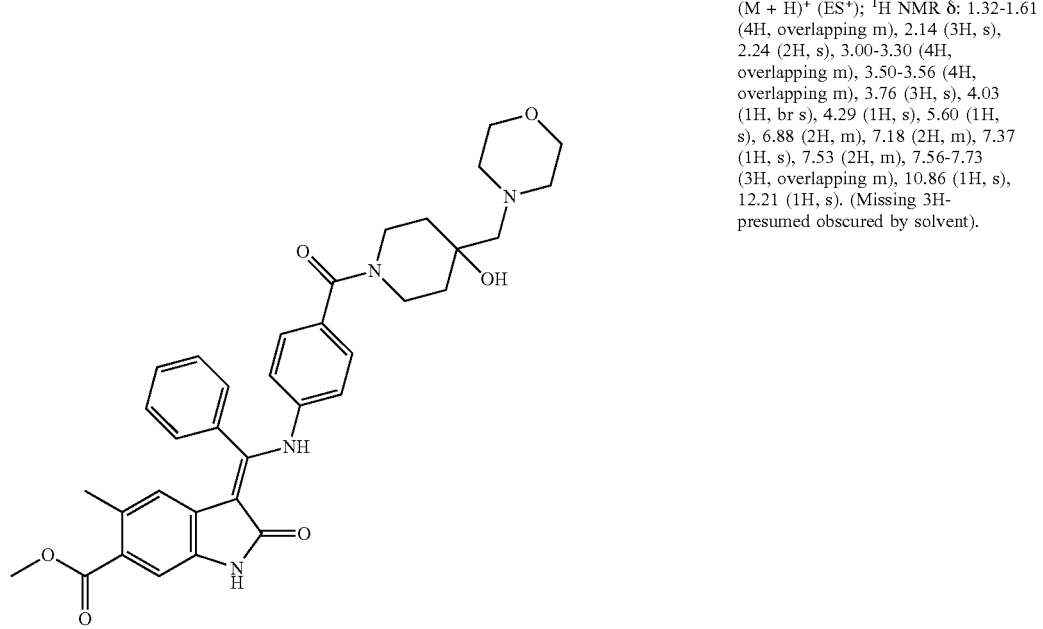

$R^t$ 1.53 min (Method 1); m/z 611 (M + H)⁺ (ES⁺); ¹H NMR δ: 1.32-1.61 (4H, overlapping m), 2.14 (3H, s), 2.24 (2H, s), 3.00-3.30 (4H, overlapping m), 3.50-3.56 (4H, overlapping m), 3.76 (3H, s), 4.03 (1H, br s), 4.29 (1H, s), 5.60 (1H, s), 6.88 (2H, m), 7.18 (2H, m), 7.37 (1H, s), 7.53 (2H, m), 7.56-7.73 (3H, overlapping m), 10.86 (1H, s), 12.21 (1H, s). (Missing 3H-presumed obscured by solvent).

(Z)-Methyl-3-(((4-(4-hydroxy-4-(morpholinomethyl)piperidine-1-carbonyl)phenyl)amino)(phenyl)methylene)-5-methyl-2-oxoindoline-6-carboxylate Route code*: 1B Example 46:

TABLE 2-continued

Additional Compound Examples of the Invention

Example No., Structure, Name, Route code, LC-MS Analysis and $^1$H NMR Spectral Data

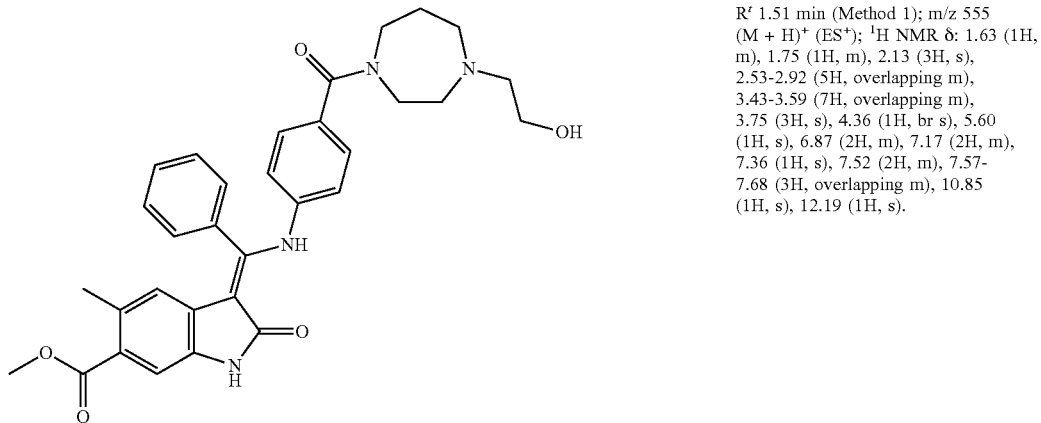

(Z)-Methyl-3-(((4-(4-(2-hydroxyethyl)-1,4-diazepane-1-carbonyl)phenyl)amino)(phenyl)methylene)-5-methyl-2-oxoindoline-6-carboxylate
Route code*: 1B
Example 47:

$R^t$ 1.51 min (Method 1); m/z 555 (M + H)$^+$ (ES$^+$); $^1$H NMR δ: 1.63 (1H, m), 1.75 (1H, m), 2.13 (3H, s), 2.53-2.92 (5H, overlapping m), 3.43-3.59 (7H, overlapping m), 3.75 (3H, s), 4.36 (1H, br s), 5.60 (1H, s), 6.87 (2H, m), 7.17 (2H, m), 7.36 (1H, s), 7.52 (2H, m), 7.57-7.68 (3H, overlapping m), 10.85 (1H, s), 12.19 (1H, s).

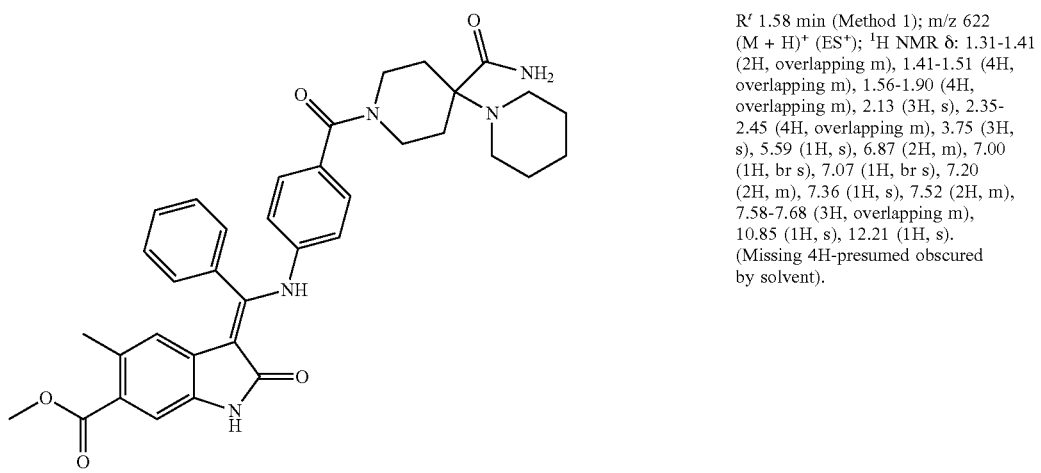

(Z)-Methyl 3-(((4-(4'-carbamoyl-[1,4'-bipiperidine]-1'-carbonyl)phenyl)amino)(phenyl)methylene)-5-methyl-2-oxoindoline-6-carboxylate
Route code*: 1B
Example 48:

$R^t$ 1.58 min (Method 1); m/z 622 (M + H)$^+$ (ES$^+$); $^1$H NMR δ: 1.31-1.41 (2H, overlapping m), 1.41-1.51 (4H, overlapping m), 1.56-1.90 (4H, overlapping m), 2.13 (3H, s), 2.35-2.45 (4H, overlapping m), 3.75 (3H, s), 5.59 (1H, s), 6.87 (2H, m), 7.00 (1H, br s), 7.07 (1H, br s), 7.20 (2H, m), 7.36 (1H, s), 7.52 (2H, m), 7.58-7.68 (3H, overlapping m), 10.85 (1H, s), 12.21 (1H, s). (Missing 4H-presumed obscured by solvent).

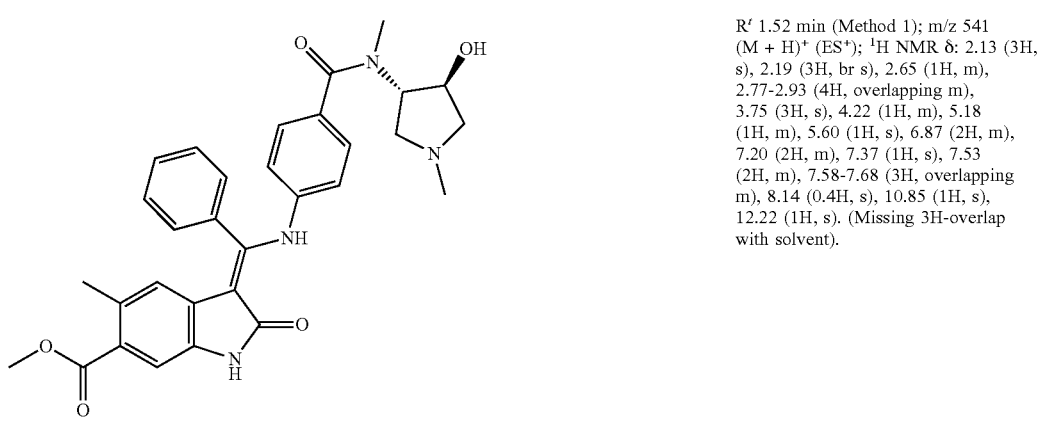

$R^t$ 1.52 min (Method 1); m/z 541 (M + H)$^+$ (ES$^+$); $^1$H NMR δ: 2.13 (3H, s), 2.19 (3H, br s), 2.65 (1H, m), 2.77-2.93 (4H, overlapping m), 3.75 (3H, s), 4.22 (1H, m), 5.18 (1H, m), 5.60 (1H, s), 6.87 (2H, m), 7.20 (2H, m), 7.37 (1H, s), 7.53 (2H, m), 7.58-7.68 (3H, overlapping m), 8.14 (0.4H, s), 10.85 (1H, s), 12.22 (1H, s). (Missing 3H-overlap with solvent).

TABLE 2-continued

Additional Compound Examples of the Invention

Example No., Structure, Name, Route code, LC-MS Analysis and ¹H NMR Spectral Data (Z)-Methyl 3-(((4-(((3S,4S)-4-hydroxy-1-methylpyrrolidin-3-yl)(methyl)carbamoyl)phenyl)amino)(phenyl)methylene)-5-methyl-2-oxoindoline-6-carboxylate, 0.4 formate Route code*: 1B Example 49:

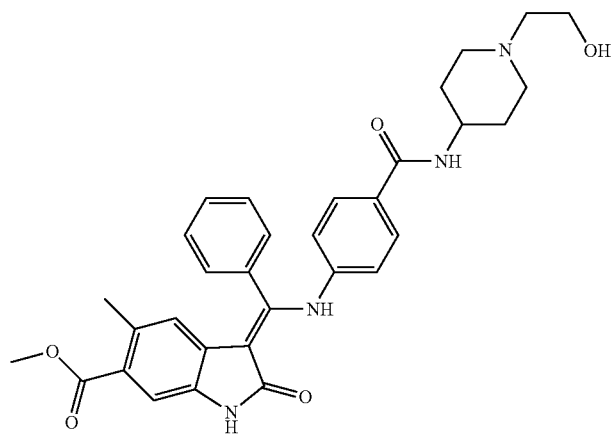 [SMILES: COC(=O)c1cc2c(cc1C)/C(=C(/Nc1ccc(C(=O)NC3CCN(CCO)CC3)cc1)c1ccccc1)C(=O)N2]

$R^t$ 1.60 min (Method 1); m/z 555 (M + H)⁺ (ES⁺); ¹H NMR δ: 1.44-1.57 (2H, overlapping m), 1.65-1.74 (2H, overlapping m), 1.91-2.10 (2H, overlapping m), 2.13 (3H, s), 2.32-2.43 (2H, overlapping m), 2.79-2.93 (2H, overlapping m), 3.44-3.51 (2H, overlapping m), 3.68 (1H, m), 3.75 (3H, s), 4.38 (1H, s), 5.61 (1H, s), 6.85 (2H, m), 7.36 (1H, s), 7.51 (2H, m), 7.56-7.70 (5H, overlapping m), 8.10 (1H, d), 10.89 (1H, s), 12.23 (1H, s).

(Z)-Methyl 3-(((4-((1-(2-hydroxyethyl)piperidin-4-yl)carbamoyl)phenyl)amino)(phenyl)methylene)-5-methyl-2-oxoindoline-6-carboxylate Route code*: 1B Example 50:

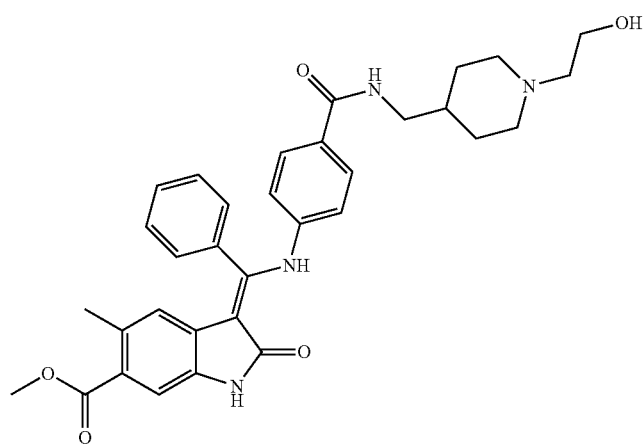 [SMILES: COC(=O)c1cc2c(cc1C)/C(=C(/Nc1ccc(C(=O)NCC3CCN(CCO)CC3)cc1)c1ccccc1)C(=O)N2]

$R^t$ 1.54 min (Method 1); m/z 569 (M + H)⁺ (ES⁺); ¹H NMR δ: 1.05-1.19 (2H, m), 1.46(1H m), 1.54-1.63 (2H, overlapping m), 1.81-1.94 (2H, overlapping m), 2.13 (3H, s), 2.28-2.40 (2H, overlapping m), 2.77-2.90 (2H, overlapping m), 3.07 (2H, t), 3.41-3.50 (2H, overlapping m), 3.75 (3H, s), 4.34 (1H, br s), 5.61 (1H, s), 6.86 (2H, m), 7.36 (1H, s), 7.52 (2H, m), 7.57-7.70 (5H, overlapping m), 8.32 (1H, t), 10.88 (1H, s), 12.23 (1H, s).

(Z)-Methyl 3-(((4-(((1-(2-hydroxyethyl)piperidin-4-yl)methyl)carbamoyl)phenyl)amino)(phenyl)methylene)-5-methyl-2-oxoindoline-6-carboxylate Route code*: 1B Example 51:

TABLE 2-continued

Additional Compound Examples of the Invention

Example No., Structure, Name, Route code, LC-MS Analysis and $^1$H NMR Spectral Data

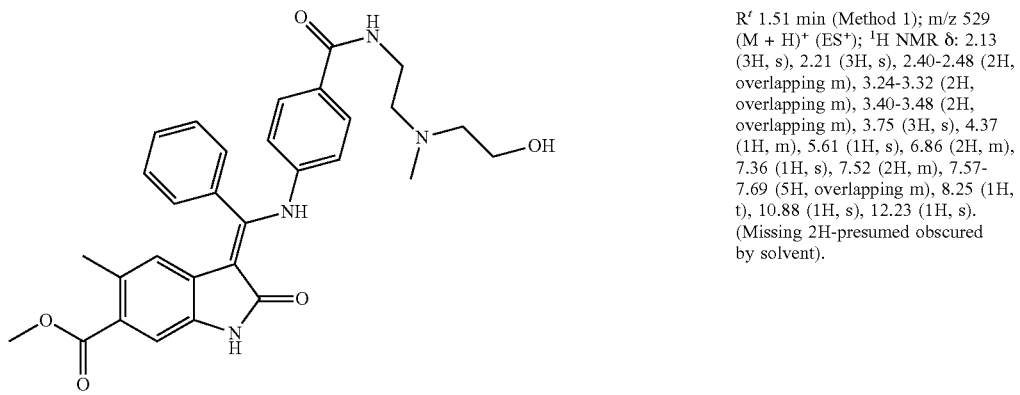

(Z)-Methyl 3-(((4-((2-((2-hydroxyethyl)(methyl)amino)ethyl)carbamoyl)phenyl)amino)(phenyl)methylene)-5-methyl-2-oxoindoline-6-carboxylate
Route code*: 1B
Example 52:

$R^t$ 1.51 min (Method 1); m/z 529 (M + H)$^+$ (ES$^+$); $^1$H NMR δ: 2.13 (3H, s), 2.21 (3H, s), 2.40-2.48 (2H, overlapping m), 3.24-3.32 (2H, overlapping m), 3.40-3.48 (2H, overlapping m), 3.75 (3H, s), 4.37 (1H, m), 5.61 (1H, s), 6.86 (2H, m), 7.36 (1H, s), 7.52 (2H, m), 7.57-7.69 (5H, overlapping m), 8.25 (1H, t), 10.88 (1H, s), 12.23 (1H, s). (Missing 2H-presumed obscured by solvent).

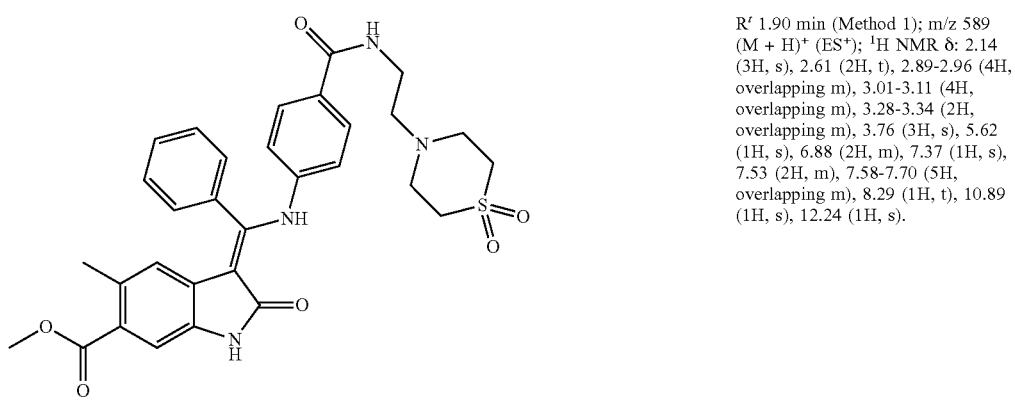

(Z)-Methyl 3-(((4-((2-(1,1-dioxidothiomorpholino)ethyl)carbamoyl)phenyl)amino)(phenyl)methylene)-5-methyl-2-oxoindoline-6-carboxylate
Route code*: 1B
Example 53:

$R^t$ 1.90 min (Method 1); m/z 589 (M + H)$^+$ (ES$^+$); $^1$H NMR δ: 2.14 (3H, s), 2.61 (2H, t), 2.89-2.96 (4H, overlapping m), 3.01-3.11 (4H, overlapping m), 3.28-3.34 (2H, overlapping m), 3.76 (3H, s), 5.62 (1H, s), 6.88 (2H, m), 7.37 (1H, s), 7.53 (2H, m), 7.58-7.70 (5H, overlapping m), 8.29 (1H, t), 10.89 (1H, s), 12.24 (1H, s).

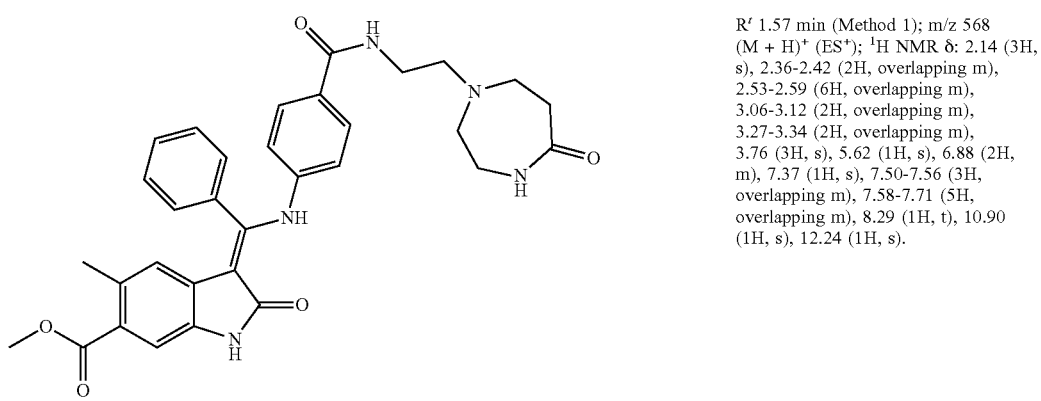

$R^t$ 1.57 min (Method 1); m/z 568 (M + H)$^+$ (ES$^+$); $^1$H NMR δ: 2.14 (3H, s), 2.36-2.42 (2H, overlapping m), 2.53-2.59 (6H, overlapping m), 3.06-3.12 (2H, overlapping m), 3.27-3.34 (2H, overlapping m), 3.76 (3H, s), 5.62 (1H, s), 6.88 (2H, m), 7.37 (1H, s), 7.50-7.56 (3H, overlapping m), 7.58-7.71 (5H, overlapping m), 8.29 (1H, t), 10.90 (1H, s), 12.24 (1H, s).

(Z)-Methyl 5-methyl-2-oxo-3-(((4-((2-(5-oxo-1,4-diazepan-1-yl)ethyl)carbamoyl)phenyl)amino)(phenyl)methylene)indoline-6-carboxylate Route code*: 1B Example 54:

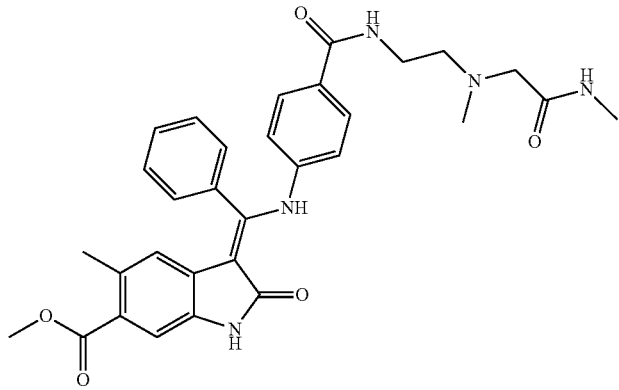

R$^t$ 1.61 min (Method 1); m/z 556 (M + H)$^+$ (ES$^+$); $^1$H NMR δ: 2.13 (3H, s), 2.21 (3H, s), 2.92 (2H, s), 3.30 (2H, m), 3.75 (3H, s), 5.61 (1H, s), 6.87 (2H, m), 7.36 (1H, s), 7.52 (2H, m), 7.56-7.71 (6H, overlapping m), 8.35 (1H, t), 10.88 (1H, s), 12.22 (1H, s). (Missing 5H-presumed obscured by solvent).

(Z)-Methyl 5-methyl-3-(((4-((2-(methyl(2-(methylamino)-2-oxoethyl)amino)ethyl)carbamoyl)phenyl)amino)(phenyl)methylene)-2-oxoindoline-6-carboxylate Route code*: 1B Example 55:

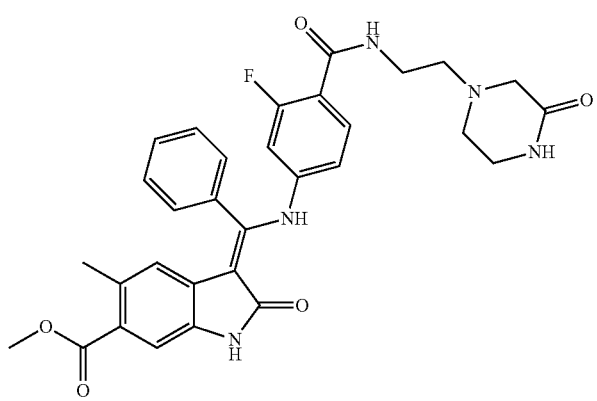 [SMILES: COC(=O)c1cc2c(cc1C)/C(=C(/Nc1ccc(C(=O)NCCN3CCNC(=O)C3)c(F)c1)c1ccccc1)C(=O)N2]

R$^t$ 1.64 min (Method 1); m/z 572 (M + H)$^+$ (ES$^+$); $^1$H NMR δ: 2.13 (3H, s), 2.54-2.60 (2H, overlapping m), 2.95 (2H, br s), 3.06-3.15 (2H, overlapping m), 3.76 (3H, s), 5.64 (1H, s), 6.58 (1H, dd), 6.77 (1H, dd), 7.36 (1H, s), 7.45 (1H, t), 7.55 (2H, m), 7.59-7.76 (4H, overlapping m), 8.07 (1H, s), 10.91 (1H, s), 12.16 (1H, s). (Missing 4H-presumed obscured by solvent).

(Z)-Methyl 3-(((3-fluoro-4-((2-(3-oxopiperazin-1-yl)ethyl)carbamoyl)phenyl)amino)(phenyl)methylene)-5-methyl-2-oxoindoline-6-carboxylate Route code*: 1B Example 56:

TABLE 2-continued

Additional Compound Examples of the Invention

Example No., Structure, Name, Route code, LC-MS Analysis and ¹H NMR Spectral Data

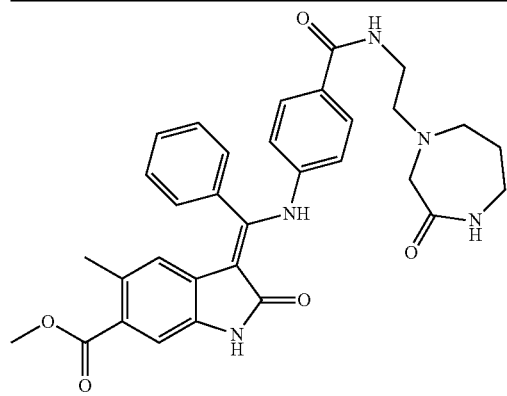

$R^t$ 1.55 min (Method 1); m/z 568 (M + H)⁺ (ES⁺); ¹H NMR δ: 2.13 (3H, s), 2.35-2.41 (2H, overlapping m), 3.03-3.11 (2H, overlapping m), 3.17 (2H, d), 3.26-3.33 (2H, overlapping m), 3.75 (3H, s), 5.61 (1H, s), 6.87 (2H, m), 7.36 (1H s), 7.47-7.56 (3H, overlapping m), 7.55-7.70 (5H, overlapping m), 8.27 (1H, t), 10.88 (1H, s), 12.23 (1H, s). (Missing 4H-presumed obscured by solvent).

(Z)-Methyl 5-methyl-2-oxo-3-(((4-((2-(3-oxo-1,4-diazepan-1-yl)ethyl)carbamoyl)phenyl)amino)(phenyl)methylene)indoline-6-carboxylate
Route code*: 1B

*Route code index:
Route 1A: see Example 1
Route 1B: see Examples 2 to 14
Route 1C: see Example 15

An additional synthesis method for Example 18:

Example 18: (Z)-Methyl-5-methyl-3-(((4-((1-methylpiperidin-4-yl)carbamoyl)phenyl)amino) (phenyl)methylene)-2-oxoindoline-6-carboxylate

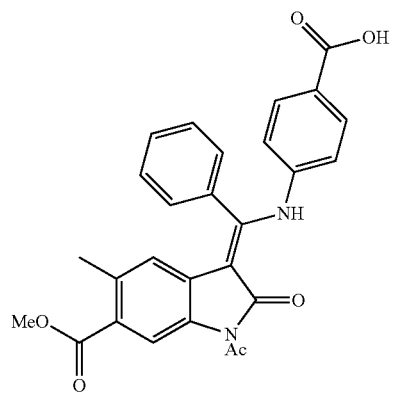

Z)-4-(((1-acetyl-6-(methoxycarbonyl)-5-methyl-2-oxoindolin-3-ylidene) (phenyl)methyl)amino)benzoic acid (Intermediate E) (10 g, 17.54 mmol) and HATU (10.01 g, 26.3 mmol) were stirred at RT for 10 mins in DMF (200 mL) then Hünig's Base (18.38 ml, 105 mmol) and 1-methylpiperidin-4-amine (2.204 g, 19.30 mmol) in DMF (10 mL) were added. The mixture was stirred at RT for 3 hours. Piperidine (17.37 ml, 175 mmol) was then added and the resulting mixture was stirred at RT for 3 h. The reaction mixture was partitioned between 10% MeOH in DCM (750 mL) and saturated sodium hydrogencarbonate solution (500 mL). The organic layer was washed with brine (300 mL) and the solvent was concentrated. The resulting solid was triturated with CH₃CN, filtered and dried to give 7 g of crude product. The reaction was repeated on the identical scale and the crude products combined and dissolved in 10% MeOH (1% Ammonia) in DCM and loaded onto a silica column (300 g). The product was eluted with 30% MeOH (1% NH₃) in DCM solution and the product containing fractions collected and the solvent then evaporated. The material was re-dissolved in 30% MeOH (1% NH₃) in DCM solution (500 mL) and washed with water (200 mL). The organic layer was dried over MgSO$_4$, filtered and the solvent was evaporated. The material was dried under reduced pressure, at 40° C., overnight, to give (Z)-methyl 5-methyl-3-(((4-((1-methylpiperidin-4-yl)carbamoyl)phenyl)amino)(phenyl)methylene)-2-oxoindoline-6-carboxylate 1478-45-2 (12.8 g, 23.91 mmol, 68.1% yield).

The product was analysed by LCMS (Agilent, X-Select, Waters X-Select C18, 2.5 μm, 4.6×30 mm, Acidic (0.1% Formic acid) 4 min method, 5-95% MeCN/water): 1478-45-2-Fin, m/z 525 (M+H)$^+$ (ES$^+$); at 1.57 min, 98% purity @254 nm. $^1$H NMR δ: R$^t$ 1.57 min (Method 1); m/z 525 (M+H)$^+$ (ES$^+$); $^1$H NMR δ: 1.44-1.57 (2H, overlapping m), 1.65-1.72 (2H, overlapping m), 1.85-1.93 (2H, overlapping m), 2.13 (6H, s), 2.70-2.76 (2H, overlapping m), 3.64 (1H, m), 3.75 (3H, s), 5.61 (1H, s), 6.86 (2H, m), 7.36 (1H, s), 7.52 (2H, m), 7.57-7.68 (5H, overlapping m), 8.09 (1H, d), 10.88 (1H, s), 12.23 (1H, s).

Biological Testing: Experimental Methods
Enzyme Inhibition Assays

The enzyme inhibitory activities of compounds disclosed herein were determined using the ADP-Glo™ assay (Promega, UK). Assays for FGFR1, PDGFRα, PDGFRβ and VEGFR2 were performed in buffer containing 40 mM Tris pH 7.5, 20 mM MgCl$_2$, 0.1 mg/mL BSA and 1 mM DTT; whilst assays for FGFR3 and VEGFR1 were performed in the above buffer supplemented with 2 mM MnCl$_2$.

FGFR1 Enzyme Inhibition

The inhibitory activities of compounds of the invention against FGFR1 (FGFR1 Kinase Enzyme System: Promega), were evaluated by mixing the FGFR1 protein (3.12 ng/mL, 2 μL), substrate (Poly (4:1 Glu$_4$, Tyr$_1$), 100 ng/mL, 2 μL) with the test compound (2 μL at either 3 μM, 0.67 μM, 0.15 μM, 0.033 μM, 0.0073 μM, 0.0016 μM, 0.0036 μM or 0.00008 μM) for 90 min at 25° C. The kinase reaction was then initiated by adding ATP (50 μM, 2 μL) and the mixture was incubated for 1 hr at 25° C. ADP-Glo™ reagent was added for 40 min (8 μL) then development reagent (16 μL) was added for 40 min prior to detection in a microplate reader (EnVision® Multilabel Reader, Perkin Elmer).

FGFR3 Enzyme Inhibition

The inhibitory activities of compounds of the invention against FGFR3 (FGFR3 Kinase Enzyme System: Promega), were evaluated by mixing the FGFR3 protein (12.5 ng/mL, 2 μL), substrate (Poly (Ala$_6$, Glu$_2$, Lys$_5$, Tyr$_1$), 100 ng/mL, 2 μL) with the test compound (2 μL at either 3 μM, 0.67 μM, 0.15 μM, 0.033 μM, 0.0073 μM, 0.0016 μM, 0.0036 μM or 0.00008 μM) for 90 min at 25° C. The kinase reaction was initiated by adding ATP (50 μM, 2 μL) and the mixture was incubated for 90 min at 25° C. ADP-Glo™ reagent was added for 40 min (8 μL) then development reagent (16 μL) was added for 40 min prior to detection in a microplate reader (EnVision® Multilabel Reader, Perkin Elmer).

PDGFRα Enzyme Inhibition

The inhibitory activities of compounds of the invention against PDGFRα (PDGFRα Kinase Enzyme System: Promega), were evaluated by mixing the PDGFRα protein (12.5 ng/mL, 2 μL), substrate (Poly (4:1 Glu$_4$, Tyr$_1$), 100 ng/mL, 2 μL) with the test compound (2 μL at either 3 μM, 0.67 μM, 0.15 μM, 0.033 μM, 0.0073 μM, 0.0016 μM, 0.0036 μM or 0.00008 μM) for 90 min at 25° C. The kinase reaction was initiated by adding ATP (25 μM, 2 μL) and the mixture was incubated for 1 hr at 25° C. ADP-Glo™ reagent was added for 40 min (8 μL) then development reagent (16 μL) was added for 40 min prior to detection in a microplate reader (EnVision® Multilabel Reader, Perkin Elmer).

PDGFRβ Enzyme Inhibition

The inhibitory activities of compounds of the invention against PDGFRβ (PDGFRβ Kinase Enzyme System: Promega), were evaluated by mixing the PDGFRβ protein (6.25 ng/mL, 2 μL), substrate (Poly (4:1 Glu$_4$, Tyr$_1$), 100 ng/mL, 2 μL) with the test compound (2 μL at either 3 μM, 0.67 μM, 0.15 μM, 0.033 μM, 0.0073 μM, 0.0016 μM, 0.0036 μM or 0.00008 μM) for 90 min at 25° C. The kinase reaction was initiated by adding ATP (25 μM, 2 μL) and the mixture was incubated for 1 hr at 25° C. ADP-Glo™ reagent was added for 40 min (8 μL) then development reagent (16 μL) was added for 40 min prior to detection in a microplate reader (EnVision® Multilabel Reader, Perkin Elmer).

VEGFR1 Enzyme Inhibition

The inhibitory activities of compounds of the invention against VEGFR1 (VEGFR1 Kinase Enzyme System: Promega), were evaluated by mixing the VEGFR1 protein (12.5 ng/mL, 2 μL), substrate (IGFR1Rtide, 100 ng/mL, 2 μL) with the test compound (2 μL at either 3 μM, 0.67 μM, 0.15 μM, 0.033 μM, 0.0073 μM, 0.0016 μM, 0.0036 μM or 0.00008 μM) for 90 min at 25° C. The kinase reaction was initiated by adding ATP (50 μM, 2 μL) and the mixture was incubated for 90 min at 25° C. ADP-Glo™ reagent was added for 40 min (8 μL) then development reagent (16 μL) was added for 40 min prior to detection in a microplate reader (EnVision® Multilabel Reader, Perkin Elmer).

VEGFR2 Enzyme Inhibition

The inhibitory activities of compounds of the invention against VEGFR2 (VEGFR2 Kinase Enzyme System: Promega), were evaluated by mixing the VEGFR2 protein (1.56 ng/mL, 2 μL), substrate (Poly (4:1 Glu$_4$, Tyr$_1$), 100 ng/mL, 2 μL) with the test compound (2 μL at either 3 μM, 0.67 μM, 0.15 μM, 0.033 μM, 0.0073 μM, 0.0016 μM, 0.0036 μM or 0.00008 μM) for 90 min at 25° C. The kinase reaction was initiated by adding ATP (50 μM, 2 μL) and the mixture was incubated for 1 hr at 25° C. ADP-Glo™ reagent was added for 40 min (8 μL) then development reagent (16 μL) was added for 40 min prior to detection in a microplate reader (EnVision® Multilabel Reader, Perkin Elmer).

In all cases, the kinase converts ATP to ADP and the ADP-Glo™ reagent then depletes any remaining ATP. The detection reagent converts the ADP that has been produced back into ATP and generates luciferase which can be detected as luminescence. Therefore the luminescent signal is directly proportional to the amount of ADP produced by the enzyme reaction and a reduction in this signal after compound treatment demonstrates inhibition. The percentage inhibition produced by each concentration of compound was calculated using the equation shown below:

$$\% \text{ Inhibition} = 1 - \frac{(Mean_{Min} - Mean_{Inh})}{(Mean_{Min} - Mean_{Max})} \times 100$$

Percentage inhibition was then plotted against compound concentration, and the relative 50% inhibitory concentration (RIC50) was determined from the resultant concentration-response curve. Once this had been determined Ki was calculated using the equation below:

$$Ki = \frac{RIC50}{1 + \left(\frac{[S]}{Km}\right)}$$

Cellular and Other In Vitro Assays

PDGF-BB Induced Normal Human Lung Fibroblast (NHLF) Proliferation

NHLF's (Lonza group Ltd) are expanded up to 90% confluence in FGM-2 growth media supplemented with 2% FBS (plus SingleQuot™ growth factors; Lonza). Fibroblasts are harvested (Trypsin/EDTA), suspended at $25 \times 10^3$ per ml in growth media and 200 µl is added per well ($5 \times 10^3$ cells/well) of a 96 well tissue culture plate. After 24 hr incubation (37 C/5% 002/95% $O_2$), cells are serum starved (24 hr) by reducing the FBS concentration to 0.1% in the culture media. Cells are pre-incubated with test compound for 1 hr, then stimulated with rhuPDGF-BB (100 ng/ml, R&D Systems) for 48 hr. Cell proliferation is assessed by BrdU incorporation (Cell Proliferation colorimetric ELISA, Roche). The percent inhibition of rhuPDGF-BB-induced NHLF proliferation by test compound at each concentration is calculated as a percentage of that achieved by rhuPDGF-BB at each concentration of test compound by comparison against vehicle control (basal proliferation). The relative 50% inhibitory concentration ($RIC_{50}$) is determined from the resultant concentration-response curve.

PDGF-BB/FGF-Basic Induced MRC-5 Fetal Human Lung Fibroblast Proliferation

MRC-5 fibroblasts (LGC Standards) are expanded up to 90% confluence in DMEM media supplemented with 10% FBS. Cells are harvested (Trypsin/EDTA), suspended at $25 \times 10^3$ per ml in growth media and 200 µl is added per well ($5 \times 10^3$ cells/well) of a 96 well tissue culture plate. After 24 hr incubation (37 C/5% $CO_2$/95% $O_2$), cells are serum starved (3 hr) by replacing the growth media with media containing 0.1% FBS. Cells are then pre-incubated with test compound for 1 hr followed by stimulation with rhuPDGF-BB (100 ng/ml, R&D Systems) or rhuFGF-basic (5 ng/ml; R&D Systems) for 48 hr. Cell proliferation is assessed by BrdU incorporation (Cell Proliferation colorimetric ELISA, Roche). The percent inhibition of rhuPDGF-BB/rhuFGF-induced MRC-5 proliferation by test compound at each concentration is calculated as a percentage of that achieved by rhuPDGF-BB/FGF-basic at each concentration of test compound by comparison against vehicle control (basal proliferation). The relative 50% inhibitory concentration ($RIC_{50}$) is determined from the resultant concentration-response curve.

$VEGF_{165}$/FGF-Basic Induced Endothelial Cell Proliferation

TeloHAEC (telomerase immortalized Human Aortic Endothelial Cells; ATCC) are seeded in to 96 well tissue culture plates at a cell density of 4000 cells per well (100 µl) in endothelial cell starvation medium (0.5% FBS, without FGF and VEGF growth factors) and cultured for 3 hr (37 C/5% CO2/95% O2). Cells are pre-incubated with test compound for 1 hr followed by stimulation with rhu-$VEGF_{165}$ (10 ng/ml, R&D Systems) or rhuFGF-basic (5 ng/ml, R&D Systems) for 48 hr. Cell proliferation is assessed by BrdU incorporation (Cell Proliferation colorimetric ELISA, Roche). The percent inhibition of rhu-$VEGF_{165}$/rhuFGF-basic-induced TeloHAEC proliferation by test compound at each concentration is calculated as a percentage of that achieved by rhuVEGF$_{165}$/FGF-basic at each concentration of test compound by comparison against vehicle control (basal proliferation). The relative 50% inhibitory concentration ($RIC_{50}$) is determined from the resultant concentration-response curve.

PDGF-BB Induced Phosphorylation of PDGFRβ in Fibroblasts

MRC-5/NHLF/NIH-3T3s (mouse embryonic fibroblasts, LGC Standards) were used to evaluate the inhibitory effect of test compound on PDGFRβ phosphorylation using the HTRF (Homogeneous Time Resolved Fluorescence) phospho-PDGFRβ (Tyr751) cellular assay kit (Cisbio). MRC-5/NHLFs were seeded in to 96 well tissue culture plates at a cell density of 10000 cells per well in DMEM growth media (10% FBS) or FGM-2 growth media (2% FBS) respectively and cultured for 48 hr (37 Cl 5% $CO_2$/95% $O_2$). NIH-3T3s were seeded in to 96 well tissue culture plates ata cell density of 7000 cells per well in DMEM growth media (10% FBS) and cultured for 48 hrs (37 C/5% $CO_2$/95% $O_2$). Cell media was replaced with the respective starvation medium containing 0.1% FBS and plates further incubated for 24 hr (37 C/5% $CO_2$/95% $O_2$) for MRC-5/NHLFs and for 3 hr for NIH-3T3s. Cells were pre-incubated with test compound for 1 hr and then stimulated with rhuPDGF-BB (25-50 ng/ml, R&D Systems) for 5 min and rmPDGF-BB (25 ng/ml, Life Technologies) for NIH-3T3s. Media was aspirated off and cells immediately lysed by addition of 50 µl lysis buffer provided in the HTRF assay kit. 16 µl of cell lysate from each well was transferred to a white low volume 384 well plate to which propriety kit reagents were added as per kit instructions. Phosphorylation of the PDGFRβ was quantitated by calculating the ratio of fluorescence read at 665 nm and 620 nm. The percent inhibition of rPDGF-BB induced PDGFRβ phosphorylation by test compound was calculated as a percentage of that achieved by rPDGF-BB at each concentration of test compound by comparison against vehicle control. The relative 50% inhibitory concentration ($RIC_{50}$) was determined from the resultant concentration-response curve.

$VEGF_{165}$ Induced Phosphorylation of VEGFR2 in Endothelial Cells

TeloHAECs (telomerase immortalized Human Aortic Endothelial Cells; ATCC) were used to evaluate the inhibitory effect of test compound on VEGFR2 phosphorylation using the HTRF (Homogeneous Time Resolved Fluorescence) phospho-VEGFR2 (Tyr1175) cellular assay kit (Cisbio). TeloHAECs were seeded in to 96 well tissue culture plates at a cell density of 12000 cells per well in endothelial growth medium (ATCC; 2% FBS) and cultured for 48 hr (37 C/5% $CO_2$/95% $O_2$). Cell media was replaced with starvation medium (without VEGF and FGF growth factors) containing 0.5% FBS and plates further incubated for 24 hr (37 C/5% CO2/95% $O_2$). Cells were pre-incubated with test compound for 1 hr followed by stimulation with rhu-$VEGF_{165}$ (50 ng/ml, R&D Systems) for 5 min. Media was aspirated off and cells immediately lysed by addition of 50 µl lysis buffer provided in the HTRF assay kit. 16 µl of cell lysate from each well was transferred to a white low volume 384 well plate to which propriety kit reagents were added as per kit instructions. Phosphorylation of the VEGFR2 was quantitated by calculating the ratio of fluorescence read at 665 nm and 620 nm. The percent inhibition of rhuVEGF$_{165}$ induced VEGFR2 phosphorylation by test compound was calculated as a percentage of that achieved by rhuVEG F165 at each concentration of test compound by comparison against vehicle control. The relative 50% inhibitory concentration ($RIC_{50}$) was determined from the resultant concentration-response curve.

Fibroblast Gel Contraction Assay

NHLF's are expanded up to 90% confluence in FGM-2 growth media (Lonza) supplemented with 2% FBS (plus SingleQuot™ growth factors). Fibroblasts are harvested (Trypsin/EDTA) and suspended at $1 \times 10^6$ per ml in serum free media. Based on the cell contraction assay kit (Cell Biolabs) a cell lattice is prepared by mixing 1 part cell suspension+4 parts collagen gel solution as per kit instructions. 0.9 ml aliquots of the collagen lattice is added to 1.5 ml centrifuge tubes and treated with final assay concentrations of test compound. 250 µl of compound treated lattice is then pipetted into each well of a 48 well tissue culture plate (triplicate per test concentration). The plate is incubated for 90 min (37 C/5% $CO_2$/95% $O_2$) to allow the gels to polymerize. 250 µl of serum free media containing final assay concentrations of test compound are then added to each corresponding gel. After further 30 min incubation, the gels are stimulated with TGFβ1 (10 ng/ml; R&D Systems). Following a 24 hr (37 C/5% $CO_2$/95% $O_2$) incubation period, each individual gel is removed and weighed on a precision balance. The effect of the test compound at each concentration is expressed as the percent reversal of the TGFβ1 induced contraction relative to the vehicle treated basal contraction.

Fibroblast IL-6 Release Assay

NHLF's are expanded up to 90% confluence in FGM-2 growth media (Lonza) supplemented with 2% FBS (plus SingleQuot™ growth factors). Fibroblasts are harvested (Trypsin/EDTA), suspended at $50 \times 10^3$ per ml in growth media and 200 µl added per well ($10 \times 10^3$ cells/well) of a 96 well tissue culture plate. After 24 hr incubation (37 C/5% $CO_2$/95% $O_2$), cells are serum starved (24 hr) by reducing the media FBS concentration to 0.1%. Cells are pre-incubated with test compound for 1 hr, then stimulated with TGFβ1 (5 ng/ml, R&D Systems) for 24 hr. Cell free supernatants are recovered for determination of IL-6 concentrations by sandwich ELISA (Duo-set, R&D systems). The inhibition of IL-6 production is calculated as a percentage of that achieved by 5 ng/ml TGFβ1 at each concentration of test compound by comparison against vehicle control. The relative 50% inhibitory concentration ($RIC_{50}$) is determined from the resultant concentration-response curve.

Mast Cell Apoptosis

Mast cells are differentiated from cord blood CD34+ cells (Lonza) for 8 weeks in growth media supplemented with 100 ng/ml SCF and 10 ng/ml IL-6. Mast cells are seeded in 384 well white clear bottom plates between 2500 to 10000 cells/well in growth media containing SCF (100 ng/ml). As a positive control for apoptosis, 8 wells are incubated in growth media without SCF. Cells are incubated with test compounds or vehicle for 24 hr (37 C/5% $CO_2$/95% $O_2$). Caspase-3/7 luminogenic substrate (Caspase-Glo 3/7 Assay, Promega) is added to the cells and incubated at room temperature for 30 min, before reading the luminescence signal. The induction of apoptosis by test compounds is calculated as a percentage of that achieved by cells incubated in the absence of SCF (maximal apoptotic response) for each concentration of test compound compared to vehicle (baseline apoptosis). The relative 50% inhibitory concentration (RIC50) is determined from the resultant concentration-response curve.

The Effect of Test Compounds on Cell Viability

MRC-5 cells were seeded into white clear bottom (for fluorescence/luminescence reads) or clear (for colorimetric reads) 96 well tissue culture plates at a cell density of $12 \times 10^3$ cells per well in DMEM growth media (10% FBS). After 24 hr incubation (37 C/5% $CO_2$/95% $O_2$), the growth media was replaced with media containing 0.1% FBS plus test compound/vehicle and incubated for a further 48 hrs. For the colorimetric MTT assay (assessment of cellular metabolic activity), supernatants from each well were aspirated off, replaced with 100 µl/well fresh media (0.1% FBS) and 10 µl/well of 5 mg/ml MTT. After a 1 hr incubation (37 C/5% $CO_2$/95% $O_2$) period the media were aspirated off and 100% DMSO (100 µl) added to each well. The plates were lightly shaken for 15 minutes prior to reading the absorbance at 550 nm.

The percentage loss of cell viability (represented by a reduction in absorbance values) was calculated for each compound concentration relative to vehicle (0.5% DMSO) treated cells. The MultiTox-Fluor Multiplex Cytotoxicity assay in conjunction with the Caspase-Glo 3/7 assay (Promega) were used to measure cellular cytotoxicity/viability and apoptosis. The MultiTox-Fluor Multiplex Cytotoxicity assay is a single-reagent-addition fluorescent assay that simultaneously measures the relative number of live and dead cells in cell populations. The assay gives ratiometric, inversely correlated measures of cell viability and cytotoxicity. The ratio of viable cells to dead cells is independent of cell number and, therefore, can be used to normalize data. Addition of the single Caspase-Glo® 3/7 reagent in an "add-mix-measure" format results in cell lysis, followed by caspase cleavage of a substrate and generation of a "glow-type" luminescent signal. For this multiplex cytotoxicity assay, 100 µl of cell supernatants from the 48 hr compound treated cells were carefully removed from each well then 50 µl MultiTox reagent added (working solution of proprietary MultiTox reagents were prepared by diluting 10 µl of GF-AFC and bis AAF-R110 into 10 ml assay buffer as per kit instructions). Cells were incubated in the dark for 30 minutes before taking two separate fluorescence readings at; $400_{Ex}/505_{Em}$ (Live cell read) and $485_{Ex}/520_{Em}$ (Dead cell read). Next, 100 µl of supernatant was carefully removed from each well and 50 µl of Caspase 3/7 Glo reagent added to the cell plate and incubated for 30 minutes in the dark. Caspase 3/7 activity was quantitated by reading the luminescence signal. An increase in signal above the vehicle treated control cells represented an increase cell apoptosis.

Fibroblast-to-Myofibroblast Transition Assay

To assess anti-fibrotic activity of test compounds, two alternate protocols were used. In the first, isolated lung fibroblasts are seeded on 96-well plates at 3000 cells/well. Five (5) days post-seeding, cells are refreshed and test compounds or vehicle are added to the cells. After one (1) hour, TGF-β1 (1.25 ng/mL) is added to induce fibroblast-to-myofibroblast transition. Expression of αSMA, a marker of myofibroblast transition, is measured after 72 hours by immunostaining, assessed by high content imaging on the IN Cell Analyzer 2200 (GE Healthcare) and quantified using a proprietary (BioFocus) algorithm with the IN Cell developer software (GE Healthcare). The output of the algorithm represents the staining intensity multiplied by the stained area (DxA levels). Co-staining of cell nuclei with 4',6-diamidino-2-phenylindole (DAPI) is performed in order to quantify cell number, as a measure of potential toxicity and/or to normalize αSMA for differences in cell density.

In the alternate protocol, isolated lung fibroblasts are seeded on 96-well plates at 5100 cells/well. After 24 hours, cells are refreshed with starve media for a further 24 hours. Test compounds or vehicle are added to the cells. After one (1) hour, TGF-β1 (0.1 ng/mL) is added to induce fibroblast-to-myofibroblast transition. Expression of αSMA, a marker of myofibroblast transition, is measured after 48 hours by immunostaining, assessed by high content imaging on the ImageXpres micro (Molecular Devices) and quantified using MetaXpress software (Molecular Devices). The percent positive cells is used to evaluate αSMA staining and therefore the degree of fibroblast to myofibroblast transition. Co-staining of cell nuclei with 4',6-diamidino-2-phenylindole (DAPI) is performed in order to quantify cell number, as a measure of potential toxicity and/or to normalize αSMA for differences in cell density.

Evaluation of Duration of Action of Test Compounds Against PDGF-BB Induced Phosphorylation of PDGFRβ in Human Fetal Lung Fibroblast Cells To determine the relative persistence of the effects of drug exposure on PDGF-BB induced PDGFRβ phosphorylation, a washout experiment is used utilising MRC-5 human fetal lung fibroblast cells and a Homogenous HTRF (Homogeneous Time Resolved Fluorescence) phospho-PDGFRβ (Tyr751) cellular assay kit (Cisbio), that detects receptor modulation of the PDGF-BB induced phosphorylation of PDGFRβ.

Washout Protocol

MRC-5 cells are initially dislodged with trypsin and neutralized with full media (DMEM growth media, 10% FBS). $1.2 \times 10^6$ cells are placed into microfuge tubes, centrifuged at 10,000 rpm for 30 sec utilising a bench top centrifuge, supernatant is removed and cells are washed in 1 ml of pre-warmed (37° C.) wash buffer (HBSS pH7.4, 0.1% BSA and 0.04% Pluronic acid) to remove any residual FBS. Cells are then centrifuged again, supernatant removed and incubated with 500 μL of vehicle, test control compound and test compound (at concentration giving 70% inhibition) for 1 hr with gentle shaking at 37° C. Following incubation, cells are dispersed evenly and 100 μL aliquot is removed from each tube, for a no wash control. The remaining cells are then subjected to 5 repeated wash steps in which cells are centrifuged, supernatant removed and re-suspended in 1 ml of fresh pre-warmed (37° C.) wash buffer. To avoid effects of compound carry over due to sticking to plastic, cells are transferred to fresh tubes following each wash step and placed in a 37° C. shaker (900 rpm) for 10 minutes incubation between washing to allow for re-equilibration between cells and buffer. Following the final wash step, the cells are re-suspended in 360 ul of pre-warmed wash buffer. 5 μL from both no wash and washed tubes is placed into a 384 white polypropylene microtitre plate (Greiner) and incubated at 37° C. for 15 minutes. The cells are then stimulated with 5 μL of rhuPDGF-BB (3 ng/ml, R&D Systems) for 5 min, after which cells are immediately lysed by the addition of 10 μl of lysis buffer provided in the HTRF assay kit. The cells are placed on a plate shaker (rpm 1450) for 1 hr, after which the plate is briefly centrifuged for 30 sec (3000 rpm) and the proprietary HTRF kit reagents added as per kit instructions. Phosphorylation of the PDGFRβ is quantitated by calculating the ratio of fluorescence read at 665 nm and 620 nm. The percentage inhibition of rhuPDGF-BB induced PDGFRβ phosphorylation by test compound is calculated as a percentage of that achieved at 3 μg/ml rhuPDGF-BB against the test vehicle control.

PAMPA Permeability Assay

This assay measures permeability across an artificial membrane and was performed by Cyprotex using a parallel artificial membrane permeability assay. It is an in vitro model of passive, transcellular permeation through an artificial hexadecane membrane, (Wohnsland F et al., *Med. Chem.*, 2001 44; 923-930). The compounds can be categorised into low and high permeability. Generally, compounds which have a $P_{app} < 10 \times 10^{-6}$ cm/s are classified as low permeability and compounds with a $P_{app} > 10 \times 10^{-6}$ cm/s are classified as high permeability. Compounds which have low permeability are believed to be likely to have long residency time in the lung due to their slower absorption (Tronde Ann et al., *J Pharm. Sci.*, 2003, 92(6), 1216-33).

Protocol Summary

Test compound is added to the donor side of a filter coated artificial PAMPA membrane, and permeability is measured by monitoring the appearance of the test compound on the acceptor side of the cell membrane using LC-MS/MS.

Experimental Procedure

A solution of hexadecane in hexane was prepared (5% v/v) and an aliquot was added onto the membrane of each well in the filter (donor) plate (Multiscreen filter plate for permeability, Millipore). The donor plates were then allowed to dry to ensure evaporation of hexane. Buffer (pH 7) containing DMSO (5%) was added to each well of the acceptor plates. Test compound solutions were prepared by diluting 10 mM DMSO concentrates in buffer which gave a final test compound concentration of 10 μM (final DMSO concentration 5%). The fluorescent integrity marker lucifer yellow was also included in the test compound solution. The donor plate was inserted into the acceptor plate and the plates were then incubated at room temperature for 5 hr. Analytical standards were prepared from test compound solutions. Test compound permeability was assessed in quadruplicate. On each plate compounds of known permeability characteristics were run as controls.

At the end of the incubation period the donor plate was removed from the acceptor plate. The donor and acceptor samples for test and control compounds were quantified by LC-MS/MS cassette analysis using a 5-point calibration with appropriate dilution of the samples. The experimental recovery was calculated from both donor and acceptor compartment concentrations.

If the lucifer yellow permeation was above QC limits for one, two or three individual test compound wells, then n=3, 2 or 1 results were reported.

Data Analysis

The apparent permeability coefficient ($P_{app}$) for each compound was calculated from the following equation:

$$Papp = \left\{ C \times -\ln\left(1 - \frac{[drug]_{acceptor}}{[drug]_{equilibrium}}\right) \right\}$$

$$\text{where } C = \frac{V_D \times V_A}{(V_D + V_A) \text{Area} \times \text{time}}$$

where $V_D$ and $V_A$ are the volumes of the donor and acceptor compartments, respectively, area is surface area of the membrane multiplied by the porosity and the equilibrium drug concentration is the concentration of test compound in the total volume of the donor and acceptor compartments.

In Vivo Screening: Pharmacodynamics and Pharmacokinetics

Bleomycin-Induced Fibrosis in Mice (a Mouse Model of Lung Fibrosis)

C57BL6/J mice are dosed by the intra tracheal route with either vehicle or bleomycin sulphate (MP Biomedicals, 2 U/kg) on day 0. Compounds are administered intra-nasally (as aqueous solutions or suspensions, 25-50 ul) once daily from day 5 until day 20. After a further 24 hr the animals are anesthetized, their tracheas cannulated and animals are mechanically ventilated using a computer-controlled piston ventilator (flexiVent, SCIREQ Inc., Montreal, Canada). Following lung function measurements, mice are exsanguinated and bronchoalveolar lavage fluid (BALF) extracted. Total and differential white cell counts in the BALF samples are measured using a Neubaur haemocytometer. Cytospin smears of the BALF samples are prepared by centrifugation and stained using a DiffQuik stain system (Dade Behring).

Cells are counted using oil immersion microscopy. Leftover BALF supernatants are saved for cytokine analysis.

Whole lungs are inflated under 25 cm $H_2O$ pressure with 10% neutral buffered formalin through the tracheal cannula and immersed in formalin for at least 24 h. After being processed into paraffin blocks, the lungs are sectioned (5 µm) and stained with either hematoxylin and eosin (H&E), picro-sirius red (PSR) or Masson's trichrome. A constant number of pictures are randomly taken of 4 transversal sections. Pictures are scored from 0 (no PF) to 8 (maximal PF) by 2 blinded investigators to assess fibrotic changes in the lungs. Additionally, staining for alpha-smooth muscle actin (Thermo Scientific, Freemont, Calif.) is done using standard methodologies. Soluble collagen in whole lung homogenate is assessed by Sircol collagen assay (Biocolor Ltd, Carrickfergus, UK).

PDGFBB-Induced PDGFRβ Phosphorylation in Mice 7 to 12-week-old C57BL/6 mice (Charles River) are housed under a 12-hour light/dark cycle and receive food and water ad libitum. Aqueous solutions or suspensions of compounds are prepared to deliver indicated doses (mg/kg) based on the average weight of the mice in the groups. The animals are anesthetized and compounds or vehicles are administered intra-nasally (50 ul). After recovery at indicated time points, the animals are anesthetized again and recombinant mouse PDGF-BB (50 ug/animal, Cambridge Biosciences) or vehicle is administered intra-tracheally, and then, 5 to 30 minutes after PDGF-BB instillation, terminal blood samples are taken and whole lungs are excised. Plasma is isolated from the blood by centrifugation. Approximately one half of the left lobes are homogenised using a FastPrep-24 5G instrument in Matrix D lysing tubes (MP Biomedicals). Phosphorylation levels of PDGFRβ are measured by Western blot using anti-phospho-PDGFRα (Y849)/β(Y857), anti-total PDGFRβ/α and anti GAPDH antibodies (Cell Signaling). Phosphorylation levels of PDGFRβ are reported as ratios to Total PDGFRβ levels or to GAPDH. The percentage inhibition of PDGFRβ phosphorylation is calculated for each treatment relative to vehicle treatment. Measurements of compound levels in the plasma or lung homogenates are determined by LC-MS/MS.

Pharmacokinetic Measurements in Rodents

Male CD rats or C57BL/6J mice were used for pharmacokinetic studies where animals were dosed intra-tracheally, orally or intravenously for rats and intra-nasally, orally or intravenously for mice.

Animals were dosed intravenously via the lateral tail vein. Animals dosed via the intra-tracheal or intra-nasal route were anaesthetised prior to dosing using isoflurane, and nitrous oxide in rat studies, or oxygen in mouse studies.

Animals were cannulated in the lateral tail vein and placed in a hot-box (37-40° C.) approximately 5 minutes before each sampling time-point to dilate the tail veins. Compounds were formulated as solutions for intravenous administration and as solutions or suspensions for all other methods. Animals were weighed on the day of dosing and received a single administration of the formulation with the volume adjusted according to the individual's bodyweight (Table 3). For serial samples, 150-200 µl rat blood samples or 20 µl mouse blood samples (with same volume addition of water) were taken from the cannula port into $K_2$EDTA-coated microtainers at pre-determined time-points over 24 hours. Plasma was isolated by centrifugation (8200 rcf for 5 minutes), in rat studies only.

At termination, blood samples were collected through the descending vena cava into $K_2$EDTA-coated microtainers and BAL fluid was obtained by flushing the lungs via the trachea with 3×4 ml instillations of 4% BSA in PBS for rats and 3×0.4 ml instillations of 4% BSA in PBS for mice. The lungs were excised, weighed and the weights recorded, and snap-frozen in liquid nitrogen.

Measurements of compound levels in the plasma or blood, lung homogenates and BAL fluid were determined by LC-MS/MS. Drug was extracted by protein precipitation using an excess of solvent containing an appropriate internal standard. Drug concentrations were determined against an external matrix-matched standard curve.

Figure 2:
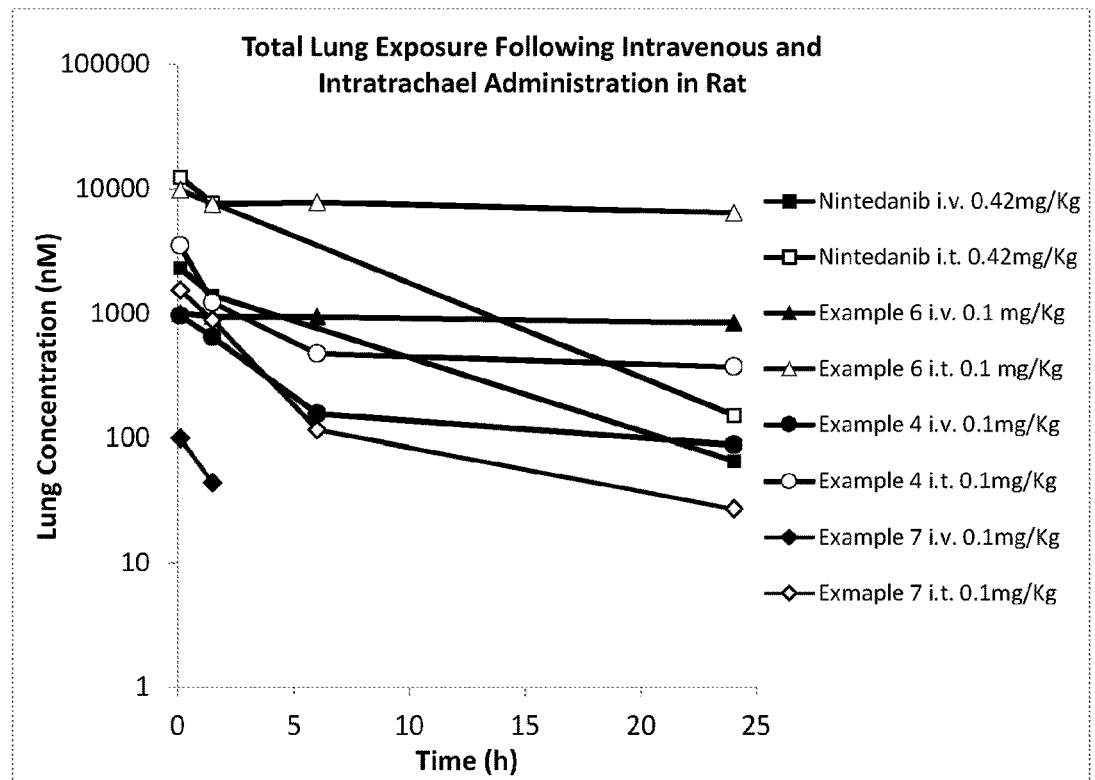
FIG. 2: shows the total lung exposure following intravenous and intra-tracheal administration of examples of the invention or nintedanib in rats (see results of pharmacokinetic measurements in rodents)
Figure 3:
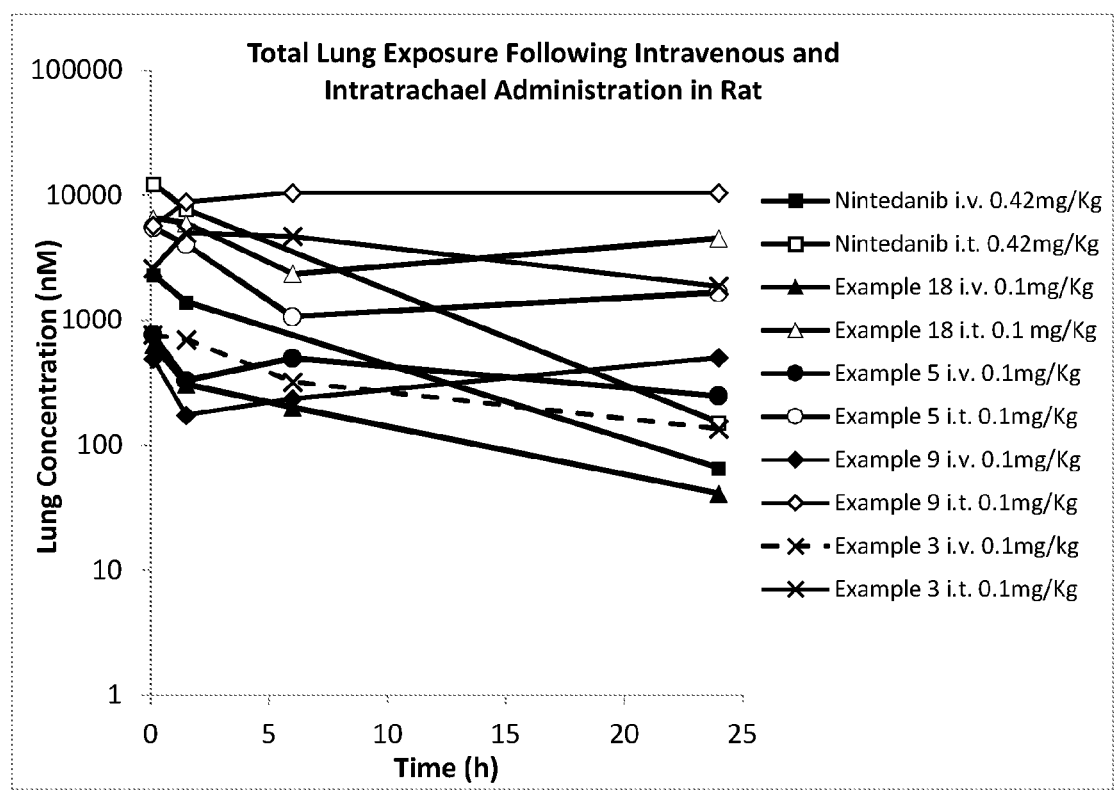
FIG. 3: shows the total lung exposure following intravenous and intra-tracheal administration of examples of the invention or nintedanib in rats (see results of pharmacokinetic measurements in rodents)

The drug concentrations were plotted against time on a semi-logarithmic plot (see FIGS. 2 and 3). Standard pharmacokinetic parameters were calculated using non-compartmental analysis. The concentrations in the lung and BAL fluid at each time point were expressed as the percentage of dose administered.

TABLE 3

| Volume of administration | | |
| --- | --- | --- |
| Route of administration | Mouse | Rat |
| Intranasal (i.n.) | 1.5 ml/kg | Not used |
| Intra-tracheal (i.t.) | Not used | 0.5 ml/kg |
| Oral (p.o.) | 10 ml/kg | 10 ml/kg |
| Intravenous (i.v.) | 2 ml/kg | 1 ml/kg |

Results

Results of testing in the enzyme inhibition assays and in the cellular and other in vitro assays are shown in Tables 4 to 8 below and FIGS. 1 to 3.

TABLE 4

The inhibitory activities of compounds of the invention and nintedanib against FGFR1, FGFR3, PDGFRα, PDGFRβ, VEGFR1 and VEGFR2.

Enzyme Assays

| Example number | $K_i$ (nM) | | | | | |
| --- | --- | --- | --- | --- | --- | --- |
| | FGFR1 | FGFR3 | PDGFRα | PDGFRβ | VEGFR1 | VEGFR2 |
| Nintedanib* | 32 | 5.9 | 8.4 | 8.0 | 113 | 3.8 |
| 1 | 35 | 13.8 | 12.3 | 9.93 | 97.6 | 22.9 |
| 2 | 44.9 | 14.8 | 18.2 | 11.1 | 123 | 28.8 |
| 3 | 34.1 | 12.9 | 10.7 | 6.86 | 73.1 | 27.7 |
| 4 | 29.3 | 8.07 | 11.3 | 11.6 | 74 | 16.7 |
| 5 | 43.7 | 10.4 | 12.2 | 12.9 | 72.6 | 36 |
| 6 | 28.4 | 7.35 | 9.41 | 10.3 | 80.8 | 21.2 |
| 7 | 35 | 15.7 | 7.82 | 5.76 | 146 | 23 |
| 8 | 41.8 | 17.1 | 10.9 | 8.12 | 150 | 18.8 |
| 9 | 38.7 | 9.42 | 8.36 | 7.89 | 133 | 17.3 |

TABLE 4-continued

The inhibitory activities of compounds of the invention and nintedanib against FGFR1, FGFR3, PDGFRα, PDGFRβ, VEGFR1 and VEGFR2.
Enzyme Assays

| Example number | $K_i$ (nM) | | | | | |
|---|---|---|---|---|---|---|
| | FGFR1 | FGFR3 | PDGFRα | PDGFRβ | VEGFR1 | VEGFR2 |
| 10 | 82.3 | 15.2 | 16.2 | 12.7 | 184 | 34.2 |
| 11 | 23.9 | 14.1 | 12.3 | 10.6 | 90.7 | 5.06 |
| 12 | 22.4 | 11.5 | 14.2 | 8.75 | 61.9 | 6.38 |
| 13 | 19.6 | 7.16 | 16.5 | 10.4 | 41.6 | 19.5 |
| 14 | 19.7 | 5.51 | 13.3 | 9.6 | 52.3 | 15.3 |
| 15 | 7.9 | 2.5 | 5.0 | 5.0 | 50 | 5.0 |
| 16 | 57.9 | 11.4 | 15.9 | 13 | 245 | 45.6 |
| 17 | 16.6 | 5.31 | 7.81 | 9.39 | 31.6 | 6.4 |
| 18 | 36.6 | 13.7 | 14.1 | 7.99 | 57.5 | 25.7 |
| 19 | 13.6 | 9.04 | 6.55 | 8.79 | 47.7 | 8.35 |
| 20 | 48.5 | 30 | 24.2 | 19.1 | 178 | 83.7 |
| 21 | 27.1 | 10.7 | 9.38 | 6.11 | 95.5 | 24.8 |
| 22 | 16.3 | 9.53 | 9.75 | 9.29 | 63.2 | 12.4 |
| 23 | 434 | 73.2 | 51.9 | 84.6 | 513 | 154 |
| 24 | 65.2 | 14.3 | 10.5 | 12.7 | 252 | 31.1 |
| 25 | 23.5 | 12.7 | 13 | 11.7 | 112 | 32.7 |
| 26 | 108 | 32.1 | 41 | 45 | 392 | 62.5 |
| 27 | 61 | 17.9 | 20.4 | 18 | 177 | 57.8 |
| 28 | 134 | 62.6 | 35.9 | 20 | 305 | 71.2 |
| 29 | 27.6 | 23.2 | 10.7 | 11.2 | 103 | 16.4 |
| 30 | 32.3 | 19.5 | 11 | 10 | 65.1 | 8 |
| 31 | 15.3 | 12.2 | 10.2 | 4.83 | 29.6 | 4.96 |
| 32 | 9.03 | 6.65 | 7.38 | 5.02 | 31.4 | 7.56 |
| 33 | 14.3 | 7.4 | 8.89 | 6.82 | 42.6 | 3.56 |
| 34 | 98.8 | 25.9 | 24.6 | 14.4 | 159 | 18.7 |
| 35 | 66.6 | 19.9 | 24.7 | 17 | 163 | 54.7 |
| 36 | 71.9 | 18.5 | 21.7 | 15.9 | 84.8 | 15 |
| 37 | 8.56 | 11.2 | 10.7 | 7.54 | 45.4 | 9.97 |
| 38 | 9.73 | 6.93 | 7.53 | 4.79 | 36.2 | 3.26 |
| 39 | 47.4 | 14.7 | 15.3 | 14.1 | 133 | 31.6 |
| 40 | 78.1 | 14.9 | 33.7 | 12.8 | 78.2 | 27 |
| 41 | 23.8 | 9.31 | 13.8 | 10.2 | 49.7 | 17.7 |
| 42 | 33.8 | 15.7 | 18.3 | 14.4 | 80.6 | 31.1 |
| 43 | 112 | 20.7 | 30.8 | 25.2 | 66.9 | 11.9 |
| 44 | 229 | 22 | 27.3 | 17.8 | 220 | 28.8 |
| 45 | 40.2 | 18.8 | 20 | 15.1 | 103 | 13 |
| 46 | 7.92 | 7.78 | 6.86 | 6.65 | 30.7 | 4.15 |
| 47 | 171 | 25.5 | 53.8 | 98.9 | 216 | 43.2 |
| 48 | 11.3 | 8.47 | 8.92 | 9.49 | 52.7 | 3.68 |
| 49 | 19.6 | 7.16 | 16.5 | 10.4 | 41.6 | 19.5 |
| 50 | 19.7 | 5.51 | 13.3 | 9.6 | 52.3 | 9.6 |
| 51 | 24.2 | 10.8 | ND | ND | 79.3 | 20.8 |
| 52 | 50.8 | 19.2 | ND | ND | 251 | 30.6 |
| 53 | 25.2 | 10.4 | ND | ND | 71.5 | 20.8 |
| 54 | 100 | 39.8 | 25.1 | 15.8 | 316 | 50.1 |
| 55 | 79.4 | 15.8 | 25.1 | 25.1 | 316 | 39.8 |
| 56 | 39.8 | 12.6 | 12.6 | 12.6 | 126 | 15.8 |

ND: Not determined;
n = 2 unless otherwise indicated (mean);
*n = 34

TABLE 5

The inhibitory effects of the compounds of the invention and nintedanib on phosphorylation of PDGFRβ in fibroblasts induced by PDGFBB in MRC5 cells and on phosphorylation of VEGFR2 in endothelial cells induced by $VEGF_{165}$.
Receptor Phosphorylation ($IC_{50}$ nM)

| Example number | PDGFBB-induced PDGFRβ phosphorylation in MRC5 cells | $VEGF_{165}$-induced VEGFR2 phosphorylation in HAEC cells |
|---|---|---|
| Nintedanib | 7.07 (n = 8) | 0.594 (n = 13) |
| 1 | 25.6 (n = 2) | 2.47 (n = 2) |
| 2 | 36.7 | 17.7 |
| 3 | 12.7 (n = 2) | 10.6 |
| 4 | 14 (n = 2) | 4.38 |
| 5 | 15 (n = 2) | 9.24 (n = 2) |
| 6 | 13.2 (n = 2) | 12.7 (n = 2) |
| 7 | 6.04 (n = 2) | 2.53 (n = 2) |
| 8 | 12 (n = 2) | 4.58 |
| 9 | 14.2 (n = 2) | 5.68 (n = 2) |

TABLE 5-continued

The inhibitory effects of the compounds of the invention and nintedanib on phosphorylation of PDGFRβ in fibroblasts induced by PDGFBB in MRC5 cells and on phosphorylation of VEGFR2 in endothelial cells induced by VEGF$_{165}$.
Receptor Phosphorylation (IC$_{50}$ nM)

| Example number | PDGFBB-induced PDGFRβ phosphorylation in MRC5 cells | VEGF$_{165}$-induced VEGFR2 phosphorylation in HAEC cells |
|---|---|---|
| 10 | 15.9 | 10.8 (n = 2) |
| 11 | 2.75 | 1.1 |
| 12 | 4.23 | 10.1 |
| 13 | 1.25 | 8.3 |
| 14 | 6.97 | 24.1 |
| 15 | 6.49 | 1.84 |
| 16 | ND | 8.89 |
| 17 | 4.48 | 3.11 |
| 18 | 16.8 (n = 2) | 8.15 (n = 2) |
| 19 | 5.04 | 0.765 |
| 20 | 38.9 | 17.1 |
| 21 | 35.1 | 23.6 |
| 22 | 12.3 | 31.9 |
| 23 | 22.6 | 942 |
| 24 | 12.3 | 4.96 |
| 25 | 24.2 | 10.8 |
| 26 | 18.1 | 4.08 |
| 27 | 43 | 16.7 |
| 28 | 51.3 | 14.9 |
| 29 | 3.65 | 3.46 |
| 30 | 6.02 | 0.204 |
| 31 | 5.52 | 2.99 |
| 32 | 4.53 | 3.88 |
| 33 | 2.32 | ND |
| 34 | 4.71 | 6.88 |
| 35 | 17.3 | 11.6 |
| 36 | 9.96 | 7.61 |
| 37 | 5.28 | 4.63 |
| 38 | 1.7 | 8.78 |
| 39 | 5.95 | 2.11 |
| 40 | 13.4 | 72.2 |
| 41 | 7.4 | 5.82 |
| 42 | 14.9 | 28.3 |
| 43 | 2.31 | ND |
| 44 | 3.33 | 6.99 |
| 45 | 2.42 | 3.16 |
| 46 | 2.49 | 1.5 |
| 47 | 3.67 | 3.17 |
| 48 | 2.29 | ND |
| 49 | 1.25 | 8.3 |
| 50 | 6.97 | 24.1 |
| 51 | 6.71 | 10.5 |
| 52 | 5.49 | 4.28 |
| 53 | 6.5 | 4.58 |
| 54 | 5.04 | 6.29 |
| 55 | 9.13 | 10.2 |
| 56 | 9.16 | 6.68 |

ND: Not determined;
n = 1 unless otherwise indicated

TABLE 6

The effect of the compounds of the invention and nintedanib on cell viability of MRC5 cells (MTT assay).
Cell viability assay in MRC5 cells (MTT)

| Example number | Cell viability at 1000 nM (%) | Cell viability at 300 nM (%) | Cell viability at 100 nM (%) |
|---|---|---|---|
| Nintedanib (n = 30) | 92.7 | 105.6 | 104.6 |
| 1 (n = 4) | 68.7 | 89 | 103.6 |
| 2 | 68.5 | 91 | 94 |
| 3 (n = 4) | 79.5 | 86.1 | 88 |
| 4 (n = 4) | 70.9 | 83.2 | 80.6 |
| 5 (n = 4) | 84.8 | 81 | 91.5 |
| 6 (n = 4) | 91.2 | 98.9 | 102.3 |
| 7 (n = 3) | 67.5 | 97.2 | 102.9 |
| 8 (n = 3) | 77.7 | 108.2 | 110.4 |
| 9 (n = 3) | 97.5 | 103.6 | 102 |
| 10 | 108.4 | 118.9 | 85 |
| 11 | 28.5 | 67.8 | 82 |
| 12 | 93.4 | 105.5 | 92.2 |
| 13 | 102.1 | 93.2 | 84.3 |
| 14 | 61 | 107.9 | 116.2 |
| 15 | 85.6 | 109.9 | 91.3 |
| 16 | 70.6 | 104.3 | 103.2 |
| 17 (n = 3) | 34.1 | 63.6 | 76.2 |
| 18 (n = 4) | 91.8 | 97.3 | 98.2 |
| 19 | 21.9 | 71.8 | 85.5 |
| 20 | 87.2 | 91.7 | 92.6 |
| 21 | 98.8 | 127.3 | 139.6 |
| 22 | 48.8 | 58.8 | 72.3 |
| 23 | 62.1 | 100.5 | 90.7 |
| 24 | 45.9 | 74.4 | 125.2 |
| 25 | 55.4 | 74.7 | 83.2 |
| 26 | 57.6 | 91.6 | 84.4 |
| 27 | 82.9 | 112.6 | 106.5 |
| 28 | 83.6 | 97.6 | 149.4 |
| 29 | 60.8 | 72.5 | 116.9 |
| 30 | 16.4 | 85.3 | 107.2 |
| 31 | 34.3 | 47.3 | 69.3 |
| 32 | 49.4 | 129.3 | 99.3 |
| 33 | 19.8 | 63.1 | 86.6 |
| 34 | 16.2 | 74.4 | 82.9 |
| 35 | 99.1 | 122.5 | 99.8 |
| 36 | 69.6 | 77.2 | 87.3 |
| 37 | 18.4 | 83.4 | 93.6 |
| 38 | 4.2 | 63 | 70.7 |
| 39 | 36.7 | 73.3 | 96.2 |
| 40 | 82.9 | 88 | 95.4 |
| 41 | 6.2 | 56.8 | 68.5 |
| 42 | 60.7 | 83.4 | 82.5 |
| 43 | 6.4 | 58.8 | 72.2 |
| 44 | 60.4 | 78.4 | 98.4 |
| 45 | 62.8 | 71.7 | 80.1 |
| 46 | 18.2 | 80.2 | 87 |
| 47 | 58.5 | 123 | 143.1 |
| 48 | 14.1 | 74.4 | 84.4 |
| 49 | 102.1 | 93.2 | 84.3 |
| 50 | 61.0 | 107.9 | 116.2 |
| 51 | 83.8 | 95.5 | 113 |
| 52 | 85.9 | 81.2 | 81.3 |
| 53 | 95.3 | 92.9 | 89.1 |
| 54 | 92.4 | 105.5 | 110.2 |
| 55 | 101.7 | 101.5 | 79.4 |
| 56 | 102.0 | 104.9 | 100.0 | n = 1 unless otherwise indicated

TABLE 7

Determination of P$_{app}$ for compounds of the invention in the PAMPA permeability assay

| Example No | Mean P$_{app}$ (10$^{-6}$ cm s$^{-1}$) | Papp SD | Papp N | % Recovery |
|---|---|---|---|---|
| Nintedanib | 0.277 | 0.151 | 4 | 83.5 |
| Nintedanib (repeat) | 0.129 | 0.0547 | 4 | 64.0 |
| 1 | 0.123 | 0.0586 | 4 | 92.0 |
| 2 | ND | ND | ND | ND |
| 3 | 0.00775 | 0.00480 | 2 | 92.4 |
| 4 | 0.0216 | 0.00968 | 4 | 76.0 |

TABLE 7-continued

Determination of $P_{app}$ for compounds of the invention in the PAMPA permeability assay PAMPA assay data

| Example No | Mean $P_{app}$ ($10^{-6}$ cm s$^{-1}$) | Papp SD | Papp N | % Recovery |
|---|---|---|---|---|
| 5 | 0.00254 | 0.000276 | 4 | 58.7 |
| 6 | 0.0120 | 0.00415 | 4 | 56.5 |
| 7 | 0.00653 | 0.00208 | 4 | 56.3 |
| 8 | 0.156 | 0.0925 | 4 | 87.8 |
| 9 | 0.0146 | 0.0144 | 3 | 72.7 |
| 10 | 0.0428 | 0.0207 | 3 | 70.4 |
| 11 | 0.0479 | 0.0136 | 4 | 93.2 |
| 12 | 0.00638 | 0.000688 | 2 | 87.7 |
| 13 | 0.0439 | ND | 1 | 76.3 |
| 14 | ND | ND | ND | ND |
| 15 | ND | ND | ND | ND |
| 16 | ND | ND | ND | ND |
| 17 | 24.6 | 6.76 | 4 | 59.8 |
| 18 | 0.00383 | ND | 1 | 84.5 |
| 19 | 0.589 | 0.189 | 4 | 61.8 |
| 20 | 0.0165 | 0.00927 | 4 | 104 |
| 21 | 0.0442 | 0.0182 | 4 | 76.0 |
| 22 | 0.0460 | 0.00625 | 4 | 101 |
| 23 | ND | ND | ND | ND |
| 24 | ND | ND | ND | ND |
| 25 | 11.0 | 4.21 | 4 | 105 |
| 26 | 10.3 | 1.09 | 4 | 96.2 |
| 27 | 16.8 | 5.25 | 4 | 54.3 |
| 28 | ND | ND | ND | ND |
| 29 | 0.373 | 0.0168 | 4 | 72.1 |
| 30 | 0.0235 | 0.00544 | 4 | 87.2 |
| 31 | 0.00531 | 0.00133 | 4 | 66.2 |
| 32 | 0.0217 | 0.00799 | 4 | 59.6 |
| 33 | 0.0269 | 0.0117 | 4 | 69.1 |
| 34 | 0.00748 | 0.00338 | 3 | 41.1 |
| 35 | 10.7 | 4.14 | 4 | 79.2 |
| 36 | 8.96 | 3.22 | 4 | 77.4 |
| 37 | 0.0542 | 0.0147 | 4 | 68.2 |
| 38 | 0.0269 | 0.0154 | 4 | 70.3 |
| 39 | 0.633 | 0.124 | 4 | 85.7 |
| 40 | 26.5 | 11.6 | 4 | 56.0 |
| 41 | ND | ND | ND | ND |
| 42 | ND | ND | ND | ND |
| 43 | 0.865 | 0.211 | 2 | 72.2 |
| 44 | 0.00879 | 0.00701 | 2 | 71.7 |
| 45 | 0.0893 | 0.0140 | 2 | 77.0 |
| 46 | ND | ND | ND | ND |
| 47 | ND | ND | ND | ND |
| 48 | ND | ND | ND | ND |
| 49 | ND | ND | ND | ND |
| 50 | ND | ND | ND | ND |
| 51 | ND | ND | ND | ND |
| 52 | ND | ND | ND | ND |
| 53 | ND | ND | ND | ND |
| 54 | ND | ND | ND | ND |
| 55 | ND | ND | ND | ND |
| 56 | ND | ND | ND | ND |

ND = not determined

TABLE 8

Pharmacokinetic measurements over a period of 24 hours in rats dosed intravenously (i.v.) and intra-tracheally (i.t.) with compounds of the invention or nintedanib.

| | Example Number | | | | | | | |
|---|---|---|---|---|---|---|---|---|
| | Nintedanib | 3 | 4 | 5 | 6 | 7 | 9 | 18 |
| | i.v. dosing studies | | | | | | | |
| i.v. dose | 0.42 | 0.1 | 0.1 | 0.1 | 0.1 | 0.1 | 0.1 | 0.1 |
| CL (ml/min/kg) | 124 | ND | ND | ND | ND | 75 | 90 | ND |
| Vss (L/kg) | 28 | ND | ND | ND | ND | 3.4 | 7 | ND |
| t1/2 (h) | 3.9 | ND | ND | ND | ND | 0.6 | 1.1 | 5.1 |
| MRT (h) | 3.8 | ND | ND | ND | ND | 0.7 | 1.1 | ND |
| lung concentration (nM) at time (h) | | | | | | | | |
| 0.1 | 2304 | 761 | 959 | 765 | 1002 | 99 | 494 | 638 |
| 1.5 | 1392 | 700 | 641 | 330 | 949 | 44 | 174 | 306 |
| 6 | ND | 321 | 156 | 499 | 939 | BQL | 235 | 201 |
| 24 | 66 | 135 | 88 | 247 | 837 | BQL | 502 | 41 |
| lung/plasma ratio at time (h) | | | | | | | | |
| 0.1 | 92 | 38 | 86 | 127 | 77 | 2 | 17 | 39 |
| 1.5 | 226 | 154 | 137 | >188 | >558 | 12 | 55 | 69 |
| 6 | ND | 120 | 58 | >284 | >552 | NC | >326 | 71 |
| 24 | >80 | >72 | >50 | >140 | >492 | NC | >697 | >21.5 |
| BAL % administered dose at time (h) | | | | | | | | |
| 0.1 | | 0.06 | 0.1 | 0.07 | BQL | BQL | 0.06 | BQL | 0.13 |
| 1.5 | | 0.03 | 0.1 | 0.04 | BQL | BQL | BQL | BQL | 0 |

TABLE 8-continued

Pharmacokinetic measurements over a period of 24 hours in rats dosed intravenously (i.v.) and intra-tracheally (i.t.) with compounds of the invention or nintedanib.

| | \multicolumn{8}{c}{Example Number} |
|---|---|---|---|---|---|---|---|---|
| | Nintedanib | 3 | 4 | 5 | 6 | 7 | 9 | 18 |
| 6 | ND | 0.03 | BQL | BQL | BQL | BQL | BQL | BQL |
| 24 | BQL | 0.02 | BQL | BQL | BQL | BQL | BQL | BQL |
| \multicolumn{9}{c}{i.t. dosing studies} |
| i.t. dose | 0.42 | 0.1 | 0.1 | 0.1 | 0.1 | 0.1 | 0.1 | 0.1 |
| i.t. BAV (%) | 43 | ND | ND | ND | ND | 35 | <40 | 39 |
| lung concentration (nM) at time (h) | | | | | | | | |
| 0.1 | 12396 | 2605 | 3490 | 5506 | 9826 | 1532 | 5701 | 6533 |
| 1.5 | 7699 | 4986 | 1214 | 4022 | 7568 | 886 | 8813 | 5987 |
| 6 | ND | 4675 | 475 | 1067 | 7815 | 116 | 10466 | 2351 |
| 24 | 152 | 1863 | 370 | 1674 | 6438 | 27 | 10465 | 4523 |
| lung/plasma conc ratio at time (h) | | | | | | | | |
| 0.1 | 1227 | 100 | 290 | 371 | 472 | 39 | >7890 | 346 |
| 1.5 | 1607 | 1911 | 523 | >2285 | >4452 | >265 | >12197 | 2318 |
| 6 | ND | 2152 | 251 | >606 | >4597 | >35 | >14485 | 1197 |
| 24 | >183 | >1004 | >206 | >951 | >3787 | >8 | >14483 | >2373 |
| BAL % administered dose at time (h) | | | | | | | | |
| 0.1 | 2 | 14 | 3.4 | 13.6 | 14 | 3.5 | 13.7 | 6.7 |
| 1.5 | 1 | 1.2 | 0.4 | 0.9 | 0.9 | 0.6 | 5.2 | 2.2 |
| 6 | ND | 0.7 | 0.4 | 0.2 | 1.1 | 0.1 | 2.3 | 0.4 |
| 24 | 0.1 | 0.3 | 0.3 | 0.2 | 0.9 | BQL | 0.5 | 0.3 |
| Lung conc i.t./i.v. Ratio at time (h) | | | | | | | | |
| 0.1 | 5.4 | 3 | 3.6 | 7 | 9.8 | 15.5 | 12 | 10 |
| 1.5 | 5.5 | 7 | 1.9 | 12 | 8.0 | 20.1 | 51 | 20 |
| 6 | ND | 15 | 3.0 | 2 | 8.3 | >42 | 45 | 12 |
| 24 | 2.3 | 14 | 4.2 | 7 | 7.7 | >10 | 21 | 110 |
| \multicolumn{9}{c}{Oral dosing studies} |
| Oral dose (mg/kg) | — | 3 | 3 | 3 | 3 | 3 | 3 | 3 |
| Oral BAV (%) | — | ND | ND | ND | ND | <7 | <2 | ND |

ND: Not determined
NC: Not calculable due to one parameter being BLQ
BLQ: Below level of Quantitation
CL: Clearance
Vss: Volume of Distribution
MRT: Mean Residence Time
BAV: Bioavailability
BAL: Bronchoalveolar Lavage
Where a > or < value is reported the value is based on the Lower Limit of Quantification from the bioanalytical method.

Summary of Results

The compounds of the invention, as disclosed herein, demonstrate inhibitory activity against FGFR1, FGFR3, PDGFRα, PDGFRβ, VEGFR1 and VEGFR2 (Table 4 and Table 5) and nanomolar potency. A vast majority of the tested compounds show no adverse effects in the cell viability assays (Table 6). Furthermore, the compounds generally have low permeability across membranes (Table 7 and FIG. 1). The pharmacokinetic measurements show that generally the compounds of the invention are found to have a higher relative content remaining in the lung 24 hours following topical delivery after the subject receives the dose than nintedanib (Table 8 and FIGS. 2 and 3). The pharmacokinetic parameters also indicate that compounds of the invention maintain higher lung levels when delivered topically compared to equivalent doses delivered i.v. and generally these higher relative levels are higher than the corresponding levels for nintedanib particularly at the 24 h timepoint. The low BAL levels noted together with the reducing amounts over a 24 h period indicate dissolution and absorption into the lung tissue is occurring with compounds of the invention.

This profile indicates that compounds of the invention are expected to be suitable as medicines inter alia for the treatment of fibrotic diseases or interstitial lung diseases, such as IPF, or respiratory disorders, especially when delivered topically to the lung.

REFERENCES

Castriotta R J, et al., *Chest*, 2010, 138(3):693-703
Du Bois R M., *Nat Rev Drug Discov.*, 2010, 9(2):129-40
Fehrenbach. H., et al., *Virchows Arch.*, 1999, 435(1):20-31
King T E Jr, et al., *Lancet*, 2011, 3; 378(9807):1949-61
Lindroos. P., *Am J Physio Lung Cell Mol Physiol.*, 2001, 280:L354-L362
Tronde Ann et al., *J Pharm. Sci.*, 2003, 92(6), 1216-33
Selman M, et al., *Ann Intern Med.*, 2001, 16; 134(2):136-51
Wohnsland F et al., *Med Chem.*, 2001, 44; 923-930

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The invention claimed is:
1. A compound of formula (I):

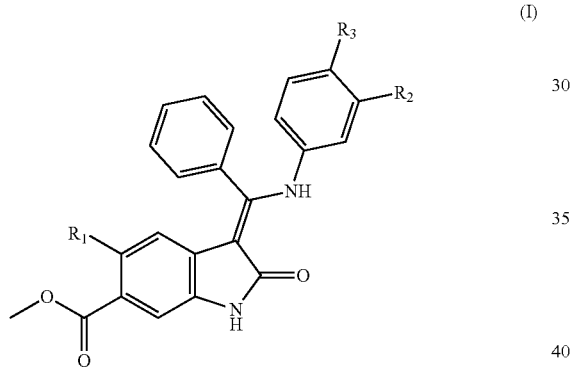

wherein
$R_1$ represents Me, Et, CH=CH$_2$, C≡C—H or C≡C-Me;
one of $R_2$ and $R_3$ represents a group selected from H, $C_1$-$C_6$alkyl, $C_1$-$C_6$alkoxy, $C_3$-$C_8$cycloalkyl, —CH$_2$—($C_3$-$C_8$cycloalkyl), halogen and cyano, and the other represents the group —Z—$R_x$;
$R_x$ represents formula (i)

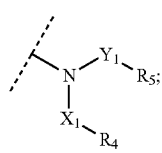

formula (ii)

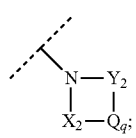

or formula (iii)

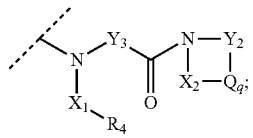

Z represents CO or SO$_2$;
$Y_1$ represents (CH$_2$)$_n$ and, except when n represents 0, may optionally be substituted by Me;
$X_1$ represents (CH$_2$)$_m$ and, except when m represents 0, may optionally be substituted by Me;
n and m independently represent 0, 1, 2, 3, 4 or 5;
$Y_2$ represents (CH$_2$)$_s$ and may optionally be substituted on the same or different carbon atoms by one or more groups selected from Me, OH, —C$_0$-C$_4$alkyleneCONR$_6$R$_7$, —C$_0$-C$_4$alkyleneNR$_6$COR$_7$, —C$_1$-C$_4$hydroxyalkyl, —C$_1$-C$_4$alkylNR$_8$R$_9$ and —C$_0$-C$_4$alkyl-Het;
$X_2$ represents (CH$_2$)$_v$ and may optionally be substituted on the same or different carbon atoms by one or more groups selected from Me, OH, —C$_0$-C$_4$alkyleneCONR$_{10}$R$_{11}$, —C$_0$-C$_4$alkyleneNR$_{10}$COR$_{11}$, —C$_1$-C$_4$hydroxyalkyl, —C$_1$-C$_4$alkylNR$_{12}$R$_{13}$ and —C$_0$-C$_4$alkyl-Het;
Q represents spiro-C or a heteroatom selected from N, O and S and if N may optionally be substituted with one or more groups selected from —C$_1$-C$_4$alkyl, —C$_1$-C$_4$hydroxyalkyl, —C$_2$-C$_4$alkylNR$_{12}$R$_{13}$, —C$_0$-C$_4$alkyl-Het, —C$_1$-C$_4$alkyleneCONR$_{14}$R$_{15}$ and —C$_2$-C$_4$alkyleneNR$_{14}$COR$_{15}$;
Het represents a 4-8 membered aliphatic heterocycle containing one or more heteroatoms independently selected from N, O and S, optionally containing a carbonyl group and optionally substituted by one or more Me groups;
q represents 0 or 1;
s and v independently represent 2 or 3 save that s+v+q=3, 4, 5, 6 or 7;
spiro-C is a quaternary carbon atom which joins a 4-8 membered aliphatic heterocycle containing one or more heteroatoms independently selected from N, O and S, optionally containing a carbonyl group and optionally substituted by one or more Me groups, to the heterocycle comprising N, X$_2$ and Y$_2$;
$Y_3$ represents (CH$_2$)$_t$;
t represents 1, 2, 3 or 4;
$R_4$ represents H, OH, NR$_{16}$R$_{17}$, C$_3$-C$_5$cycloalkyl or a 4-8 membered aliphatic heterocycle containing one or more heteroatoms independently selected from N, O and S, save that when R$_4$ is OH or NR$_{16}$R$_{17}$, m is 2, 3, 4 or 5;
$R_5$ represents H, OH, NR$_{18}$R$_{19}$, C$_3$-C$_5$cycloalkyl or a 4-8 membered aliphatic heterocycle containing one or more heteroatoms independently selected from N, O and S, save that when R$_5$ is OH or NR$_{18}$R$_{19}$, n is 2, 3, 4 or 5;
in which the aliphatic heterocycle groups that R$_4$ and R$_5$ may represent may optionally contain a carbonyl or sulphone group and the C$_3$-C$_5$cycloalkyl and the aliphatic heterocycle groups that R$_4$ and R$_5$ may represent may optionally be substituted by one or more groups selected from —C$_1$-C$_4$alkyl, —C$_1$-C$_4$hydroxyalkyl, C$_1$-C$_4$alkoxy(C$_1$-C$_4$)alkyl-, —C$_1$-

$C_4$alkyleneCONR$_{20}$R$_{21}$, —C$_1$-C$_4$alkyleneNR$_{20}$COR$_{21}$, —SO$_2$(C$_1$-C$_4$)alkyl, —CO(C$_1$-C$_4$)alkyl, halogen, CN, OH and NR$_{22}$R$_{23}$;

R$_6$, R$_7$, R$_{10}$, R$_{11}$, R$_{14}$ and R$_{15}$ independently represent H, —C$_1$-C$_4$alkyl, —C$_1$-C$_4$hydroxyalkyl, C$_1$-C$_4$alkoxy(C$_1$-C$_4$)alkyl- or —C$_1$-C$_4$alkylN(C$_1$-C$_4$alkyl)$_2$;

R$_{16}$, R$_{17}$, R$_{18}$, R$_{19}$ independently represent H, or —C$_1$-C$_4$alkyl optionally substituted by one or more groups selected from OH, oxo, NR$_{24}$R$_{25}$ and C$_1$-C$_4$alkoxy-; and R$_8$, R$_9$, R$_{12}$, R$_{13}$, R$_{20}$, R$_{21}$, R$_{22}$, R$_{23}$, R$_{24}$ and R$_{25}$ independently represent H or —C$_1$-C$_4$alkyl;

or a pharmaceutically acceptable salt thereof.

2. A compound of formula (I) according to claim 1 wherein R$_2$ represents a group selected from H, —C$_1$-C$_6$alkyl, C$_1$-C$_6$alkoxy-, —C$_3$-C$_8$cycloalkyl, —CH$_2$—(C$_3$-C$_8$cycloalkyl), halogen and cyano and R$_3$ represents the group —Z—R$_x$.

3. A compound of formula (I) according to claim 1 wherein R$_2$ represents the group —Z—R$_x$ and R$_3$ represents a group selected from H, —C$_1$-C$_6$alkyl, C$_1$-C$_6$alkoxy-, —C$_3$-C$_8$cycloalkyl, —CH$_2$—(C$_3$-C$_8$cycloalkyl), halogen and cyano.

4. A compound of formula (I) according to claim 1 wherein R$_1$ represents Me.

5. A compound of formula (I) according to claim 1 wherein R$_2$ represents H, Me or F.

6. A compound of formula (I) according to claim 1 wherein Z represents CO.

7. A compound of formula (I) according to claim 1 wherein Z represents SO$_2$.

8. A compound of formula (I) according to claim 1 wherein R$_x$ is represented by formula (i).

9. A compound of formula (I) according to claim 1 wherein R$_x$ is represented by formula (ii).

10. A compound of formula (I) according to claim 1 wherein R$_x$ is represented by formula (iii).

11. A compound of formula (I) according to claim 1 of formula (A):

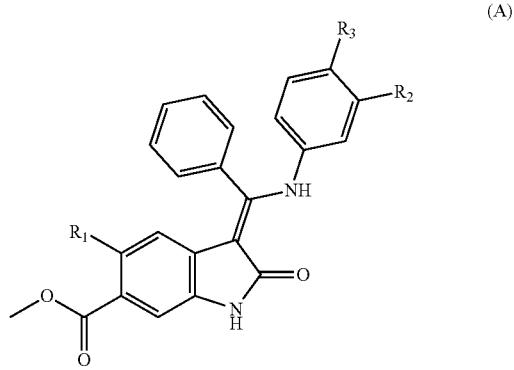

(A)

wherein
R$_1$ represents Me, Et, CH=CH$_2$, C≡C—H or C≡C-Me;
one of R$_2$ and R$_3$ represents a group selected from H, —C$_1$-C$_6$alkyl, C$_1$-C$_6$alkoxy, —C$_3$-C$_8$cycloalkyl, —CH$_2$—(C$_3$-C$_8$cycloalkyl), halogen and cyano, and the other represents the group —Z—R$_x$,
Z represents CO or SO$_2$;

R$_x$ represents formula (iv):

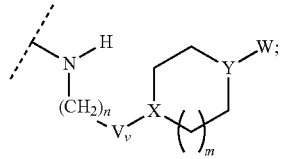

wherein V represents CO;
wherein v represents 0 or 1;
wherein n represents 0, 1 or 2, except that when v represents 1, n represents 1 or 2;
m represents 1 or 2;
X represents CH or N, except that when n represents 0 or 1, X represents CH;
Y represents CH or N;
W represents a group selected from —C$_1$-C$_4$alkyl, —C$_1$-C$_4$hydroxyalkyl, C$_1$-C$_4$alkoxy(C$_1$-C$_4$)alkyl-, —C$_1$-C$_4$alkyleneCONR$_{20}$R$_{2i}$, —C$_1$-C$_4$alkyleneNR$_{20}$COR$_{21}$, —SO$_2$(C$_1$-C$_4$)alkyl, —CO(C$_1$-C$_4$)alkyl, halogen, CN, OH and NR$_{22}$R$_{23}$ except that when W represents NR$_{22}$R$_{23}$, —C$_1$alkyleneNR$_{20}$COR$_{21}$ or halogen, Y represents CH;
R$_{20}$, R$_{21}$, R$_{22}$, R$_{23}$, R$_{24}$ and R$_{25}$ independently represent H or —C$_1$-C$_4$alkyl;
or a pharmaceutically acceptable salt thereof.

12. A compound of formula (I) according to claim 1 which is selected from:
(Z)-Methyl 5-methyl-3-(((4-(N-(2-(4-methylpiperazin-1-yl)ethyl)sulfamoyl)phenyl)amino)(phenyl)methylene)-2-oxoindoline-6-carboxylate;
(Z)-Methyl 3-(((4-((2-(dimethylamino)ethyl)carbamoyl)phenyl)amino)(phenyl)methylene)-5-methyl-2-oxoindoline-6-carboxylate;
(Z)-Methyl 5-methyl-3-(((4-(((1-methylpiperidin-4-yl)methyl)carbamoyl)phenyl)amino)(phenyl)methylene)-2-oxoindoline-6-carboxylate;
(Z)-Methyl 5-methyl-3-(((4-((2-(4-methylpiperazin-1-yl)ethyl)carbamoyl)phenyl)amino)(phenyl)methylene)-2-oxoindoline-6-carboxylate;
(Z)-Methyl 5-methyl-3-(((4-((2-(4-methyl-1,4-diazepan-1-yl)ethyl)carbamoyl)phenyl)amino)(phenyl)methylene)-2-oxoindoline-6-carboxylate;
(Z)-Methyl 3-(((4-((2-(4-(dimethylamino)piperidin-1-yl)ethyl)carbamoyl)phenyl)amino)(phenyl)methylene)-5-methyl-2-oxoindoline-6-carboxylate;
(Z)-Methyl 3-(((4-((2-(4-(2-hydroxyethyl)piperazin-1-yl)-2-oxoethyl)carbamoyl)phenyl)amino)(phenyl)methylene)-5-methyl-2-oxoindoline-6-carboxylate;
(Z)-Methyl 5-methyl-3-(((4-42-(4-methylpiperazin-1-yl)-2-oxoethyl)carbamoyl)phenyl)amino)(phenyl)methylene)-2-oxoindoline-6-carboxylate;
(Z)-Methyl 5-methyl-2-oxo-3-(((4-((2-(3-oxopiperazin-1-yl)ethyl)carbamoyl)phenyl)amino)(phenyl)methylene)indoline-6-carboxylate;
(Z)-Methyl 5-methyl-3-(((4-((3-(4-methylpiperazin-1-yl)-3-oxopropyl)carbamoyl)phenyl)amino)(phenyl)methylene)-2-oxoindoline-6-carboxylate;
(Z)-Methyl 5-methyl-3-(((4-(4-(2-(methylamino)-2-oxoethyl)piperazine-1-carbonyl)phenyl)amino)(phenyl)methylene)-2-oxoindoline-6-carboxylate;
(Z)-Methyl 3-(((4-((2-(4-hydroxypiperidin-1-yl)ethyl)carbamoyl)phenyl)amino)(phenyl)methylene)-5-methyl-2-oxoindoline-6-carboxylate;

(Z)-Methyl 3-(((4-((1-(2-hydroxyethyl)piperidin-4-yl)carbamoyl)phenyl)amino)(phenyl)methylene)-5-methyl-2-oxoindoline-6-carboxylate;

(Z)-Methyl 3-(((4-(((1-(2-hydroxyethyl)piperidin-4-yl)methyl)carbamoyl)phenyl)amino)(phenyl)methylene)-5-methyl-2-oxoindoline-6-carboxylate;

(Z)-Methyl 3-(((4-(4-(2-((2-hydroxyethyl)amino)-2-oxoethyl)piperazine-1-carbonyl)phenyl)amino)(phenyl)methylene)-5-methyl-2-oxoindoline-6-carboxylate;

(Z)-Methyl 3-(((3-((2-(dimethylamino)ethyl)(methyl)carbamoyl)phenyl)amino)(phenyl)methylene)-5-methyl-2-oxoindoline-6-carboxylate;

(Z)-Methyl 5-methyl-3-(((4-(4-methylpiperazine-1-carbonyl)phenyl)amino)(phenyl)methylene)-2-oxoindoline-6-carboxylate;

(Z)-Methyl-5-methyl-3-(((4-((1-methylpiperidin-4-yl)carbamoyl)phenyl)amino)(phenyl)methylene)-2-oxoindoline-6-carboxylate;

(Z)-Methyl 3-(((4-(4-(2-hydroxyethyl)piperazine-1-carbonyl)phenyl)amino)(phenyl)methylene)-5-methyl-2-oxoindoline-6-carboxylate;

(Z)-Methyl 3-(((4-((1-(2-methoxyethyl)piperidin-4-yl)carbamoyl)phenyl)amino)(phenyl)methylene)-5-methyl-2-oxoindoline-6-carboxylate;

(Z)-Methyl-5-methyl-3-(((4-((3-(4-methylpiperazin-1-yl)propyl)carbamoyl)phenyl)amino)(phenyl)methylene)-2-oxoindoline-6-carboxylate;

(Z)-Methyl 3-(((4-((3-(dimethylamino)propyl)carbamoyl)phenyl)amino)(phenyl)methylene)-5-methyl-2-oxoindoline-6-carboxylate;

(Z)-Methyl 3-(((4-((2-(4,4-difluoropiperidin-1-yl)ethyl)carbamoyl)phenyl)amino)(phenyl)methylene)-5-methyl-2-oxoindoline-6-carboxylate;

(Z)-Methyl 3-(((4-((2-(4-acetylpiperazin-1-yl)ethyl)carbamoyl)phenyl)amino)(phenyl)methylene)-5-methyl-2-oxoindoline-6-carboxylate;

(Z)-Methyl 3-(((4-(N-(2-(dimethylamino)ethyl)sulfamoyl)phenyl)amino)(phenyl)methylene)-5-methyl-2-oxoindoline-6-carboxylate;

(Z)-Methyl 3-(((4-((4-(2-hydroxyethyl)piperazin-1-yl)sulfonyl)phenyl)amino)(phenyl)methylene)-5-methyl-2-oxoindoline-6-carboxylate;

(S,Z)-Methyl 5-methyl-3-(((4-((1-methylpiperidin-3-yl)carbamoyl)phenyl)amino)(phenyl)methylene)-2-oxoindoline-6-carboxylate;

(Z)-Methyl 3-(((4-(4-fluoropiperidin-1-yl)ethyl)carbamoyl)phenyl)amino)(phenyl)methylene)-5-methyl-2-oxoindoline-6-carboxylate;

(Z)-Methyl 5-methyl-3-(((4-((3-morpholinopropyl)carbamoyl)phenyl)amino)(phenyl)methylene)-2-oxoindoline-6-carboxylate;

(Z)-Methyl 5-methyl-3-(((4-(1-methyl-5-oxo-1,4,9-triazaspiro[5.5]undecane-9-carbonyl)phenyl)amino)(phenyl)methylene)-2-oxoindoline-6-carboxylate;

(Z)-Methyl 3-(((4-(4-((2-(dimethylamino)ethyl)carbamoyl)piperidine-1-carbonyl)phenyl)amino)(phenyl)methylene)-5-methyl-2-oxoindoline-6-carboxylate;

(Z)-Methyl 3-(((4-((2-(dimethylamino)ethyl)(2-hydroxyethyl)carbamoyl)phenyl)amino)(phenyl)methylene)-5-methyl-2-oxoindoline-6-carboxylate;

(Z)-Methyl 3-(((4-((3S,4S)-4-((dimethylamino)methyl)-3-hydroxypiperidine-1-carbonyl)phenyl)amino)(phenyl)methylene)-5-methyl-2-oxoindoline-6-carboxylate;

(Z)-Methyl 3-(((4-((2-(4-acetyl-1,4-diazepan-1-yl)ethyl)carbamoyl)phenyl)amino)(phenyl)methylene)-5-methyl-2-oxoindoline-6-carboxylate;

(Z)-Methyl 3-(((4-((2-((2-methoxyethyl)(methyl)amino)ethyl)carbamoyl)phenyl)amino)(phenyl)methylene)-5-methyl-2-oxoindoline-6-carboxylate;

(Z)-Methyl 3-(((4-(((4-(dimethylamino)tetrahydro-2H-pyran-4-yl)methyl)carbamoyl)phenyl)amino)(phenyl)methylene)-5-methyl-2-oxoindoline-6-carboxylate;

(Z)-Methyl-3-(((4-(4-hydroxy-4-(pyrrolidin-1-ylmethyl)piperidine-1-carbonyl)phenyl)amino)(phenyl)methylene)-5-methyl-2-oxoindoline-6-carboxylate;

(Z)-Methyl-3-(((4-(4-((dimethylamino)methyl)-4-(hydroxymethyl)piperidine-1-carbonyl)phenyl)amino)(phenyl)methylene)-5-methyl-2-oxoindoline-6-carboxylate;

(Z)-Methyl-3-(((4-(4-(2-((2-methoxyethyl)amino)-2-oxoethyl)piperazine-1-carbonyl)phenyl)amino)(phenyl)methylene)-5-methyl-2-oxoindoline-6-carboxylate;

(Z)-Methyl 3-(((4-(((1-(dimethylamino)cyclobutyl)methyl)carbamoyl)phenyl)amino)(phenyl)methylene)-5-methyl-2-oxoindoline-6-carboxylate;

(Z)-Methyl 3-(((4-((1-(2-hydroxyethyl)piperidin-4-yl)(methyl)carbamoyl)phenyl)amino)(phenyl)methylene)-5-methyl-2-oxoindoline-6-carboxylate;

(Z)-Methyl 3-(((4-((2-(4-(hydroxymethyl)piperidin-1-yl)ethyl)carbamoyl)phenyl)amino)(phenyl)methylene)-5-methyl-2-oxoindoline-6-carboxylate;

(Z)-Methyl-5-methyl-3-(((4-(7-methyl-12-oxo-3,7,11-triazaspiro[5.6]dodecane-3-carbonyl)phenyl)amino)(phenyl)methylene)-2-oxoindoline-6-carboxylate;

(Z)-Methyl-5-methyl-3-(((4-((2-(4-(methylsulfonyl)piperazin-1-yl)ethyl)carbamoyl)phenyl)amino)(phenyl)methylene)-2-oxoindoline-6-carboxylate;

(Z)-Methyl-3-(((4-(4-hydroxy-4-(morpholinomethyl)piperidine-1-carbonyl)phenyl)amino)(phenyl)methylene)-5-methyl-2-oxoindoline-6-carboxylate;

(Z)-Methyl-3-(((4-(4-(2-hydroxyethyl)-1,4-diazepane-1-carbonyl)phenyl)amino)(phenyl)methylene)-5-methyl-2-oxoindoline-6-carboxylate;

(Z)-Methyl 3-(((4-(4'-carbamoyl-[1,4'-bipiperidine]-1'-carbonyl)phenyl)amino)(phenyl)methylene)-5-methyl-2-oxoindoline-6-carboxylate;

(Z)-Methyl 3-(((4-(((3S,4S)-4-hydroxy-1-methylpyrrolidin-3-yl)(methyl)carbamoyl)phenyl)amino)(phenyl)methylene)-5-methyl-2-oxoindoline-6-carboxylate;

(Z)-Methyl 3-(((4-((1-(2-hydroxyethyl)piperidin-4-yl)carbamoyl)phenyl)amino)(phenyl)methylene)-5-methyl-2-oxoindoline-6-carboxylate;

(Z)-Methyl 3-(((4-(((1-(2-hydroxyethyl)piperidin-4-yl)methyl)carbamoyl)phenyl)amino)(phenyl)methylene)-5-methyl-2-oxoindoline-6-carboxylate;

(Z)-Methyl 3-(((4-((2-((2-hydroxyethyl)(methyl)amino)ethyl)carbamoyl)phenyl)amino)(phenyl)methylene)-5-methyl-2-oxoindoline-6-carboxylate;

(Z)-Methyl 3-(((4-((2-(1,1-dioxidothiomorpholino)ethyl)carbamoyl)phenyl)amino)(phenyl)methylene)-5-methyl-2-oxoindoline-6-carboxylate;

(Z)-Methyl 5-methyl-2-oxo-3-(((4-((2-(5-oxo-1,4-diazepan-1-yl)ethyl)carbamoyl)phenyl)amino)(phenyl)methylene)indoline-6-carboxylate;

(Z)-Methyl 5-methyl-3-(((4-((2-(methyl(2-(methylamino)-2-oxoethyl)amino)ethyl)carbamoyl)phenyl)amino)(phenyl)methylene)-2-oxoindoline-6-carboxylate;

(Z)-Methyl 3-(((3-fluoro-4-((2-(3-oxopiperazin-1-yl)ethyl)carbamoyl)phenyl)amino)(phenyl)methylene)-5-methyl-2-oxoindoline-6-carboxylate;

(Z)-Methyl 5-methyl-2-oxo-3-(((4-((2-(3-oxo-1,4-diazepan-1-yl)ethyl)carbamoyl)phenyl)amino)(phenyl)methylene)indoline-6-carboxylate;

and pharmaceutically acceptable salts of any one thereof.

13. A pharmaceutical composition comprising a compound according to claim 1, in combination with one or more pharmaceutically acceptable diluents or carriers.

* * * * *

UNITED STATES PATENT AND TRADEMARK OFFICE
CERTIFICATE OF CORRECTION

| | | |
|---|---|---|
| PATENT NO. | : 10,669,235 B2 | Page 1 of 1 |
| APPLICATION NO. | : 16/083886 | |
| DATED | : June 2, 2020 | |
| INVENTOR(S) | : Walters et al. | |

It is certified that error appears in the above-identified patent and that said Letters Patent is hereby corrected as shown below:

In the Claims

Claim 12, Column 102, Line 53, the phrase "Z)-Methyl 5-methyl-3-(((4-42-(4-methylpiperazin-1-yl)-2-oxoethyl)carbamoyl)phenyl)amino)(phenyl)methylene)-2-oxoindoline-6-carboxylate" should read "(Z)-Methyl 5-methyl-3-(((4-((2-(4-methylpiperazin-1-yl)-2-oxoethyl)carbamoyl)phenyl)amino)(phenyl)methylene)-2-oxoindoline-6-carboxylate"

Claim 12, Column 103, Line 46, the phrase "(Z)-Methyl 3-(((4-(4-fluoropiperidin-1-yl)ethyl)carbamoyl)phenyl)amino)(phenyl)methylene)-5-methyl-2-oxoindoline-6-carboxylate" should read "(Z)-Methyl 3-(((4-((2-(4-fluoropiperidin-1-yl)ethyl)carbamoyl)phenyl)amino)(phenyl)methylene)-5-methyl-2-oxoindoline-6-carboxylate"

Signed and Sealed this
Ninth Day of March, 2021

Drew Hirshfeld
*Performing the Functions and Duties of the
Under Secretary of Commerce for Intellectual Property and
Director of the United States Patent and Trademark Office*